(12) United States Patent
Delaney et al.

(10) Patent No.: US 12,258,624 B2
(45) Date of Patent: Mar. 25, 2025

(54) CATALYTIC DE-CROSSLINKING OF SAMPLES FOR IN SITU ANALYSIS

(71) Applicant: 10x Genomics, Inc., Pleasanton, CA (US)

(72) Inventors: Joshua Delaney, Oakland, CA (US); Shalini Gohil, Castro Valley, CA (US); Veronica Emelina Gonzalez Muñoz, Palo Alto, CA (US); Joshua Gu, Dublin, CA (US); Albert Dale Kim, Oakland, CA (US); Yi Luo, Dublin, CA (US); Tathagata Mukherjee, San Jose, CA (US); Monica Nagendran, Pleasanton, CA (US); James Francis Perna, III, Hayward, CA (US); Kristen Nguyen Pham, San Jose, CA (US); Meiliana Tjandra, Dublin, CA (US)

(73) Assignee: 10x Genomics, Inc., Pleasanton, CA (US)

(*) Notice: Subject to any disclaimer, the term of this patent is extended or adjusted under 35 U.S.C. 154(b) by 0 days.

(21) Appl. No.: 18/499,129

(22) Filed: Oct. 31, 2023

(65) Prior Publication Data

US 2024/0117410 A1    Apr. 11, 2024

Related U.S. Application Data

(63) Continuation of application No. PCT/US2023/068627, filed on Jun. 16, 2023.

(60) Provisional application No. 63/353,506, filed on Jun. 17, 2022.

(51) Int. Cl.
*C12Q 1/68* (2018.01)
*C12Q 1/6806* (2018.01)
*C12Q 1/6816* (2018.01)
*C12Q 1/6823* (2018.01)
*C12Q 1/6841* (2018.01)
*C12Q 1/6876* (2018.01)

(52) U.S. Cl.
CPC ......... *C12Q 1/6841* (2013.01); *C12Q 1/6806* (2013.01); *C12Q 1/6816* (2013.01); *C12Q 1/6823* (2013.01); *C12Q 1/6876* (2013.01)

(58) Field of Classification Search
CPC ............................ C12Q 1/6806; C12Q 1/6823
See application file for complete search history.

(56) References Cited

U.S. PATENT DOCUMENTS

| | | |
|---|---|---|
| 4,318,846 A | 3/1982 | Khanna et al. |
| 4,757,141 A | 7/1988 | Fung et al. |
| 4,849,336 A | 7/1989 | Miyoshi et al. |
| 5,066,580 A | 11/1991 | Lee |
| 5,073,562 A | 12/1991 | Djuric et al. |
| 5,091,519 A | 2/1992 | Cruickshank |
| 5,151,507 A | 9/1992 | Hobbs et al. |
| 5,188,934 A | 2/1993 | Menchen |
| 5,198,537 A | 3/1993 | Huber et al. |
| 5,344,757 A | 9/1994 | Holtke et al. |
| 5,354,657 A | 10/1994 | Boehringer et al. |
| 5,366,860 A | 11/1994 | Bergot et al. |
| 5,599,675 A | 2/1997 | Brenner |
| 5,635,352 A | 6/1997 | Urdea et al. |
| 5,688,648 A | 11/1997 | Mathies |
| 5,695,940 A | 12/1997 | Drmanac et al. |
| 5,702,888 A | 12/1997 | Holtke et al. |
| 5,750,341 A | 5/1998 | Macevicz |
| 5,752,982 A | 5/1998 | Lang et al. |
| 5,800,996 A | 9/1998 | Lee et al. |
| 5,847,162 A | 12/1998 | Lee et al. |
| 5,990,479 A | 11/1999 | Weiss et al. |
| 6,054,274 A | 4/2000 | Sampson et al. |
| 6,172,218 B1 | 1/2001 | Brenner |
| 6,207,392 B1 | 3/2001 | Weiss et al. |
| 6,251,303 B1 | 6/2001 | Bawendi et al. |
| 6,265,552 B1 | 7/2001 | Schatz |
| 6,291,187 B1 | 9/2001 | Kingsmore et al. |
| 6,306,597 B1 | 10/2001 | Macevicz |
| 6,319,426 B1 | 11/2001 | Bawendi et al. |
| 6,322,901 B1 | 11/2001 | Bawendi et al. |
| 6,323,009 B1 | 11/2001 | Lasken et al. |
| 6,344,329 B1 | 2/2002 | Lizardi et al. |
| 6,368,801 B1 | 4/2002 | Faruqi |
| 6,391,937 B1 | 5/2002 | Beuhler et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,534,266 B1 | 3/2003 | Singer |
| 6,576,291 B2 | 6/2003 | Bawendi et al. |
| 6,828,109 B2 | 12/2004 | Kaplan et al. |

(Continued)

FOREIGN PATENT DOCUMENTS

| | | |
|---|---|---|
| WO | WO 2014/152397 | 9/2014 |
| WO | WO 2016/044313 | 3/2016 |

(Continued)

OTHER PUBLICATIONS

Ali et al. Chem. Soc. Rev. 2014, 43, pp. 3324-3341 (Year: 2014).*
Allawi et al., "Thermodynamics and NMR of internal G.T mismatches in DNA," Biochemistry, (1997) 36:10581-94.
Archer et al., "Selective and flexible depletion of problematic sequences from RNA-seq libraries at the cDNA stage," BMC Genomics. (2014) 15(1):401.

(Continued)

*Primary Examiner* — Jezia Riley

(74) *Attorney, Agent, or Firm* — MORRISON & FOERSTER LLP

(57) ABSTRACT

The present disclosure relates in some aspects to methods and compositions for in situ analysis involving catalytic de-crosslinking of biological samples.

28 Claims, 14 Drawing Sheets

(1 of 14 Drawing Sheet(s) Filed in Color)

(56) References Cited

U.S. PATENT DOCUMENTS

| | | |
|---|---|---|
| 6,969,488 B2 | 11/2005 | Bridgham et al. |
| 7,057,026 B2 | 6/2006 | Barnes et al. |
| 7,255,994 B2 | 8/2007 | Lao |
| 7,264,929 B2 | 9/2007 | Rothberg et al. |
| 7,345,159 B2 | 3/2008 | Ju et al. |
| 7,473,767 B2 | 1/2009 | Dimitrov |
| 7,534,991 B2 | 5/2009 | Miller et al. |
| 7,544,794 B1 | 6/2009 | Benner |
| 7,555,155 B2 | 6/2009 | Levenson et al. |
| 7,566,537 B2 | 7/2009 | Balasubramanian et al. |
| 7,632,641 B2 | 12/2009 | Dirks et al. |
| 7,655,898 B2 | 2/2010 | Miller |
| 7,709,198 B2 | 5/2010 | Luo et al. |
| 7,721,721 B1 | 5/2010 | Kronengold et al. |
| 7,893,227 B2 | 2/2011 | Wu et al. |
| 7,910,304 B2 | 3/2011 | Drmanac |
| 7,914,987 B2 | 3/2011 | Fredriksson et al. |
| 7,919,280 B2 | 4/2011 | Danenberg et al. |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,580,504 B2 | 11/2013 | Fredriksson et al. |
| 8,604,182 B2 | 12/2013 | Luo et al. |
| 8,632,975 B2 | 1/2014 | Vander Horn et al. |
| 8,658,361 B2 | 2/2014 | Wu et al. |
| 8,771,950 B2 | 7/2014 | Church et al. |
| 8,951,726 B2 | 2/2015 | Luo et al. |
| 8,986,926 B2 | 3/2015 | Ferree et al. |
| 9,201,063 B2 | 12/2015 | Sood et al. |
| 9,217,178 B2 | 12/2015 | Fedurco et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,889,422 B2 | 2/2018 | Smith et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,450,599 B2 | 10/2019 | Pierce et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,078,520 B2 | 8/2021 | Church et al. |
| 11,118,220 B2 | 9/2021 | Daugharthy et al. |
| 11,174,281 B1 | 11/2021 | Graham et al. |
| 11,287,422 B2 | 3/2022 | Previte et al. |
| 11,299,767 B2 | 4/2022 | Church et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,643,679 B2 | 5/2023 | Glezer et al. |
| 11,999,999 B2 | 6/2024 | Ju et al. |
| 2002/0045045 A1 | 4/2002 | Adams et al. |
| 2002/0051986 A1 | 5/2002 | Baez et al. |
| 2003/0017264 A1 | 1/2003 | Treadway et al. |
| 2005/0014203 A1 | 1/2005 | Darfler et al. |
| 2005/0100900 A1 | 5/2005 | Kawashima et al. |
| 2006/0188901 A1 | 8/2006 | Barnes et al. |
| 2006/0234261 A1 | 10/2006 | Pierce et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2009/0118128 A1 | 5/2009 | Liu et al. |
| 2009/0202998 A1 | 8/2009 | Schlumpberger et al. |
| 2010/0055733 A1 | 3/2010 | Lutolf et al. |
| 2011/0059865 A1 | 3/2011 | Smith et al. |
| 2011/0223585 A1 | 9/2011 | Gullberg et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0219465 A1 | 8/2017 | Desseroth et al. |
| 2017/0220733 A1 | 8/2017 | Zhuang et al. |
| 2017/0253918 A1 | 9/2017 | Kohman |
| 2017/0283860 A1 | 10/2017 | Kool et al. |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0216162 A1 | 8/2018 | Belhocine et al. |
| 2018/0237864 A1 | 8/2018 | Imler et al. |
| 2018/0251833 A1 | 9/2018 | Daugharthy et al. |
| 2018/0320226 A1 | 11/2018 | Church et al. |
| 2019/0017106 A1 | 1/2019 | Frisen et al. |
| 2019/0032121 A1 | 1/2019 | Daugharthy et al. |
| 2019/0032128 A1 | 1/2019 | Chen et al. |
| 2019/0055594 A1 | 2/2019 | Samusik et al. |
| 2019/0106733 A1 | 4/2019 | Kishi et al. |
| 2019/0112599 A1 | 4/2019 | Church et al. |
| 2019/0119735 A1 | 4/2019 | Deisseroth et al. |
| 2019/0135774 A1 | 5/2019 | Orbal |
| 2019/0155835 A1 | 5/2019 | Daugharthy et al. |

(56) References Cited

U.S. PATENT DOCUMENTS

| | | |
|---|---|---|
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367969 A1 | 12/2019 | Belhocine |
| 2019/0376956 A1 | 12/2019 | Bobrow et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2020/0399689 A1 | 12/2020 | Luo et al. |
| 2021/0017587 A1 | 1/2021 | Cai et al. |
| 2021/0115504 A1 | 4/2021 | Cai et al. |
| 2021/0164039 A1 | 6/2021 | Wang et al. |
| 2021/0190770 A1 | 6/2021 | Delaney et al. |
| 2021/0198723 A1 | 7/2021 | Kuhnemund et al. |
| 2021/0215581 A1 | 7/2021 | Deisseroth et al. |
| 2021/0222234 A1 | 7/2021 | Carlson |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0324450 A1 | 10/2021 | Church et al. |
| 2021/0340618 A1 | 11/2021 | Kuhnemund et al. |
| 2021/0340621 A1 | 11/2021 | Daugharthy et al. |
| 2021/0363579 A1 | 11/2021 | Daugharthy et al. |
| 2021/0388423 A1 | 12/2021 | Bava et al. |
| 2021/0388424 A1 | 12/2021 | Bava |
| 2022/0010358 A1 | 1/2022 | Kuhnemund et al. |
| 2022/0026433 A1 | 1/2022 | Guo et al. |
| 2022/0049302 A1 | 2/2022 | Daugharthy et al. |
| 2022/0049303 A1 | 2/2022 | Busby et al. |
| 2022/0064697 A1 | 3/2022 | Zhuang et al. |
| 2022/0083832 A1 | 3/2022 | Shah |
| 2022/0084628 A1 | 3/2022 | Shah |
| 2022/0084629 A1 | 3/2022 | Shah |
| 2022/0128565 A1 | 4/2022 | Miller et al. |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava |
| 2022/0282319 A1 | 9/2022 | Verheyen |
| 2022/0372570 A1 | 11/2022 | Costa |
| 2022/0380838 A1 | 12/2022 | Kuhnemund et al. |
| 2022/0403458 A1 | 12/2022 | Bava |
| 2022/0404245 A1* | 12/2022 | Chell .................. C12Q 1/6806 |
| 2023/0002808 A1 | 1/2023 | Mignardi |
| 2023/0012607 A1 | 1/2023 | Kuhnemund et al. |
| 2023/0013775 A1 | 1/2023 | Chen et al. |
| 2023/0015226 A1 | 1/2023 | Chen et al. |
| 2023/0026886 A1 | 1/2023 | Chen |
| 2023/0031305 A1 | 2/2023 | Hernandez Neuta et al. |
| 2023/0031996 A1 | 2/2023 | Hernandez Neuta et al. |
| 2023/0035685 A1 | 2/2023 | Hernandez Neuta et al. |
| 2023/0037182 A1 | 2/2023 | Bava et al. |
| 2023/0039148 A1 | 2/2023 | Verheyen |
| 2023/0041485 A1 | 2/2023 | Hernandez Neuta et al. |
| 2023/0044650 A1 | 2/2023 | Dockter |
| 2023/0057571 A1 | 2/2023 | Costa et al. |
| 2023/0061542 A1 | 3/2023 | Kuhnemund |
| 2023/0084407 A1 | 3/2023 | Hernandez Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0220368 A1 | 7/2023 | Kim |
| 2023/0242974 A1 | 8/2023 | Costa et al. |
| 2023/0265488 A1 | 8/2023 | Gohil et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund |
| 2023/0279481 A1 | 9/2023 | Marrache et al. |
| 2023/0287475 A1 | 9/2023 | Chell et al. |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Schnall-Levin |
| 2023/0323430 A1 | 10/2023 | Shastry |
| 2023/0323437 A1 | 10/2023 | Chen et al. |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Bava |
| 2024/0026427 A1 | 1/2024 | Kuhnemund et al. |
| 2024/0026439 A1 | 1/2024 | Sasaki |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen et al. |
| 2024/0060119 A1 | 2/2024 | Bava |
| 2024/0084373 A1 | 3/2024 | Shastry |
| 2024/0084378 A1 | 3/2024 | Marks et al. |
| 2024/0101978 A1 | 3/2024 | Boghospor et al. |
| 2024/0125772 A1 | 4/2024 | Delaney et al. |
| 2024/0132938 A1 | 4/2024 | Kuhnemund |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |
| 2024/0263219 A1 | 8/2024 | Kuhnemund |
| 2024/0263220 A1 | 8/2024 | Olofsson |
| 2024/0264155 A1 | 8/2024 | Costa |

FOREIGN PATENT DOCUMENTS

| | | |
|---|---|---|
| WO | WO 2016/126871 | 8/2016 |
| WO | WO 2016/162309 | 10/2016 |
| WO | WO 2015/188839 | 12/2016 |
| WO | WO 2017/143155 | 8/2017 |
| WO | WO 2017/184984 | 10/2017 |
| WO | WO 2018/026873 | 2/2018 |
| WO | WO 2019/032760 | 2/2019 |
| WO | WO 2019/157529 | 8/2019 |
| WO | WO 2019/199579 | 10/2019 |
| WO | WO 2020/076976 | 4/2020 |
| WO | WO 2020/076979 | 4/2020 |
| WO | WO 2020/077236 | 4/2020 |
| WO | WO 2020/096687 | 5/2020 |
| WO | WO 2020/099640 | 5/2020 |
| WO | WO 2020/117914 | 6/2020 |
| WO | WO 2020/123309 | 6/2020 |
| WO | WO 2020/123316 | 6/2020 |
| WO | WO 2020/123742 | 6/2020 |
| WO | WO 2020/142490 | 7/2020 |
| WO | WO 2020/176788 | 9/2020 |
| WO | WO 2020/240025 | 12/2020 |
| WO | WO 2020/254519 | 12/2020 |
| WO | WO 2021/123282 | 6/2021 |

(56) References Cited

FOREIGN PATENT DOCUMENTS

| | | |
|---|---|---|
| WO | WO 2021/123286 | 6/2021 |
| WO | WO 2021/133842 | 7/2021 |
| WO | WO 2021/138676 | 7/2021 |
| WO | WO 2021/142233 | 7/2021 |
| WO | WO 2021/155063 | 8/2021 |
| WO | WO 2021/167526 | 8/2021 |
| WO | WO 2021/168326 | 8/2021 |
| WO | WO 2021/207610 | 10/2021 |
| WO | WO 2022/025965 | 2/2022 |
| WO | WO 2022/103712 | 5/2022 |
| WO | WO 2023/108139 | 6/2023 |
| WO | WO 2023/141476 | 7/2023 |
| WO | WO 2023/172915 | 9/2023 |
| WO | WO 2021/212042 | 10/2023 |
| WO | WO 2023/192302 | 10/2023 |
| WO | WO 2024/148300 | 7/2024 |

OTHER PUBLICATIONS

Baner et al., "Signal amplification of padlock probes by rolling circle replication," Nucleic Acids Res. (1998) 26(22):5073-5078.

Beechem et al., "High-Plex Spatially Resolved RNA and Protein Detection Using Digital Spatial Profiling: A Technology Designed for Immuno-oncology Biomarker Discovery and Translational Research," Methods Mol Biol. (2020) 2055:563-583.

Bibikova et al., "Quantitative gene expression profiling in formalin-fixed, paraffin-embedded tissues using universal bead arrays," Am J Pathol. Nov. 2004;165(5):1799-807.

Bolognesi et al., "Multiplex Staining by Sequential Immunostaining and Antibody Removal on Routine Tissue Sections," J. Histochem. Cytochem. (2017); 65(8): 431-444.

Capodieci et al., "Gene expression profiling in single cells within tissue," Nat Methods. (2005) 2(9): 663-5.

Chemeris et al., "Real-time hybridization chain reaction," Dokl Biochem Biophys. (2008) 419: 53-55.

Chen et al., "Nanoscale imaging of RNA with expansion microscopy," Nat Methods. (2016) 13:679-684.

Chen et al., "RNA imaging. Spatially resolved, highly multiplexed RNA profiling in single cells," Science. (2015) 348(6233): aaa6090. 16 pgs.

Chen et al., "Expansion Microscopy," Science (2015) 347(6221):543-548.

Choi et al., "Programmable in situ amplification for multiplexed imaging of mRNA expression," Nat Biotechnol. (2010) 28(11): 1208-1212.

Choi et al., "Third-generation in situ hybridization chain reaction: multiplexed, quantitative, sensitive, versatile, robust," Development. (2018) 6;145(12): dev166753.

Conze et al., "Single molecule analysis of combinatorial splicing," Nucleic Acids Res. (2010) 38(16): e163.

Dean et al., "Rapid Amplification of Plasmid and Phage DNA Using Phi29 DNA Polymerase and Multiply-Primed Rolling Circle Amplification," Genome Research (2001) 11:1095-1099.

Dirks et al., "Triggered amplification by hybridization chain reaction," Proc Natl Acad Sci U S A. (2004) 101(43): 15275-15278.

Eng et al., "Transcriptome-scale super-resolved imaging in tissues by RNA seqFISH," Nature. (2019) 568(7751): 235-239.

Evers et al., "The Effect of Formaldehyde Fixation on RNA," J Mol Diagn. (2011) 13(3):282-288.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Femino et al., "Visualization of single RNA transcripts in situ," Science. (1998) 280(5363): 585-90.

Forcucci et al., "All-plastic miniature fluorescence microscope for point-of-care readout of bead-based bioassays," J Biomed Opt. (2015) 20(10): 105010.

Frei et al., "Highly multiplexed simultaneous detection of RNAs and proteins in single cells," Nat Methods. (2016) 13(3): 269-275.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging in Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Gyllborg et al., "Hybridization-based in situ sequencing (HybISS) for spatially resolved transcriptomics in human and mouse brain tissue," Nucleic Acids Res. (2020) 48(19): e112.

Han et al., "Quantum-dot-tagged microbeads for multiplexed optical coding of biomolecules," Nat Biotechnol. (2001) 19(7): 631-5.

Henegariu et al., "Custom fluorescent-nucleotide synthesis as an alternative method for nucleic acid labeling," Nature Biotechnol. (2000) 18:345.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Jamur et al., "Permeabilization of cell membranes," Method Mol. Biol. (2010) 588: 63-66 (abstract only).

Kanehisa, "Use of statistical criteria for screening potential homologies in nucleic acid sequences," Nucleic Acids Res. (1984) 12:203-213.

Karmaker et al., "Organocatalytic removal of formaldehyde adducts from RNA and DNA bases," Nat Chem. (2015) 7(9):752-8.

Korlach et al. "Selective aluminum passivation for targeted immobilization of single DNA polymerase molecules in zero-mode waveguide nanostructures." *Proceedings of the National Academy of Sciences* 105.4 (2008): 1176-1181.

Lagunavicius et al., "Novel application of Phi29 DNA polymerase: RNA detection and analysis in vitro and in situ by target RNA-primed RCA," RNA. (2009) 15(5):765-71.

Lakowicz et al., "Silver particles enhance emission of fluorescent DNA oligomers," Bio Techniques (2003) 34(1); 62-66.

Larsson et al. "In situ detection and genotyping of individual mRNA molecules," Nat Methods. (2010) 7(5):395-397.

Lee et al. "Highly Multiplexed Subcellular RNA Sequencing In Situ", Science (2014) 343(6177):1360-1363.

Levene et al. "Zero-mode waveguides for single-molecule analysis at high concentrations." *science* 299.5607 (2003): 682-686.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lizardi et al., "Mutation detection and single-molecule counting using isothermal rolling-circle amplification," Nat Genet. (1998) 19(3): 225-232.

Lundquist et al. "Parallel confocal detection of single molecules in real time." Optics letters 33.9 (2008): 1026-1028.

Lyamichev et al., "Comparison of the 5' nuclease activities of taq DNA polymerase and its isolated nuclease domain," Proc Natl Acad Sci USA. (1999) 96(11): 6143-6148.

(56) References Cited

OTHER PUBLICATIONS

Ma et al., "RNA template-dependent 5' nuclease activity of Thermus aquaticus and Thermus thermophilus DNA polymerases," J Biol Chem. (2000) 275(32): 24693-700.
Maierhorfer et al., "Multicolor deconvolution microscopy of thick biological specimens," Am J Pathol. (2003) 162(2): 373-9.
Masuda et al., "Analysis of chemical modification of RNA from formalin-fixed samples and optimization of molecular biology applications for such samples," Nucleic Acids Res. (1999) 27(22):4436-43.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Mitra et al., "Fluorescent in situ sequencing on polymerase colonies," Anal. Biochem. (2003) 320, 55-65.
Moffitt et al., "RNA Imaging with Multiplexed Error-Robust Fluorescence In Situ Hybridization (MERFISH)," Methods in Enzymology, (2016) 572; 1-49.
Mohsen et al., "The Discovery of Rolling Circle Amplification and Rolling Circle Transcription," Acc Chem Res. (2016) 49(11): 2540-2550.
Nagaki et al., "Decrosslinking enables visualization of RNA-guided endonuclease-in situ labeling signals for DNA sequences in plant tissues," J Exp Bot. (2020) 71(6):1792-1800.
Nagendran et al., "Automated cell-type classification in intact tissues by single-cell molecular profiling," Elife. (2018) 7:e30510.
Nallur et al., "Signal amplification by rolling circle amplification on DNA microarrays," Nucleic Acids Res. (2001) 29(23): e118.
Niu et al., "Fluorescence detection for DNA using hybridization chain reaction with enzyme-amplification," Chem C+A277ommun (Camb). (2010) 46(18): 3089-91.
Payne et al. "In situ genome sequencing resolves DNA sequence and structure in intact biological samples," Science. (2021) 371(6532): eaay3446. doi: 10.1126/science.aay3446. Epub Dec. 31, 2020.
Pirici et al., "Antibody elution method for multiple immunohistochemistry on primary antibodies raised in the same species and of the same subtype," J Histochem Cytochem. (2009) 57(6); 567-75.
Raj et al., "Imaging individual mRNA molecules using multiple singly labeled probes," Nat Methods. (2008) 5(10): 877-879.
Rajeswari et al., "Multiple pathogen biomarker detection using an encoded bead array in droplet PCR," J Microbiol Methods. (2017) 139: 22-28.
Rouhanifard et al. "ClampFISH detects individual nucleic acid molecules using click chemistry-based amplification," Nat Biotechnol. (2018) 17 pages. doi: 10.1038/nbt.4286.
Schweitzer et al. "Immunoassays with rolling circle DNA amplification: A versatile platform for ultrasensitive antigen detection," Proc. Natl Acad. Sci. USA (2000) 97:10113-119.
Schweitzer et al., "Multiplexed protein profiling on microarrays by rolling-circle amplification," Nature Biotech. (2002) 20:359-365.
Shendure et al, "Accurate multiplex polony sequencing of an evolved bacterial genome," Science (2005) 309(5741); 1728-1732.
Soderberg et al. "Characterizing proteins and their interactions in cells and tissues using the in situ proximity ligation assay." *Methods* 45.3 (2008): 227-232.
Song et al., "Hybridization chain reaction-based aptameric system for the highly selective and sensitive detection of protein," Analyst. (2012) 137(6):1396-1401.
Sun et al., "Composite organic-inorganic nanoparticles as Raman labels for tissue analysis," Nano Lett. (2007) 7(2): 351-6.
Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.
Tripathi et al., "Z Probe, An Efficient Tool for Characterizing Long Non-Coding RNA in FFPE Tissues," Noncoding RNA. (2018) 4(3):20.

Tsuneoka et al., "Modified in situ Hybridization Chain Reaction Using Short Hairpin DNAs," Front Mol Neurosci. (2020) 13:75.
Vandernoot et al., "cDNA normalization by hydroxyapatite chromatography to enrich transcriptome diversity in RNA-seq applications," Biotechniques, (2012) 53(6) 373-80.
Wählby et al., "Sequential immunofluorescence staining and image analysis for detection of large numbers of antigens in individual cell nuclei," Cytometry. (2002) 47(1):32-41.
Wang et al., "Three-dimensional intact-tissue sequencing of single-cell transcriptional states," Science. (2018) 361(6400): eaat5691.
Weibrecht et al., "Simultaneous visualization of both signaling cascade activity and end-point gene expression in single cells," PLoS One. (2011) 6(5): e20148.
Wetmur, "Dna Probes: Applications of the Principles of Nucleic Acid Hybridization," Critical Reviews in Biochemistry and Molecular Biology, (1991) 26(91); 227-259.
Wilson et al., "Encoded microcarriers for high-throughput multiplexed detection," Angew Chem Int Ed Engl. (2006) 18;45(37): 6104-17.
Wu, C. et al. "RollFISh Achieves Robust Quantification of Single-Molecule RNA Biomarkers Iin Paraffin-Embedded Tumor Tissue Samples," Commun Biol. (2018) 1:209):1-8. doi: 10.1038/s42003-018-0218-0.
Xia et al. "Multiplexed detection of RNA using MERFISH and branched DNA amplification." Scientific reports 9.1 (2019): 1-13.
Zhao et al., "Advances of multiplex and high throughput biomolecular detection technologies based on encoding microparticles," Sci China Chem. (2011) 54(8):1185.
Adam et al., "Psychrophilic proteases dramatically reduce single-cell RNA-seq artifacts: a molecular atlas of kidney development," Development. Oct. 1, 2017;144(19):3625-3632.
Crisalli et al., "Water-soluble Organocatalysts for Hydrazone and Oxime Formation," J Org Chem. Feb. 1, 2013; 78(3): 1184-1189. doi:10.1021/jo302746p.
Eastburn et al., "Identification and genetic analysis of cancer cells with PCR-activated cell sorting," Nucleic Acids Res. (2014); 42(16):e128.
Eastburn et al., "Ultrahigh-throughput Mammalian single-cell reverse-transcriptase polymerase chain reaction in microfluidic drops," Anal Chem. Aug. 20, 2013;85(16):8016-21.
Kuliszewska Edyta et al., "On the rearrangement of N-aryl-N-Boc-phosphoramidates to N-Boc-protected o-aminoarylphosphonates", Monatsh Chem. (2018);149(1):87-98.
Mabruk, Mohamd. "In situ hybridization: detecting viral nucleic acid in formalin-fixed, paraffin-embedded tissue samples," Expert Rev. Mol. Diagn. (2004) 4(5); 653-661.
O'Flanagan et al., "Dissociation of solid tumor tissues with cold active protease for single-cell RNA-seq minimizes conserved collagenase-associated stress responses," Genome Biol. Oct. 17, 2019;20(1):210.Retrieved from the Internet: URL:http://link.springer.com/article/10.1186/s13059-019-1830-0/fulltext.html.
Pellegrino et al., "High-throughput single-cell DNA sequencing of acute myeloid leukemia tumors with droplet microfluidics," Genome Res. (2018) 28(9):1345-1352.
Sigma-Aldrich, Safety Data Sheet "2-Amino-5-methylbenzoic acid," Version 4.4, Jul. 3, 2014.
Soderberg, Lovisa, "Droplet Microfluidics reverse transcription and PCR towards Single Cell and Exosome Analysis," ISBN: 9789177295778; Jan. 1, 2017 (Jan. 1, 2017), Retrieved from the Internet: URL:https://pdfs.semanticscholar.org/01d1/f6913a0066913a9eb7a9dbe3916c2eebe19a.pdf.
Villacampa et al., "Genome-wide Spatial Expression Profiling in FFPE Tissues," bioRxiv. (2020); 38 pages.
Chen et al., "Efficient in situ barcode sequencing using padlock probe-based BaristaSeq," Nucleic Acids Res. (2018) 46(4): e22.
Sun et al., "Integrating barcoded neuroanatomy with spatial transcriptional profiling enables identification of gene correlates of projections," Nat Neurosci. (2021) 24(6):873-885.

\* cited by examiner

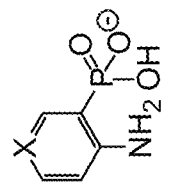
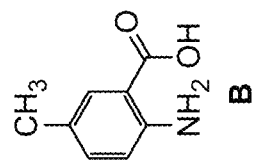
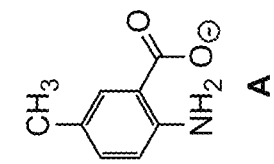
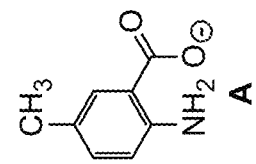
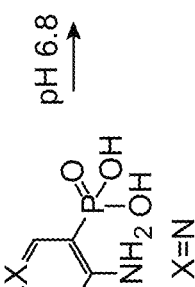
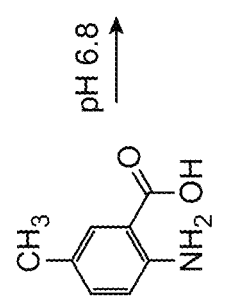
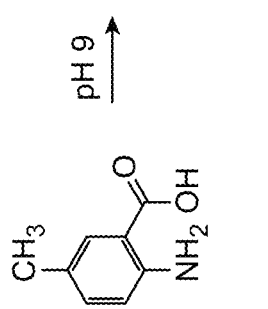
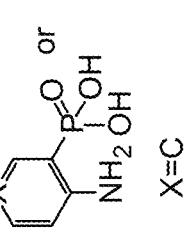
FIG. 3B
FIG. 3C
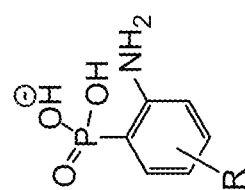
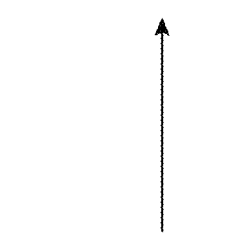
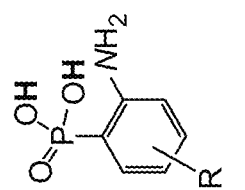
FIG. 3A

CATALYTIC DE-CROSSLINKING OF SAMPLES FOR IN SITU ANALYSIS

CROSS-REFERENCE TO RELATED APPLICATIONS

This application is a continuation of International Patent Application No. PCT/US2023/068627, filed Jun. 16, 2023, entitled "CATALYTIC DE-CROSSLINKING OF SAMPLES FOR INSITU ANALYSIS," which claims priority to U.S. Provisional Patent Application No. 63/353,506, filed Jun. 17, 2022, entitled "CATALYTIC DE-CROSSLINKING OF SAMPLES FOR IN SITU ANALYSIS," each of which is herein incorporated by reference in its entirety for all purposes.

FIELD

The present disclosure relates in some aspects to compositions and methods for catalytic de-crosslinking of a fixed biological sample and for preparing the biological sample for in situ analysis.

BACKGROUND

Methods are available for analyzing analytes such as nucleic acids and proteins present in a biological sample, e.g., a cell or tissue sample. Current methods for analyzing analytes in situ can have low sensitivity and specificity, have high background and/or low signal-to-noise ratio (e.g., due to autofluorescence), have limited plexity, or be biased, time-consuming, labor-intensive, and/or error-prone. Improved methods for analyzing analytes in a biological sample are needed. Provided herein are methods and compositions that meet such and other needs.

SUMMARY

Nucleic acid probe-based assay methods for in situ analysis such as single molecule fluorescent hybridization (smFISH) have enabled nanoscale-resolution imaging of RNA in cells and tissues. However, most methods of analyte detection are not compatible with fixed tissues without specific sample preparation to clear crosslinking and render analytes accessible to biochemical reactions. In one aspect, background autofluorescence can arise from and/or be exacerbated by sample fixation/crosslinking, such as formalin-fixation. Background autofluorescence may have a significant, ongoing impact on the ability to detect and resolve fluorescence signals from analytes of interest over other components also present in the biological samples, especially when analysis is carried out over multiple rounds of imaging. In another aspect, molecular crosslinks may render analytes (e.g., nucleic acid sequences, epitopes, and/or antigens) less accessible to detection reagents such as labelling agents (e.g., nucleic acid probes targeting cellular DNA or RNA, or antibodies targeting protein analytes), thereby reducing detection efficiency and sensitivity. As such, de-crosslinking fixed samples for in situ analysis is critical and improved methods are needed.

In some embodiments, provided herein is a method comprising: a) providing a biological sample immobilized on a substrate, wherein the biological sample is fixed; b) contacting the biological sample with a catalyst that catalyzes de-crosslinking of molecular crosslinks in the biological sample; c) contacting the biological sample with a labelling agent that directly or indirectly binds to an analyte at a location in the biological sample; and d) detecting an optical signal associated with the labelling agent or a product thereof, thereby detecting the analyte at the location in the biological sample.

In some embodiments, disclosed herein is a method for sample analysis, comprising: a) providing a biological sample immobilized on a substrate, wherein the biological sample is fixed; b) contacting the biological sample with a catalyst that catalyzes de-crosslinking of molecular crosslinks in the biological sample; c) contacting the biological sample with a labelling agent that directly or indirectly binds to an analyte at a location in the biological sample; and d) detecting an optical signal associated with the labelling agent or a product thereof, thereby detecting the analyte at the location in the biological sample.

In some embodiments, the molecular crosslinks are products of one or more crosslinking agents. In some embodiments, the one or more crosslinking agents comprise an aldehyde, optionally wherein the crosslinking agent comprises formaldehyde. In any of the embodiments herein, the molecular crosslinks can be on RNA, DNA, protein, carbohydrate, lipid, and/or other molecules in the biological sample.

In any of the embodiments herein, the catalyst can catalyze de-crosslinking of inter-molecular crosslinks and/or intra-molecular crosslinks in the biological sample, optionally wherein the inter-molecular crosslinks and/or intra-molecular crosslinks comprise an aminal bridge. In any of the embodiments herein, the catalyst can be a water-soluble catalyst. In any of the embodiments herein, the catalyst can be an organic molecule. In any of the embodiments herein, the catalyst can be a transimination catalyst. In any of the embodiments herein, the catalyst can catalyze de-crosslinking of aminal crosslinks in the biological sample. In any of the embodiments herein, the catalyst can catalyze breakdown of hemi-aminal adducts and/or aminal adducts in the biological sample.

In any of the embodiments herein, the catalyst can be a compound of formula (I),

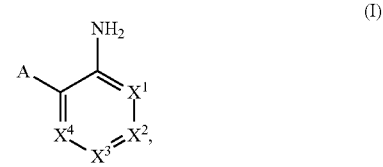

or a salt, zwitterion, or solvate thereof, wherein: A is selected from the group consisting of —COOH, —P(=O)(OH)$_2$, and S(=O)$_2$OH; $X^1$, $X^2$, $X^3$, and $X^4$ are each independently selected from the group consisting of: CH, CR, and N; each occurrence of R is independently selected from the group consisting of C$_{1-6}$ alkyl, C$_{1-6}$ haloalkyl, C$_{1-6}$ alkoxy, —NO$_2$, —NR'R", and —C(=O)NR'R"; and each occurrence of R' and R" is independently selected from the group consisting of H and C$_{1-6}$ alkyl which is optionally substituted with

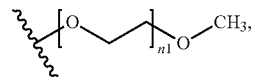

wherein n1 is an integer from 12 to 16.

In any of the preceding embodiments, the catalyst can comprise one or more compounds selected from the group consisting of

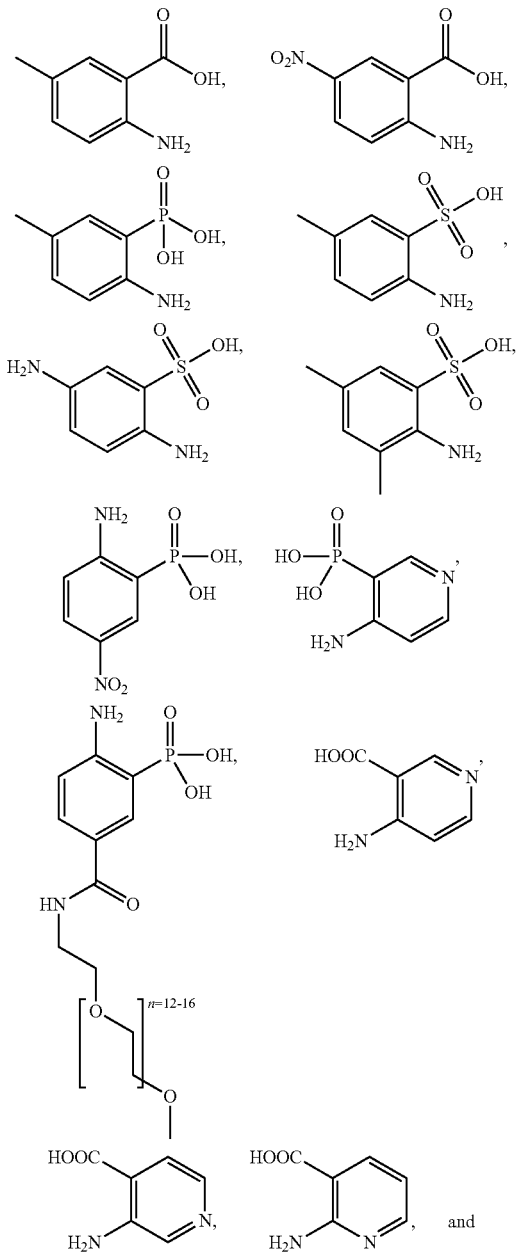

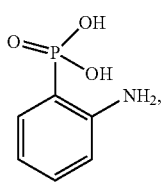

and or a salt, zwitterion, or solvate thereof. In any of the preceding embodiments, the catalyst can comprise

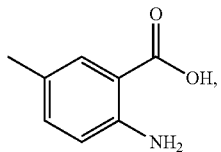

or a salt, zwitterion, or solvate thereof. In any of the preceding embodiments, the catalyst can comprise

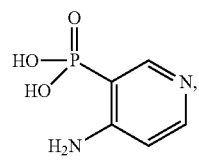

or a salt, zwitterion, or solvate thereof. In any of the preceding embodiments, the catalyst can comprise

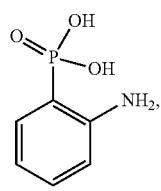 [SMILES: Nc1ccccc1P(=O)(O)O]

or a salt, zwitterion, or solvate thereof. In any of the preceding embodiments, the catalyst can comprise

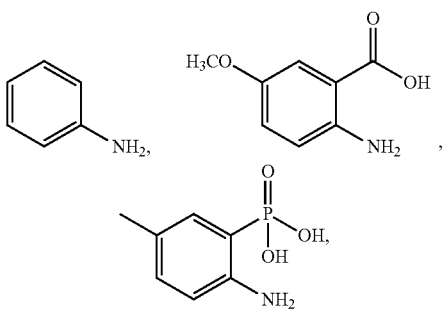

or a combination thereof, or a salt, zwitterion, or solvate thereof. In any of the preceding embodiments, the catalyst can comprise

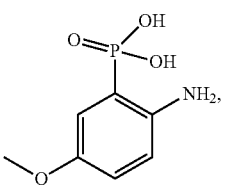

or a salt, zwitterion, or solvate thereof. In any of the preceding embodiments, the catalyst can comprise

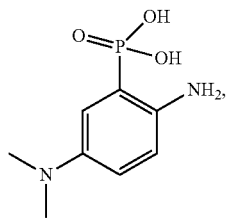

or a salt, zwitterion, or solvate thereof.

In any of the embodiments herein, the catalyst can be a compound of formula (II),

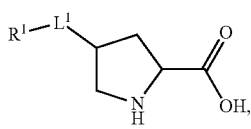

or a salt, zwitterion, or solvate thereof, wherein: $L^1$ is selected from the group consisting of —O—, —N(H)—, —N($C_{1-3}$ alkyl)-, —N($CH_2CH_2O)_{1-10}$—$CH_3$—, —S(O)$_{0-2}$—, —$CH_2$—, and a bond; $R^1$ is selected from the group consisting of: H; $C_{1-6}$ alkyl; $C_{1-6}$ haloalkyl; $C_{6-10}$ aryl optionally substituted with 1-4 $R^b$; and 5- to 10-membered heteroaryl, wherein 1-4 ring atoms are heteroatoms each independently selected from the group consisting of: N, N(H), N($C_{1-3}$ alkyl), O, and S, wherein the heteroaryl is optionally substituted with 1-4 independently selected $R^b$; and each $R^b$ is independently selected from the group consisting of: halo, cyano, —OH, —$NH_2$, —NH($C_{1-3}$ alkyl), —N($C_{1-3}$ alkyl)$_2$, $C_{1-6}$ alkyl, $C_{1-6}$ haloalkyl, $C_{1-4}$ alkoxy, and $C_{1-4}$ haloalkoxy.

In some embodiments, the catalyst comprises

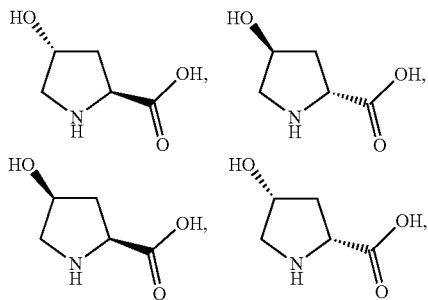

or a salt, zwitterion, or solvate thereof.

In any of the embodiments herein, the substrate can comprise a planar surface configured to contact the biological sample. In any of the embodiments herein, the substrate may but does not need to comprise a bead, particle, or microwell. In any of the preceding embodiments, the substrate can be transparent. In any of the preceding embodiments, the substrate can be a glass slide or a plastic slide. In any of the preceding embodiments, the substrate may but does not need to comprise nucleic acid immobilized thereon prior to contacting the biological sample.

In any of the preceding embodiments, the biological sample can be a tissue section. In any of the preceding embodiments, the biological sample can comprise cells immobilized on the substrate. In some embodiments, the cells are dissociated cells, cultured cells, and/or cells isolated from a subject. In any of the preceding embodiments, the biological sample can be an aldehyde-fixed biological sample. In any of the preceding embodiments, the biological sample can be a formaldehyde-fixed biological sample. In any of the preceding embodiments, the biological sample can be a paraffinized biological sample. In some embodiments, the biological sample is a formaldehyde-fixed paraffin-embedded (FFPE) biological sample. In any of the preceding embodiments, the biological sample can be a fresh frozen biological sample that has been crosslinked.

In any of the preceding embodiments, the method can comprise, prior to contacting the biological sample with the catalyst, a step of dehydrating the biological sample. In some embodiments, the dehydrating step comprises drying the biological sample at 42° C. for 3 hours or drying the biological sample at room temperature overnight. In any of the preceding embodiments, the method can comprise, prior to contacting the biological sample with the catalyst, a step of baking the biological sample. In some embodiments, the baking step comprises baking the biological sample uncovered at 60° C. for 2 hours. In any of the preceding embodiments, the method can comprise, prior to contacting the biological sample with the catalyst, a step of de-paraffinizing the biological sample. In some embodiments, the de-paraffinizing comprises contacting the biological sample with xylene, ethanol, and water, or, sequentially contacting the biological sample with xylene, absolute ethanol, about 96% ethanol, and about 70% ethanol. In any of the preceding embodiments, the method can comprise, prior to contacting the biological sample with the catalyst, a step of re-hydrating the biological sample. In some embodiments, the re-hydrating comprises sequentially contacting the biological sample with 100% ethanol, 100% ethanol, 96% ethanol, 70% ethanol, each for 3 minutes, followed by contacting the biological sample with nuclease free water for 20 seconds.

In any of the preceding embodiments, the method can comprise, prior to contacting the biological sample with the catalyst, a step of pretreating the biological sample. In some embodiments, the pretreating comprises contacting the biological sample with a proteinase. In some embodiments, the proteinase is a collagenase. In some embodiments, the proteinase is present in a solution or suspension comprising a buffer. In any of the preceding embodiments, the method can comprise, prior to contacting the biological sample with the catalyst, a step of permeabilizing the biological sample. In any of the preceding embodiments, the method can comprise, prior to contacting the biological sample with the catalyst, a step of staining the biological sample and imaging the stained biological sample. In some embodiments, the staining comprises the use of a histological stain and/or an immunological stain.

In any of the preceding embodiments, the catalyst can be contacted with the biological sample at a concentration between about 5 mM and about 500 mM. In any of the preceding embodiments, the catalyst can be contacted with the biological sample at a concentration between about 10 mM and about 400 mM. In any of the preceding embodiments, the catalyst can be contacted with the biological sample at a concentration between about 50 mM and about 300 mM. In any of the preceding embodiments, the catalyst can be contacted with the biological sample at a concentration between about 75 mM and about 250 mM In any of the preceding embodiments, the catalyst can be contacted with the biological sample at a concentration between about 100 mM and about 200 mM.

In any of the preceding embodiments, the catalyst can be contacted with the biological sample for about 1 minute to about 150 minutes. In any of the preceding embodiments, the catalyst can be contacted with the biological sample for about 5 minute to about 100 minutes. In any of the preceding embodiments, the catalyst can be contacted with the biological sample for about 10 minute to about 50 minutes. In any of the preceding embodiments, the catalyst can be contacted with the biological sample for about 15 minute to about 30 minutes.

In any of the preceding embodiments, the catalyst can be contacted with the biological sample at a temperature between about 5° C. and about 100° C. In any of the preceding embodiments, the catalyst can be contacted with the biological sample at a temperature between about 50° C. and about 95° C. In any of the preceding embodiments, the catalyst can be contacted with the biological sample at a temperature between about 75° C. and about 90° C. In some embodiments, the catalyst is contacted with the biological sample at 80° C. for 30 minutes.

In any of the preceding embodiments, a solution or a suspension comprising the catalyst and a buffer can contacted with the biological sample. In some embodiments, the buffer comprises citrate, tris(hydroxymethyl)aminomethane (Tris), phosphate-buffered saline (PBS), 2-[4-(2-hydroxyethyl)piperazin-1-yl]ethanesulfonic acid (HEPES), 2-(N-morpholino)ethanesulfonic acid (MES), or a combination thereof. In any of the preceding embodiments, the buffer can comprise dimethyl sulfoxide (DMSO). In any of the preceding embodiments, the buffer can comprise Tris and a chelating agent, optionally wherein the chelating agent is ethylenediaminetetraacetic acid (EDTA) and the buffer is Tris-EDTA (TE).

In any of the preceding embodiments, the buffer can be present in the solution or suspension at a concentration between about 5 mM and about 250 mM. In any of the preceding embodiments, the buffer can be present in the solution or suspension at a concentration between about 100 mM and about 200 mM. In any of the preceding embodiments, the solution or suspension can have a pH between about 4 and about 10 In any of the preceding embodiments, the solution or suspension can have a pH between about 6 and about 8.

In any of the preceding embodiments, the solution or suspension can comprise sodium dodecyl sulfate (SDS), urea, and/or a proteinase. In some embodiments, the proteinase is proteinase K. In any of the preceding embodiments, the solution or suspension can comprise sodium dodecyl sulfate (SDS) and proteinase K. In any of the preceding embodiments, the solution or suspension can comprise urea and proteinase K. In some embodiments, the urea concentration is between about 0.01 M and about 1 M. In some embodiments, the proteinase K concentration is between about 0.1 μg/mL and about 2 μg/mL. In some embodiments, the urea concentration is about 0.5 M and the proteinase K concentration is between about 0.5 μg/mL and about 1 μg/mL.

In any of the preceding embodiments, contacting the biological sample with the catalyst can substantially preserve adhesion of the biological sample to the substrate, and/or contacting the biological sample with the catalyst can substantially preserve integrity of the biological sample.

In any of the preceding embodiments, the method can comprise: after contacting the biological sample with the catalyst, a step of washing the biological sample, optionally wherein the washing comprises washing the biological sample in phosphate-buffered saline with Tween detergent (PBST) for 1 minute for three times; a step of permeabilizing the biological sample before, during, and/or after contacting the biological sample with the catalyst; and/or a step of staining the biological sample and imaging the stained biological sample, optionally wherein the staining comprises the use of a histological stain and/or an immunological stain.

In any of the preceding embodiments, the analyte or product thereof can remain in the biological sample during the contacting with the catalyst, during the contacting with the labelling agent, and during detecting the optical signal; and/or the analyte or product thereof can substantially remain at the location during the contacting with the catalyst, during the contacting with the labelling agent, and during detecting the optical signal.

In any of the preceding embodiments, the method may but does not need to comprise migrating the analyte or a product thereof towards the substrate. In some embodiments, the migration is passive migration or active migration. In any of the preceding embodiments, the method may but does not need to comprise migrating the analyte or a product thereof outside the biological sample. In any of the preceding embodiments, the method may but does not need to comprise capturing the analyte or a product thereof by a capture agent immobilized on the substrate.

In any of the preceding embodiments, the labelling agent may but does not need to be immobilized on the substrate prior to contacting the biological sample. In any of the preceding embodiments, a solution or a suspension comprising the labelling agent can be contacted with the biological sample. In any of the preceding embodiments, the labelling agent can comprise a binding moiety. In some embodiments, the binding moiety comprises a nucleic acid or an antibody or epitope binding fragment thereof. In any of the preceding embodiments, the labelling agent can comprise a detectable label. In some embodiments, the detectable label comprises a nucleic acid or an optically detectable label. In any of the preceding embodiments, the labelling agent can comprise a reporter oligonucleotide. In some embodiments, the reporter oligonucleotide comprises a barcode sequence.

In any of the preceding embodiments, the analyte is a cellular nucleic acid. In some embodiments, the cellular nucleic acid is genomic DNA, mRNA, or cDNA. In some embodiments, the labelling agent is a primary probe that hybridizes to the cellular nucleic acid. In some embodiments, the primary probe comprises a barcode sequence. In any of the preceding embodiments, the primary probe can be selected from the group consisting of: a primary probe comprising a 3' or 5' overhang upon hybridization to the cellular nucleic acid, optionally wherein the 3' or 5' overhang comprises one or more barcode sequences; a primary probe comprising a 3' overhang and a 5' overhang upon hybridization to the cellular nucleic acid, optionally wherein the 3' overhang and the 5' overhang each independently comprises one or more barcode sequences; a circular primary probe; a circularizable primary probe or probe set; a primary probe or probe set comprising a split hybridization region configured to hybridize to a splint, optionally wherein the split hybridization region comprises one or more barcode sequences; and a combination thereof. In some embodiments, the labelling agent is a detectable probe that hybridizes to a primary probe or a product or complex thereof, wherein the primary probe hybridizes to the cellular nucleic acid. In some embodiments, the product or complex of the primary probe is selected from the group consisting of: a rolling circle amplification (RCA) product, a complex comprising an initiator and an amplifier for hybridization chain reaction (HCR), a complex comprising an initiator and an amplifier for linear oligonucleotide hybridization chain reaction (LO-HCR), a primer exchange reaction (PER) product, and a complex comprising a pre-amplifier and an amplifier for branched DNA (bDNA). In any of the preceding embodiments, the detectable probe can hybridize to a barcode sequence in the primary probe or product or complex thereof. In any of the preceding embodiments, the detectable probe can comprise a barcode sequence in a region that does not hybridize to the primary probe or product or complex thereof. In any of the preceding embodiments, the detectable probe can be selected from the group consisting of: a detectable probe comprising a 3' or 5' overhang upon hybridization to the primary probe or product or complex thereof, optionally wherein the 3' or 5' overhang comprises one or more barcode sequences; a detectable probe comprising a 3' overhang and a 5' overhang upon hybridization to the primary probe or product or complex thereof, optionally wherein the 3' overhang and the 5' overhang each independently comprises one or more barcode sequences; a circular detectable probe; a circularizable detectable probe or probe set; a detectable probe or probe set comprising a split hybridization region configured to hybridize to a splint, optionally wherein the split hybridization region comprises one or more barcode sequences; and a combination thereof. In any of the preceding embodiments, the detectable probe can comprise a fluorescent label. In any of the preceding embodiments, the detectable probe can comprise a region for binding to a fluorescently labelled probe.

In any of the preceding embodiments, the analyte can comprise a non-nucleic acid moiety, optionally wherein the non-nucleic acid moiety is a protein, a carbohydrate, a lipid, a small molecule, or a complex thereof. In some embodiments, the labelling agent comprises i) an analyte-binding region that directly or indirectly binds to the non-nucleic acid moiety and ii) a reporter oligonucleotide, optionally wherein the analyte-binding region is an antibody or epitope binding fragment thereof.

In any of the preceding embodiments, the method can comprise: contacting the biological sample with a first labelling agent that directly or indirectly binds to a nucleic acid analyte at a first location in the biological sample, and detecting a first optical signal associated with the first labelling agent or a product thereof, and contacting the biological sample with a second labelling agent that directly or indirectly binds to a protein analyte at a second location in the biological sample, and detecting a second optical signal associated with the second labelling agent or a product thereof, thereby detecting the nucleic acid analyte and the protein analyte at the first and second locations in the biological sample, respectively.

In some embodiments, the nucleic acid analyte is an mRNA, and the protein analyte is an intracellular protein, a membrane-bound protein, or an extracellular protein. In any of the preceding embodiments, the first and second locations can be the same location or different locations.

In any of the preceding embodiments, the product of the labelling agent can be generated in situ in the biological sample. In any of the preceding embodiments, the optical signal can be detected in situ in the biological sample. In any of the preceding embodiments, the optical signal can be detected by imaging the biological sample. In some embodiments, the imaging comprises fluorescent microscopy.

In any of the preceding embodiments, the number of optical signals detected in a unit area in the biological sample can be greater than that without contacting the biological sample with the catalyst. In any of the preceding embodiments, the analyte comprises a nucleic acid and the number of optical signals detected per unit nuclei area in the biological sample can be greater than that without contacting the biological sample with the catalyst. In any of the preceding embodiments, the intensity of the optical signal detected in the biological sample can be greater than that without contacting the biological sample with the catalyst. In any of the preceding embodiments, the signal-to-noise ratio of the optical signal detected in the biological sample can be greater than that without contacting the biological sample with the catalyst.

In some aspects, disclosed herein is a method for sample analysis, comprising: a) contacting a biological sample with a catalyst that catalyzes de-crosslinking of molecular cross-links in the biological sample, wherein the biological sample is a formaldehyde-fixed biological sample immobilized on a substrate before contacting with the catalyst, and wherein the catalyst is a compound of formula (I),

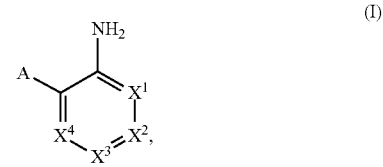

or a salt, zwitterion, or solvate thereof, wherein: A is selected from the group consisting of —COOH, —P(═O)(OH)$_2$, and S(═O)$_2$OH; $X^1$, $X^2$, $X^3$, and $X^4$ are each independently selected from the group consisting of: CH, CR$^a$, and N; each occurrence of R$^a$ is independently selected from the group consisting of C$_{1-6}$ alkyl, C$_{1-6}$ haloalkyl, C$_{1-6}$ alkoxy, —NO$_2$, —NR'R", and —C(═O)NR'R"; and each occurrence of R' and R" is independently selected from the group consisting of H and C$_{1-6}$ alkyl which is optionally substituted with

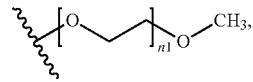

wherein n1 is an integer from 12 to 16; b) contacting the biological sample with a detectable probe that directly or indirectly binds to a nucleic acid at a first location in the biological sample; and c) detecting an optical signal associated with the detectable probe, thereby detecting the nucleic acid at the first location in the biological sample.

In some embodiments, the biological sample is contacted with a solution or suspension comprising the catalyst in a citrate buffer between pH 5 and pH 7. In some embodiments, the biological sample is contacted with a solution or suspension comprising the catalyst in a TE buffer between pH 8.5 and pH 9.5. In some embodiments, the biological sample is contacted with a solution or suspension comprising the catalyst in a PBS buffer between pH 6.8 and pH 8.0. In any of the preceding embodiments, the catalyst concentration in the solution or suspension can be between about 50 mM and about 400 mM. In any of the preceding embodiments, the catalyst concentration in the solution or suspension can be between about 100 mM and about 200 mM.

In any of the preceding embodiments, the biological sample can be catalytically de-crosslinked at a temperature between about 60° C. and about 95° C. In any of the preceding embodiments, the biological sample can be catalytically de-crosslinked at a temperature between about 70° C. and about 90° C. In any of the preceding embodiments, the biological sample can be catalytically de-crosslinked at a temperature between about 75° C. and about 85° C. In any of the preceding embodiments, the biological sample can be catalytically de-crosslinked at a temperature between about 75° C. and about 85° C. In any of the preceding embodiments, the biological sample can be catalytically de-crosslinked for about 5 minutes to about 1 hour. In any of the preceding embodiments, the biological sample can be catalytically de-crosslinked for about 10 minutes to about 45 minutes. In any of the preceding embodiments, the biological sample can be catalytically de-crosslinked for about 15 minutes to about 30 minutes.

In any of the preceding embodiments, the nucleic acid can be an RNA in the biological sample. In any of the preceding embodiments, the nucleic acid can be a nucleic acid probe that directly or indirectly binds to an RNA in the biological sample. In any of the preceding embodiments, the nucleic acid can be a product of an RNA in the biological sample, optionally wherein the nucleic acid is a cDNA of the RNA. In any of the preceding embodiments, the nucleic acid can be a product of a nucleic acid probe that directly or indirectly binds to an RNA in the biological sample. In some embodiments, the nucleic acid is a rolling circle amplification product (RCP).

In any of the preceding embodiments, the method can comprise: d) contacting the biological sample with a detectably labelled antibody or an epitope binding fragment thereof that binds to a polypeptide or complex thereof at a second location in the biological sample; and e) detecting an optical signal associated with the detectably labelled antibody, thereby detecting the polypeptide or complex thereof at the second location in the biological sample. In some embodiments, the detectably labelled antibody comprises a fluorophore. In some embodiments, the detectably labelled antibody comprises a reporter oligonucleotide. In some embodiments, the optical signal associated with the detectably labelled antibody is detected using a detectable probe that directly or indirectly binds to the reporter oligonucleotide.

Provided herein is a method for sample analysis which includes contacting a biological sample with a catalyst that catalyzes de-crosslinking of molecular crosslinks in the biological sample, wherein the biological sample is a sectioned formaldehyde-fixed cell or tissue sample immobilized on a substrate before contacting with the catalyst; contacting the biological sample with a detectable probe that directly or indirectly binds to an RNA analyte at a first location in the biological sample; detecting an optical signal associated with the detectable probe, thereby detecting the RNA analyte at the first location in the biological sample; contacting the biological sample with a detectably labelled antibody or an epitope binding fragment thereof that binds to a polypeptide or complex thereof at a second location in the biological sample; and detecting an optical signal associated with the detectably labelled antibody, thereby detecting the polypeptide or complex thereof at the second location in the biological sample. In some instances, the optical signals are detected by imaging the biological sample on the substrate. In some embodiments, the catalyst comprises

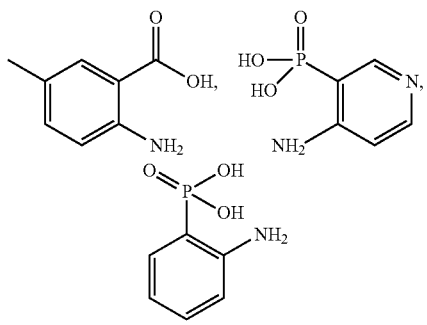

or a salt, zwitterion, or solvate thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings illustrate certain features and advantages of this disclosure. These embodiments are not intended to limit the scope of the appended claims in any manner.

FIG. 2A shows formaldehyde fixation affords stable, inert crosslinks between amine residues (e.g., aminal bond, $CH_2$-linked amine). FIG. 2B depicts an example of catalytic reversal of aminal crosslinks using a combination of acid catalysis and nucleophilic catalysis.

FIG. 3A depicts structures of an exemplary catalyst. In some aspects, with varying R groups, the $pK_{a2}$ does not change significantly but the nucleophilicity (N) of $-NH_2$ does. FIG. 3B depicts structures of an exemplary catalyst under different pH and examples of pH-dependent acid catalysis. In this example, both compound A and compound B exist in solution at pH 6.8, but only compound B with $-COOH$ catalyzes de-crosslinking reaction. However, at pH 9, the compound exists mostly as a deprotonated form (compound A), which does not catalyze the de-crosslinking reaction. FIG. 3C depicts exemplary phosphonic acid catalysts which perform well at pH 6.8 since $-OH$ of the phosphonic acid exists in solution to catalyze a de-crosslinking reaction.

DETAILED DESCRIPTION

Figure 1:
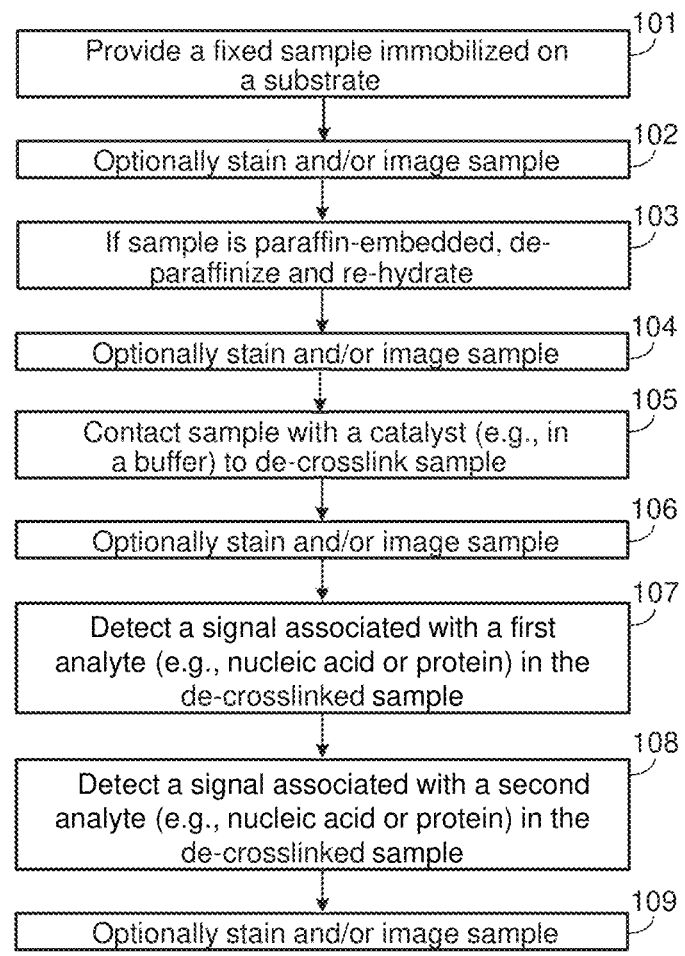
FIG. 1 depicts the workflow of an exemplary method disclosed herein.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Compositions and methods are needed for analyzing the spatial localization of analytes in a biological sample, such as various archived tissue materials comprising molecular crosslinks. Formalin/formaldehyde fixation is a dominant method for storage of primary tissue samples for pathology and life science research due to its robustness in maintaining tissue architectures at even ambient temperatures. However, most methods of analyte detection are not compatible with fixed tissues without specific sample preparation to clear crosslinking and render analytes accessible to biochemical reactions, including those amenable to signal detection and/or amplification. Antigen retrieval is commonly employed using a combination of heat, temperature, buffer, and sometimes pressure to expose antigens for more effective antibody staining, and proteinase digestion or other forms of de-crosslinking are employed to enable effective nucleic acid detection.

In some embodiments, provided herein are compositions and methods that involve catalytic de-crosslinking for preparing samples, such as FFPE cell and tissue samples. In some embodiments, a sample such as an otherwise inaccessible fixed or FFPE sample can be treated with a buffer comprising a catalyst or a precursor thereof to provide accessibility of target analyte molecules in the sample for in situ analysis. In some embodiments, a sample such as an FFPE sample can be de-paraffinized. In some embodiments, the de-paraffinized sample can be contacted with a buffer (e.g., a citrate buffer) comprising an effective concentration of a catalyst or a precursor thereof for a period of time. In some embodiments, the sample can be incubated in a buffer together with the catalyst, e.g., a heated buffer. In some embodiments, the buffer can have antigen retrieving effect. In some embodiments, the buffer can facilitate and/or promote catalytic de-crosslinking by the catalyst. In some embodiments, antigen retrieving due to catalytic de-crosslinking can be combined with heating the sample and/or the buffer (e.g., in a thermocycler), and/or be combined with an antigen retrieving effect of the buffer. In some embodiments, the sample can be washed using a buffer, such as a heated antigen retriever buffer or another buffer to remove products of the de-crosslinking reaction. After the de-crosslinking incubation and/or the de-crosslinking wash, the sample can be subjected to probe/antibody binding and downstream imaging and analysis.

In some embodiments, provided herein are various catalysts, buffer compositions comprising one or more catalysts, combinations of one or more catalysts with one or more other de-crosslinking agents including enzymes/proteases, and/or compositions comprising crowding agents (e.g., PEG20k MW, to mitigate potential RNA loss during de-crosslinking). In some embodiments, provided herein are methods involving catalytic de-crosslinking using any one or more of the compositions disclosed herein. In some embodiments, provided herein are methods involving catalytic de-crosslinking for various time periods and/or at various temperatures, optionally with heating and/or one or more post-de-crosslinking washes. In some embodiments, the temperature of the sample can be adjusted as needed prior to, during, and/or after de-crosslinking, for example, by controlling the rate of thermocycler heating up/down.

In some embodiments, the methods can optionally include staining and/or imaging of the fixed biological sample (e.g., tissue section), of the de-crosslinked biological sample (e.g., tissue section), or both. A stain can be any appropriate stain, such as a histological stain (e.g., hematoxylin and eosin) or an immunological stain (e.g., an immunofluorescent stain), or any other stain described herein, e.g., in Section IV-(v). Staining (e.g., H&E staining) and/or imaging can be performed before and/or after the de-crosslinked biological sample (e.g., tissue section) is contacted with one or more nucleic acid probes and/or labelling agents (e.g., fluorescently labelled antibodies) and signals associated with the nucleic acid probes and/or labelling agents are detected in the sample.

FIG. 1 shows an exemplary method where a fixed sample immobilized on a substrate is provided in step 101, and the sample can be optionally stained and/or imaged in step 102. If the sample is paraffin-embedded, a de-paraffinization and re-hydration step can be performed in step 103 to prepare the sample for catalytic de-crosslinking. The sample can again be optionally stained and/or imaged in step 104 prior to de-crosslinking in a buffer comprising a catalyst disclosed herein in step 105. The sample can be optionally stained and/or imaged after catalytic de-crosslinking in step 106. A signal associated with a first analyte (e.g., nucleic acid or protein) in the de-crosslinked sample can be detected in step 107, for instance, signals associated with the first analyte can be detected in sequential cycles using detection reagents (e.g., nucleic acid probes). A signal associated with a first analyte (e.g., nucleic acid or protein) in the de-crosslinked sample can be detected in step 108, and in some examples, the first analyte can be a cellular nucleic acid (e.g., genomic DNA, mRNA, or cDNA) and the second analyte can be a protein. The sample can be optionally stained and/or imaged after analyte detection in step 109.

Figure 5B:
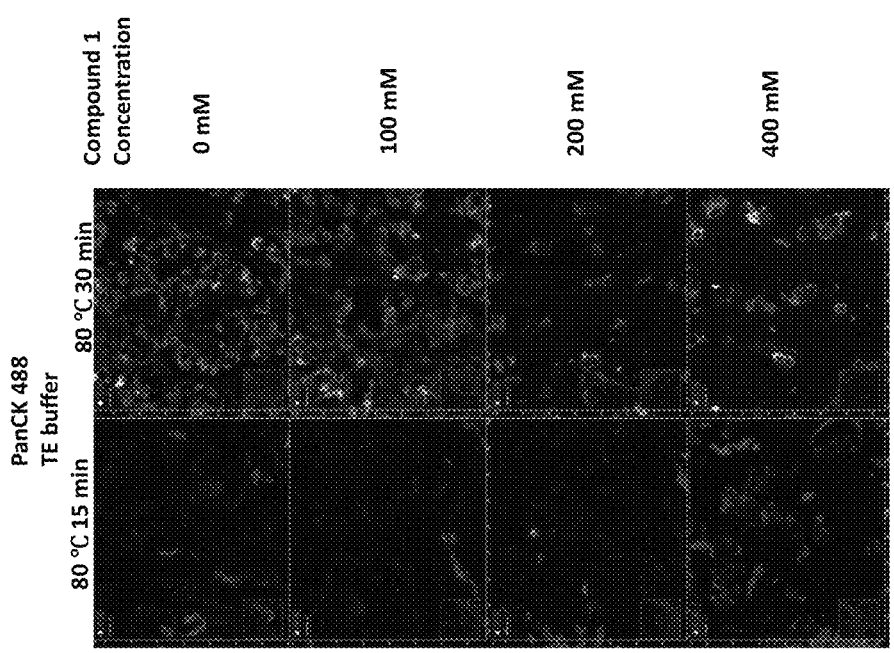
FIGS. 5A-5B show representative images of anti-panCK antibody staining in FFPE human breast cancer samples catalytically de-crosslinked in citrate buffer (FIG. 5A) or TE buffer (FIG. 5B), compared to a control sample de-crosslinked using a steamer.
Figure 5A:
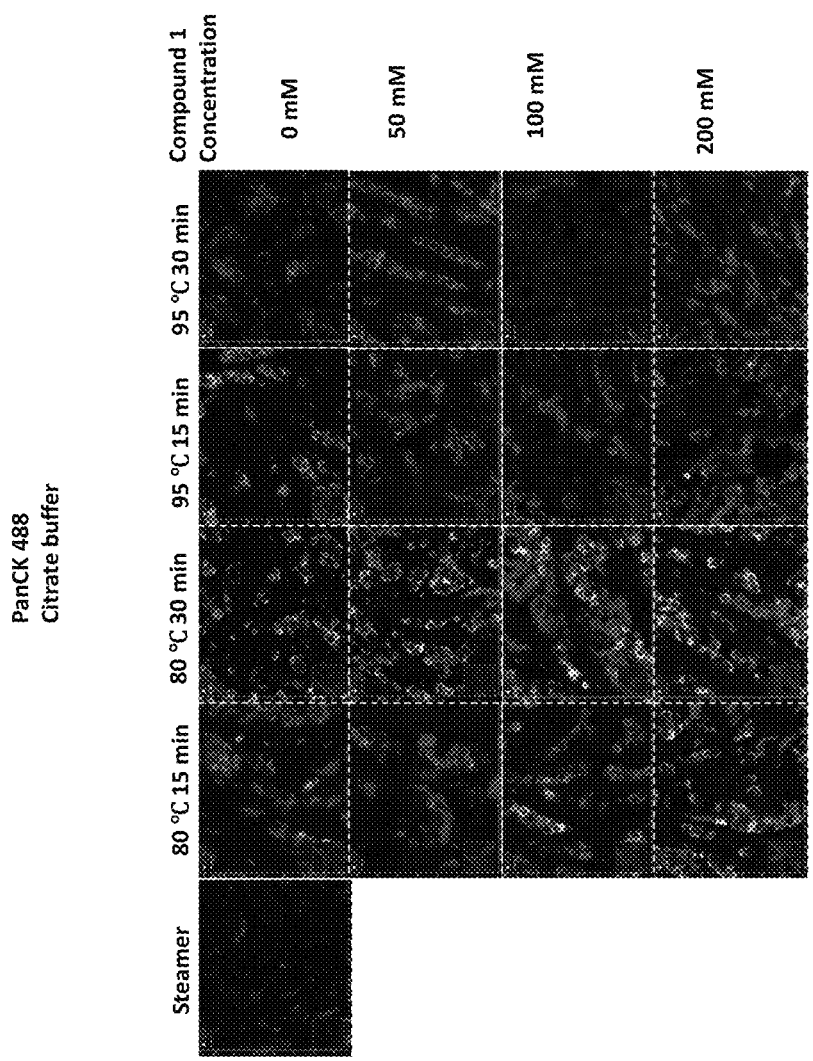
Figure 6:
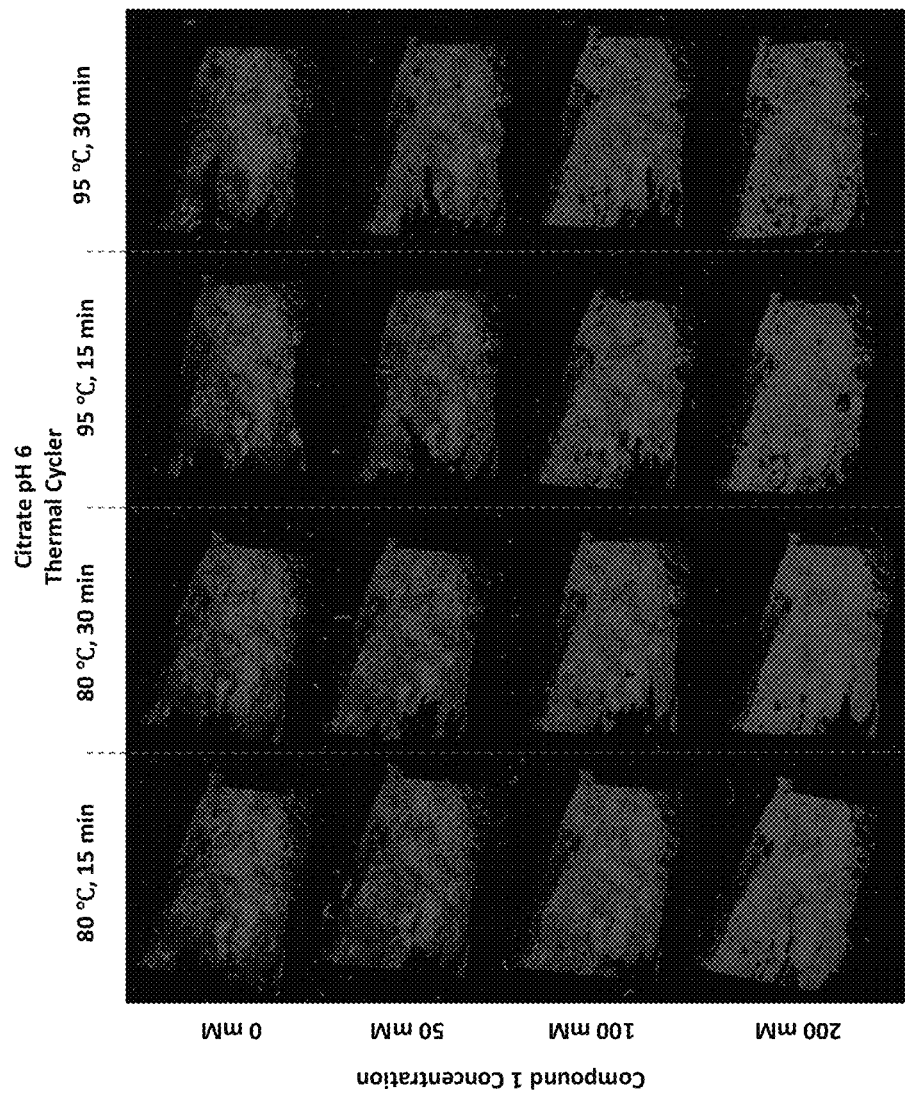
FIG. 6 shows representative DPAI images of the de-crosslinked FFPE human breast cancer samples.

Catalytic de-crosslinking disclosed herein can improve detection of signals associated with nucleic acid analytes and/or non-nucleic acid analytes (e.g., protein analytes) in a fixed biological sample immobilized on a substrate (for instance, as demonstrated in FIG. 4, FIGS. 5A-5B, FIGS. 7A-7C, FIG. 8, and FIG. 9) while substantially maintaining or improving sample integrity and/or adhesion to the substrate (for instance, as shown in FIG. 6), as compared to sample de-crosslinking without using the catalyst (e.g., using heating in a steamer). As such, signals associated with the analytes at multiple locations in the catalytically de-crosslinked sample can be detected more efficiently (e.g., more signals can be detected in a given sample) and more accurately (e.g., with higher signal-to-noise ratios). For example, detection of signals associated with analytes can be probed and detected (as described in Section III) in a catalytically de-crosslinked sample (e.g., as described in Section II).

II. Catalytic De-Crosslinking

In some embodiments, provided herein are methods and compositions for providing a fixed biological sample immobilized on a substrate, and for catalytically de-crosslinking molecular crosslinks in the fixed biological sample. In some embodiments, a method disclosed herein comprises contacting a fixed biological sample with a composition comprising a catalyst or a precursor thereof.

A. Fixed Biological Samples

A biological sample disclosed herein can include any sample comprising a cell, a tissue, or a derivative of a cell or a tissue. In some embodiments, a biological sample herein includes a fixed cell or tissue sample comprising molecular crosslinks that can be catalytically de-crosslinked using a catalyst disclosed herein. The ability to use a fixed biological sample in an analytical method, such as in situ analysis of biological molecules (e.g., genomic DNA, RNA, cDNA, and/or proteins), is enhanced if the cross-links established during fixation of the biological sample are reversed so that an assay can be carried out before sample degradation occurs. In some aspects, data obtained from a de-crosslinked biological sample are similar to that obtained from a fresh sample (e.g., a sample that is not fixed and/or crosslinked).

A fixed biological sample can be any appropriate fixed biological sample. In some embodiments, a fixed biological sample can be a fixed tissue sample (e.g., a fixed tissue section). In some embodiments, a sample herein is not and does not comprise a dissociated tissue/cell suspension. Molecules (e.g., analytes, labelling agents, nucleic acid probes, etc., or products generated in situ in the sample) may but do not need to be removed from a sample herein for analysis before, during, or after catalytic de-crosslinking of the sample. In some embodiments, molecules (e.g., analytes, labelling agents, nucleic acid probes, etc.) are not removed from a sample herein for analysis. In some embodiments, signals associated with the molecules (e.g., analytes, labelling agents, nucleic acid probes, etc., or products generated in situ in the sample) are detected at multiple locations in the catalytically de-crosslinked sample, e.g., the signals can be detected in situ in a catalytically de-crosslinked tissue section.

In some embodiments, the biological sample is fixed and the fixation comprises contacting the sample with one or more agents that react with one another and/or with molecules in the biological sample. In some embodiments, the reaction creates molecular crosslinks between molecules of the one or more agents, between molecules in the biological sample, and/or between molecules of the one or more agents and molecules in the biological sample. In some embodiments, the one or more agents are crosslinking agents, and the molecular crosslinks are products of one or more reactions between a crosslinking agent and a molecule in the biological sample.

In some embodiments, a biological sample is fixed using one or more crosslinking agents comprising an aldehyde. In some embodiments, an aldehyde includes a compound containing one or more aldehyde (—CHO) groups, where the aldehyde groups are capable of reacting with an amine (e.g., a primary amine, a secondary amine, or a tertiary amine) or with an amide. Amines are derivatives of ammonia, wherein one or more hydrogen atoms in amines have been replaced by a substituent such as an alkyl or aryl group. These may respectively be called alkylamines and arylamines, and amines in which both types of substituent are attached to one nitrogen atom may be called alkylarylamines. Exemplary amines include amino acids (including amino acid residues of a protein having side chains that can react with an aldehyde), biogenic amines, trimethylamine, and aniline. In some embodiments, molecular crosslinks in a fixed sample are formed via condensation between an aldehyde and an amine, and in some aspects, the condensation does not require heating and/or an acidic condition. Amides having the structure R—CO—NR'R" in which a nitrogen atom is attached to a carbonyl group. In some embodiments, molecular crosslinks in a fixed sample are formed via condensation between an aldehyde and an amide, e.g., under heating and/or acidic conditions. Exemplary aldehydes can include formaldehyde, paraformaldehyde, glutaraldehyde, glyoxal, and the like.

In some embodiments, fixing a biological sample comprises treating the sample with a crosslinking agent. In some embodiments, the crosslinking agent comprises formaldehyde. Paraformaldehyde (PFA) is a polymer of formaldehyde. While paraformaldehyde itself is not a fixing agent, it can be heated and/or treated under basic conditions until it becomes solubilized and broken down to formaldehyde molecules.

In some embodiments, the molecular crosslinks are on RNA, DNA, protein, carbohydrate, lipid, and/or other molecules in the biological sample. In some embodiments, the molecular crosslinks comprise one or more aminal crosslinks such as aminal bridges. In some embodiments, a fixed biological sample can comprise aminal crosslinks among nucleic acids (e.g., genomic DNA, RNA such as mRNA, and/or cDNA), proteins, carbohydrates, lipids, and/or other molecules in the biological sample. Aminal crosslinks can be made, for example, by fixing a sample with formaldehyde.

In some embodiments, the fixative or fixation agent is formaldehyde. Formaldehyde as fixative comprises paraformaldehyde (or "PFA") and formalin, both of which relate to the formaldehyde composition (e.g., formalin is a mixture of formaldehyde and methanol). Thus, a formaldehyde-fixed biological sample may be formalin-fixed or PFA-fixed. Any suitable protocols and methods for the use of formaldehyde as a fixation reagent to prepare fixed biological samples can be used in the methods and compositions of the present disclosure. In some embodiments, a biological sample is a formalin-fixed, paraffin-embedded (FFPE) tissue sample (e.g., an FFPE tissue section).

In some embodiments, aldehyde fixation methods can be combined with other tissue preservation methods. For example, aldehyde fixation can be combined with fresh frozen preservation of tissues, e.g., fresh frozen tissues can be fixed using an aldehyde. Aldehyde fixation can also be combined with alcohol fixation, or with any number of commercially available fixation/preservation techniques.

For example, aldehyde fixation can be combined with salt-rich buffer solutions such as RNAlater™, low-temperature preservation buffers such as HypoThermosol, alcohol-PEG fixation (e.g., Neo-Rix, STATFIX, PAGA, UMFIX), PAX-Gene, Allprotect/Xprotect, CellCover, RN Assist, and/or zinc buffers.

In some embodiments, preparing fixed (e.g., aldehyde-fixed) biological samples for in situ analysis may comprise catalytic de-crosslinking disclosed herein in combination with additional sample processing steps and/or conditions before, during, and/or after catalytic de-crosslinking. Exemplary sample processing steps and/or conditions may include longer permeabilization periods, additional permeabilization reagents, or higher permeabilization reagent concentrations, e.g., compared to samples that are not fixed, in order to allow detection reagents (e.g., nucleic acid probes and/or antibodies or epitope-binding fragments thereof) to bind to analytes in the sample.

In some embodiments, provided herein are methods of de-crosslinking aminal crosslinks in a fixed biological sample. In some embodiments, provided herein are methods of in situ analysis using such a de-crosslinked sample. The methods described herein are not limited to any particular fixation reagent that results in crosslinks (e.g., aminal crosslinks) and are equally amenable with any fixation method that results in intra-tissue crosslinking events (e.g., aminal intra tissue crosslinking events).

Figure 2A:
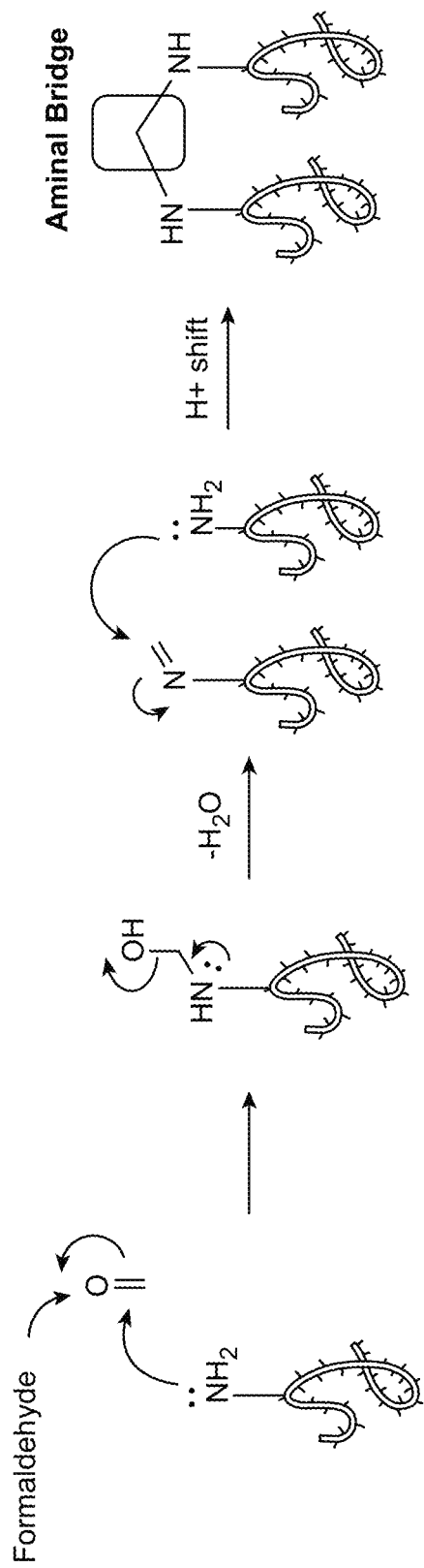
FIGS. 2A-2B depict exemplary reactions of fixation chemistry and reversal of molecular crosslinks.

In an exemplary fixation method, as shown in FIG. 2A, condensation of an amino group on a first molecule (e.g., nucleic acid or protein) in a sample with formaldehyde can afford a reactive imine, which can react with a proximal amine (e.g., a $CH_2$-linked amine on a second molecule of the same or different species as the first molecule) to form an aminal bridge, thereby fixing the sample. While fixing can help stabilize the sample, molecular crosslinks could lead to antigen masking and/or background autofluorescence in the sample. For example, PFA induced crosslinks are known to be responsible for increased autofluorescence in FFPE tissues. In some cases, molecular crosslinks may block or restrict biochemical reactions such as nucleic acid hybridization or methods of signal amplification utilized for analyte detection. Conventional methods for antigen retrieval may not sufficiently retrieve the masked antigens and may not remove or reduce the background autofluorescence due to fixing. The catalytic de-crosslinking methods disclosed herein address these and other issues with conventional methods. In some aspects, catalytic de-crosslinking provided herein may revert these molecular crosslinks into native amines and thereby reduce the autofluorescence in the sample for in situ assay workflows (e.g., imaging and detecting signals). In some cases, conventional antigen retrieval methods break these crosslinks but do not revert them into native amines and may not be effective as the catalytic de-crosslinking described herein.

B. Preparing Samples for Catalytic De-Crosslinking

A biological sample can be immobilized on a substrate before, during, and/or after contacting with the catalyst. In some embodiments, the biological sample is immobilized on the substrate before contacting with the catalyst. In some embodiments, the biological sample remains immobilized on the substrate during and after contacting with the catalyst. In some embodiments, the biological sample is immobilized on the substrate after contacting with the catalyst. In some embodiments, the biological sample is immobilized on the substrate during contacting with the catalyst. In some embodiments, a biological sample can be provided in a fixed state. In some embodiments, a fixed biological sample can undergo one or more preparation steps before it is pretreated and/or de-crosslinked.

In some embodiments, the substrate comprises a planar surface configured to contact the biological sample and does not comprises a bead, particle, or microwell, optionally wherein the substrate is a glass slide or a plastic slide. In some embodiments, the substrate is transparent. In some embodiments, the substrate is suitable for imaging using fluorescent microscopy, for instance, for in situ analyte detection, e.g., in situ sequencing or in situ sequential hybridization. In some embodiments, the substrate does not comprises nucleic acid immobilized thereon prior to contacting the biological sample. In some embodiments, the biological sample is a tissue section. In some embodiments, the biological sample comprise cells immobilized on the substrate. In some embodiments, the cells are dissociated cells, cultured cells, and/or cells isolated from a subject. In some embodiments, the biological sample is an aldehyde-fixed biological sample. In some embodiments, the biological sample is a formaldehyde-fixed biological sample. In some embodiments, the biological sample is a paraffinized biological sample. In some embodiments, the biological sample is a formaldehyde-fixed paraffin-embedded (FFPE) biological sample. In some embodiments, the biological sample is a fresh frozen biological sample that has been crosslinked.

In some embodiments, prior to contacting the biological sample with the catalyst, the method comprises a step of pre-warming the biological sample. In some embodiments, a fixed biological sample (e.g., an FFPE tissue section) can be pre-warmed to between about 20° C. and about 60° C., e.g., about 30° C. to about 50° C., about 35° C. to about 45° C., or about 40° C. to about 43° C. In some embodiments, the fixed biological sample can be pre-warmed by incubation in a water bath. In some embodiments, the fixed biological sample is a block of embedded tissue (e.g., formalin fixed and paraffin embedded) that can be sliced using a microtome to generate embedded tissue sections, e.g., about 5 μm in thickness. In some embodiments, the microtome can be pre-warmed to between about 40° C. and about 43° C. for slicing the fixed biological sample.

In some embodiments, prior to contacting the biological sample with the catalyst, the method comprises a step of dehydrating the biological sample. In some such embodiments, the fixed biological is dehydrated by drying at a temperature higher than room temperature, e.g., at about 20° C. to about 60° C., about 30° C. to about 50° C., about 35° C. to about 45° C., or about 40° C. to about 43° C., such as at about 40° C., 41° C., 42° C., 43° C., 44° C., or 45° C., for a period of time (e.g., about 30 minutes to about 6 hours, about 1 hour to about 5 hours, about 2 hours to about 4 hours, or about 3 hours). In some such embodiments, the fixed biological is dried at room temperature for a period of time (e.g., about 2 hours to about 24 hours, about 5 hour to about 20 hours, about 8 hours to about 16 hours, or overnight), for example, in a desiccator. In some such embodiments, the fixed biological is dried at a temperature higher than room temperature, followed by drying at room temperature.

In some embodiments, the method comprises, prior to contacting the biological sample with the catalyst, a step of baking the biological sample. In some such embodiments, the fixed biological is baked at a temperature, e.g., at about 40° C. to about 80° C., about 45° C. to about 75° C., about 50° C. to about 70° C., or about 55° C. to about 65° C., such as at about 56° C., 58° C., 60° C., 62° C., or 64° C., for a period of time (e.g., about 30 minutes to about 6 hours, about 1 hour to about 5 hours, about 1.5 hours to about 3 hours, or about 2 hours). In some such embodiments, the fixed biological is baked uncovered in an oven. In some such embodiments, the baked fixed biological is calibrated to room temperature for a period of time (e.g., about 3 minutes to about 30 minutes, about 5 minutes to about 20 minutes, or about 7 minutes).

In some such embodiments, for paraffin-embedded biological samples (e.g., FFPE samples), the sample can be de-paraffinized (e.g., to produce a de-paraffinized fixed biological sample) and re-hydrated. In some embodiments, de-paraffinizing comprises contacting the biological sample with xylene, ethanol, and water, or, sequentially contacting the biological sample with xylene and an alcohol (e.g., ethanol) series such as absolute ethanol, about 96% ethanol, and about 70% ethanol. In some embodiments, de-paraffinizing can include treating with xylene and ethanol (e.g., absolute ethanol, about 96% ethanol, and or about 70% ethanol). In some embodiments, de-paraffinization can include, sequentially, treating with xylene (e.g., once, twice, or more times, each for about 5 minutes to about 15 minutes, such as about 10 minutes each), treating with absolute ethanol (e.g., once, twice, or more times, each for about 1 minute to about 10 minutes, such as about 2 minute to about 5 minutes, e.g., about 3 minutes each), treating with about 96% ethanol (e.g., once, twice, or more times, each for about 1 minute to about 10 minutes, such as about 2 minute to about 5 minutes, e.g., about 3 minutes each), and treating with about 70% ethanol (e.g., once, twice, or more times, each for about 1 minute to about 10 minutes, such as about 2 minute to about 5 minutes, e.g., about 3 minutes each). In some embodiments, the sample can be treated with water for re-hydration (e.g., in nuclease free water (e.g., DEPC water)), e.g., once, twice, or more times, each for about 5 seconds to about 1 minute, such as 10 seconds to about 30 seconds, e.g., about 20 seconds each.

In some embodiments, a fixed biological sample is pretreated with one or more pretreating reagents prior to delivery or application of a de-crosslinking agent (e.g., a catalyst disclosed herein). Pretreatment can include permeabilization of the biological sample, for example, using conditions milder than those typically used for extracting analytes.

In some embodiments, a pretreating reagent can include a proteinase (e.g., collagenase). The proteinase can be present in any appropriate concentration (e.g., about 0.005 to about 0.5 U/μL (e.g., about 0.01 to about 0.5 U/μL, about 0.05 to about 0.5 U/μL, about 0.1 to about 0.5 U/μL, about 0.1 to about 0.3 U/μL, or about 0.2 U/μL). In some embodiments, a proteinase can be pepsin, Proteinase K, or an ArcticZymes Proteinase (an unspecific endopeptidase that can be inactivated after use). The proteinase can optionally be applied with a buffer, such as Hank's Balanced Salt Solution (HBSS) buffer. In some embodiments, if pepsin is used for permeabilization, a pretreating reagent can include a proteinase (e.g., a second proteinase or a proteinase other than pepsin). In some embodiments, if Proteinase K is used for permeabilization, a pretreating reagent may but does not need to include a proteinase.

In some embodiments, a pretreating reagent can include a detergent. The detergent can be present in any appropriate concentration (e.g., about 0.05% to about 2% (v/v), about 0.1% to about 1% (v/v), about 0.1% (v/v), or about 0.5% (v/v)). In some embodiments, the detergent is a non-ionic detergent. In some embodiments, the detergent comprises TRITON™ X-100. In some embodiments, the detergent is in a buffer. In some embodiments, the buffer comprises, for example, tris(hydroxymethyl)aminomethane-Ethylenediaminetetraacetic acid (TE), phosphate-buffered saline (PBS), 2-[4-(2-hydroxyethyl)piperazin-1-yl]ethanesulfonic acid (HEPES), and/or 2-(N-morpholino)ethanesulfonic acid (MES), with a pH of about 7.0 to about 9.0 (e.g., about 7.5 to about 8.5, or about 8.0).

A pretreating reagent can be applied to the biological sample (e.g., a cell or tissue sample such as a tissue section) in any number of ways. In some embodiments, a pretreating reagent is in solution or suspension. In some embodiments, the biological sample can be soaked in a solution or suspension comprising a pretreating reagent. In some embodiments, a pretreating reagent is sprayed onto the biological sample. In some embodiments, a pretreating reagent is supplied to the biological sample via a microfluidic system (e.g., as a solution or suspension). In some embodiments, the biological sample is dipped into a solution or suspension of a pretreating reagent, wherein excess solution or suspension is removed from the biological sample. In some embodiments, a pretreating reagent is delivered to the biological sample via a hydrogel, wherein the hydrogel is a repository for a pretreatment reagent and is contacted with the biological sample.

The pretreatment can be applied to the biological sample (e.g., a cell or tissue sample such as a tissue section) for a time sufficient to permeabilize a biological sample to facilitate the de-crosslinking agent (e.g., a catalyst disclosed herein) penetrating the biological sample. In some embodiments, the pretreatment can be applied to the biological sample for between about 1 minute and about 60 minutes. In some embodiments, the pretreatment can be applied to the biological sample between about 1 minute and about 55 minutes, about 1 minute and about 50 minutes, about 1 minute and about 45 minutes, about 1 minute and about 40 minutes, about 1 minute and about 35 minutes, about 1 minute and about 30 minutes, about 1 minute and about 25 minutes, about 1 minute and about 20 minutes, about 5 minutes and about 60 minutes, about 10 minutes and about 60 minutes, about 10 minutes and about 50 minutes, about 10 minutes and about 40 minutes, or about 10 minutes and about 30 minutes. In some embodiments, the pretreatment can be applied to the biological sample for about 20 minutes.

The biological sample (e.g., a cell or tissue sample such as a tissue section) can be incubated during pretreatment. In some embodiments, the biological sample can be incubated between about 30° C. and about 45° C. during pretreatment. In some embodiments, the biological sample can be at about 31° C., 32° C., 33° C., 34° C., 35° C., 36° C., 37° C., 38° C., 39° C., 40° C., 41° C., 42° C., 43° C., 44° C., or 45° C. during pretreatment. In some embodiments, the biological sample can be incubated at about 37° C. during pretreatment.

In some embodiments, after drying, baking, de-paraffinization, and/or re-hydration, a fixed biological sample is not pretreated with one or more pretreating reagents and prior to delivery or application of a de-crosslinking agent (e.g., a catalyst disclosed herein) to the biological sample. In some embodiments, a de-paraffinized and re-hydrated biological is not pretreated by permeabilizing the sample (e.g., using a protease or detergent) prior to contacting the sample with a de-crosslinking agent.

In some embodiments, the method comprises, prior to or after contacting the biological sample with a de-crosslinking agent (e.g., a catalyst disclosed herein), a step of staining the biological sample and/or imaging the stained biological sample, optionally wherein the staining comprises the use of a histological stain and/or an immunological stain. A stain can be any appropriate stain, such as a histological stain (e.g., hematoxylin and eosin, H&E) or an immunological stain (e.g., an immunofluorescent stain), or any other stain described herein. In some embodiments, a stain may include an agent that interacts with an analyte (e.g., an endogenous analyte in a sample) indicative of cell features may include an agent that interacts with an analyte (e.g., an endogenous analyte in a sample) indicative of morphological features and/or cell features, and the analyte may include intracellular analytes, such as proteins, protein modifications (e.g., phosphorylation status or other post-translational modifications), nuclear proteins, cellular membrane proteins, nuclear membrane proteins, or any combination thereof. In some instances, the stain is a nucleic acid stain, an extracellular matrix stain, a cellular membrane stain, a nuclear membrane stain, a cytological stain, and/or any combinations thereof.

Staining and/or imaging can be carried out before, during, and/or after the fixed biological sample (e.g., a fixed tissue section) is de-crosslinked using a de-crosslinking agent (e.g., a catalyst disclosed herein). In some embodiments, staining and/or imaging of the sample after de-crosslinking can be performed and the results can be compared to those before de-crosslinking. Images of the sample can be used to monitor cell or tissue morphology and/or sample detachment during sample processing, including drying, baking, deparaffinization, re-hydration, and/or de-crosslinking, as well as washing and/or permeabilization after de-crosslinking.

C. De-Crosslinking Agents and Catalytic De-Crosslinking

Conditions for reversing the effects of fixing a biological sample tend to be harsh. See e.g., U.S. Pat. No. 7,919,280; US 2005/0014203; US 2009/0202998A1; Masuda et al., "Analysis of chemical modification of RNA from formalin-fixed samples and optimization of molecular biology applications for such samples," Nucleic Acids Research 27(22): 4436-4443, (1999); Evers et al., "The effect of formaldehyde fixation on RNA: optimization of formaldehyde adduct removal," Journal of Molecular Diagnostics 13(3): 282-288, (2011); and Beechem, "High-Plex spatially resolved RNA and protein detection using digital spatial profiling: A technology designed for immuno-oncology biomarker discovery and translational research," Biomarkers for Immunotherapy of Cancer. Humana, New York, NY, 2020. 563-583, each of which is incorporated by reference herein in its entirety. For example, treatment of PFA-treated tissue samples can include heating to 60° C. to 70° C. in Tris buffer for several hours, and yet typically this removes only a fraction of the fixative-induced crosslinks. In another example, a 3.0% PFA-fixed tissue samples were soaked in 20 mM Tris-HCl (pH 9.0) and then incubated for 2 h at 60° C. for de-crosslinking (Nagaki et al., "De-crosslinking enables visualization of RNA-guided endonuclease—in situ labelling signals for DNA sequences in plant tissues," Journal of Experimental Botany, 71(6):1792-1800, (2020)). The harsh de-crosslinking treatment conditions can result in permanent damage to biomolecules (e.g., nucleic acid analytes and/or protein analytes, such as those described herein) in the sample.

In some embodiments, a de-crosslinking agent or un-fixing agent herein can be a compound or composition that reverses fixation and/or removes the crosslinks within or between biomolecules (e.g., analytes for analytical methods, such as those described herein) in a sample caused by previous use of a fixation reagent. In some embodiments, de-crosslinking agents are compounds that act catalytically in removing crosslinks in a fixed sample. In some embodiments, de-crosslinking agents are compounds that act catalytically in removing aminal crosslinks in a fixed sample. In some embodiments, de-crosslinking agents can act on biological samples fixed with an aldehyde (e.g., formaldehyde), an N-hydroxysuccinimide (NHS) ester, an imidoester, or a combination thereof.

In some embodiments, provided herein are catalysts that catalyze de-crosslinking of inter-molecular crosslinks and/or intra-molecular crosslinks in the biological sample. In some embodiments, provided herein are catalysts that catalyze the cleavage of aminal bridges, thereby de-crosslinking the inter-molecular crosslinks and/or intra-molecular crosslinks.

In some embodiments, the catalyst is a water-soluble catalyst. In some embodiments, the catalyst is an organic molecule. In some embodiments, the catalyst is a transimination catalyst. In some embodiments, the catalyst is a bifunctional transimination catalyst that accelerates hydrazone and oxime formation. In some embodiments, the catalyst catalyzes de-crosslinking of aminal crosslinks in the biological sample. In some embodiments, the catalyst catalyzes breakdown of hemi-aminal adducts and/or aminal adducts in the biological sample.

Figure 2B:
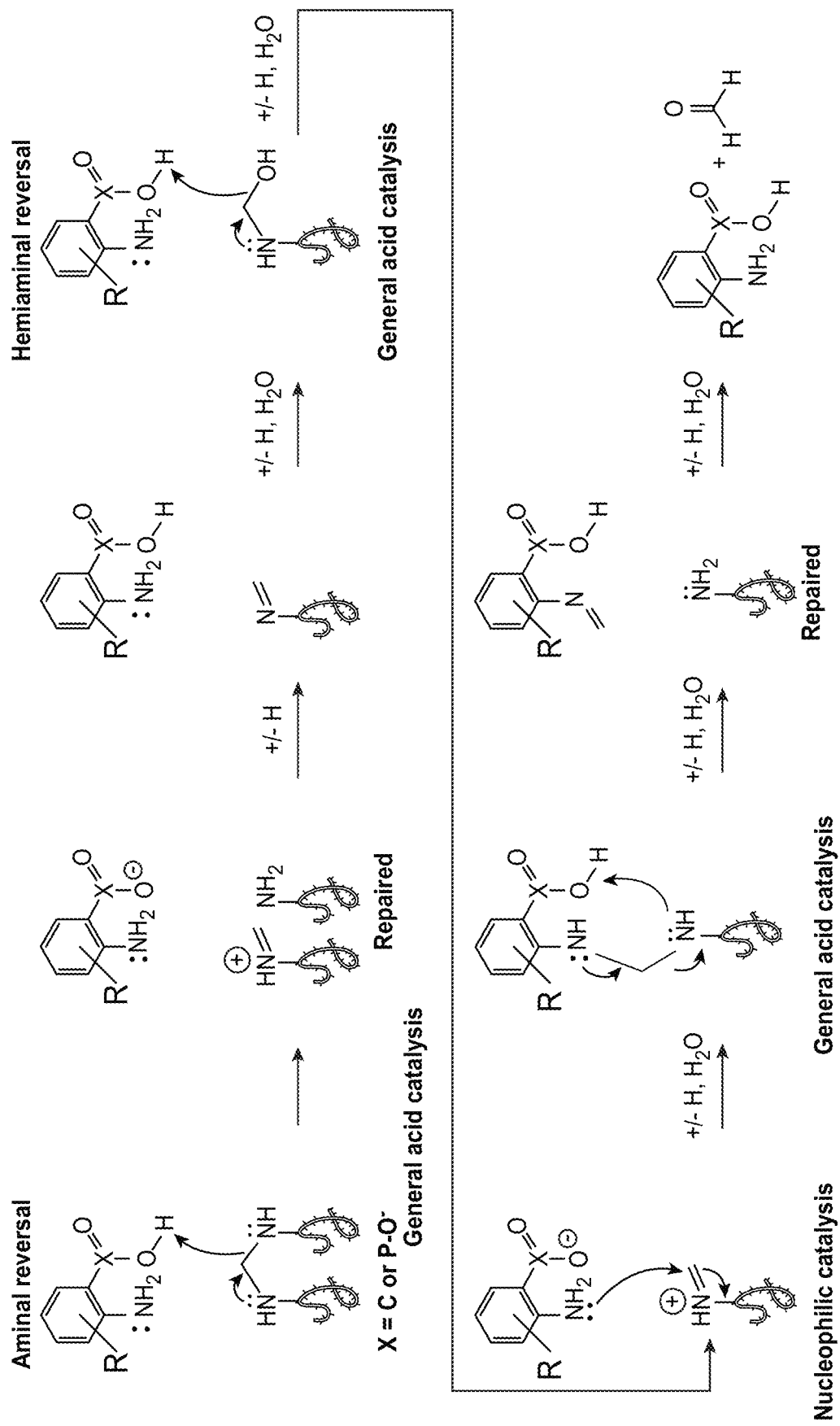

Aminal crosslinks (e.g., aminal bridges) can be catalytically reversed using one or more organocatalyst. In some embodiments, in catalytic reversal of aminal crosslinks, a first C—N bond of the aminal bridge can be broken in an acid-base reaction, and the second C—N bond of the aminal can be broken to generate repaired $NH_2$ groups on the first and second molecules. FIG. 2B shows aminal crosslinks can be catalytically reversed using a combination of acid catalysis and nucleophilic catalysis.

In some embodiments, the catalyst is a compound of formula (I),

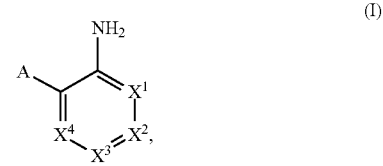

(I)

or a salt, zwitterion, or solvate thereof, wherein:
A is selected from the group consisting of —COOH, —P(=O)(OH)$_2$, and —S(=O)$_{2 0}$H;
$X^1$, $X^2$, $X^3$, and $X^4$ are each independently selected from the group consisting of: CH, CR, and N;
each occurrence of $R^a$ is independently selected from the group consisting of $C_{1-6}$ alkyl, $C_{1-6}$ haloalkyl, $C_{1-6}$ alkoxy, —NO$_2$, —NR'R", and —C(=O)NR'R"; and
each occurrence of R' and R" is independently selected from the group consisting of H and $C_{1-6}$ alkyl which is optionally substituted with

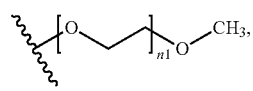

wherein n1 is an integer from 12 to 16.

In some embodiments of formula (I), it is provided that when A is —P(=O)(OH)$_2$ and $X^1$, $X^2$, and $X^4$ are CH, then $X^3$ is other than C—CH$_3$.

In some embodiments of formula (I), A is —COOH. In some embodiments of formula (I), A is —P(=O)(OH)$_2$. In some embodiments of formula (I), A is —S(=O)$_{2 0}$H.

In some embodiments of Formula (I), $X^1$ is CH. In some embodiments of Formula (I), $X^1$ is $CR^a$. In certain of these embodiments, $X^1$ is C—$CH_3$. In some embodiments of Formula (I), $X^2$ is CH. In some embodiments of Formula (I), $X^2$ is N. In some embodiments of Formula (I), $X^4$ is CH. In some embodiments of Formula (I), $X^4$ is N.

In some embodiments of Formula (I), $X^3$ is N. In some embodiments of Formula (I), $X^3$ is CH. In some embodiments of Formula (I), $X^3$ is $CR^a$. In certain of these embodiments, $R^a$ is $C_{1-6}$ alkyl (e.g., methyl). In certain embodiments, $R^a$ is $NO_2$. In certain embodiments, $R^a$ is NR'R" (e.g., $NH_2$). In certain embodiments, $R^a$ is C(=O)NR'R". As a non-limiting example of the foregoing embodiments, $R^a$ is

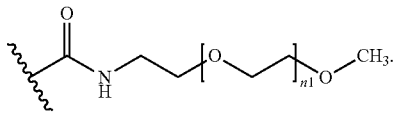

In some embodiments of Formula (I), $X^2$ and $X^4$ are CH. In some embodiments of Formula (I), $X^1$, $X^2$, and $X^4$ are CH. In certain of these embodiments, $X^3$ is $CR^a$ (e.g., C—$CH_3$). In certain other embodiments, $X^3$ is N. In certain of the foregoing embodiments (when $X^2$ and $X^4$ are CH; or when $X^1$, $X^2$, and $X^4$ are CH), A is —COOH or —P(=O)(OH)$_2$.

In some embodiments, the compound of Formula (I) is a compound of Formula (IA):

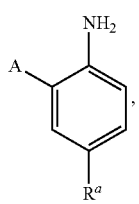

(IA)

or a salt, zwitterion, or solvate thereof.

In some embodiments of Formula (IA), A is —COOH. In some of these embodiments of Formula (IA), $R^a$ is $C_{1-6}$ alkyl. In certain of these embodiments, $R^a$ is $C_{1-3}$ alkyl. For example, in some embodiments, $R^a$ is methyl. In other of these embodiments, $R^a$ is methoxy. In other of these embodiments, $R^a$ is —$NH_2$. In other of these embodiments, $R^a$ is —N(CH$_3$)$_2$.

In some embodiments of Formula (IA), A is —P(=O)(OH)$_2$. In some embodiments of Formula (IA), $R^a$ is $C_{1-6}$ alkyl. In certain of these embodiments, R is $C_{1-3}$ alkyl. For example, in some embodiments, $R^a$ is methyl. In other of these embodiments, $R^a$ is methoxy. In other of these embodiments, $R^a$ is —$NH_2$. In other of these embodiments, $R^a$ is —N(CH$_3$)$_2$.

In some embodiments of Formula (IA), A is —S(=O)$_2$OH. In some embodiments of Formula (IA), $R^a$ is $C_{1-6}$ alkyl. In certain of these embodiments, R is $C_{1-3}$ alkyl. For example, in some embodiments, $R^a$ is methyl. In other of these embodiments, $R^a$ is methoxy. In other of these embodiments, $R^a$ is —$NH_2$. In other of these embodiments, $R^a$ is —N(CH$_3$)$_2$.

In some embodiments, the compound of Formula (I) is a compound of Formula (IB):

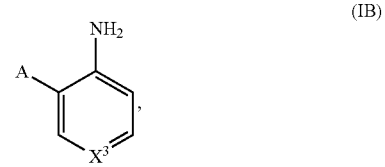

(IB)

or a salt, zwitterion, or solvate thereof, wherein: $X^3$ is CH or N.

In some embodiments of Formula (IB), A is —P(=O)(OH)$_2$. In some embodiments of Formula (IB), $X^3$ is N.

In some embodiments, the compound of Formula (I) is a compound of Formula (IC):

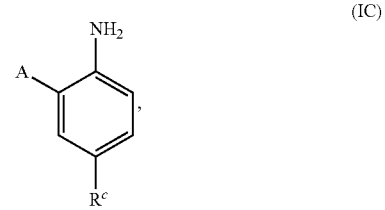

(IC)

or a salt, zwitterion, or solvate thereof, wherein RC is an electron releasing group. In some of these embodiments, the electron releasing group (RC) is selected from the group consisting of alkyl, alkoxy, hydroxy, amino, alkylamino, dialkylamino, mercapto, alkylmercapto, silyloxy, aryloxy, and alkylthio. In some of these embodiments, the electron releasing group is lower alkyl or lower alkoxy. In other of these embodiments, the electron releasing group is —$NH_2$. In still other of these embodiments, the electron releasing group is —N(CH$_3$)$_2$.

In some embodiments, the compound of Formula (I) is a compound of Formula (IC'):

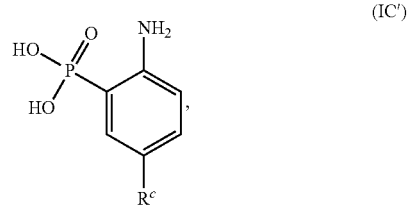

(IC')

or a salt, zwitterion, or solvate thereof, wherein RC is an electron releasing group. In some of these embodiments, the electron releasing group (RC) is selected from the group consisting of alkyl, alkoxy, hydroxy, amino, alkylamino, dialkylamino, mercapto, alkylmercapto, silyloxy, aryloxy, and alkylthio. In some of these embodiments, the electron releasing group is lower alkyl or lower alkoxy. In other of these embodiments, the electron releasing group is —$NH_2$. In still other of these embodiments, the electron releasing group is —N(CH$_3$)$_2$.

In some embodiments, the sample is contacted with a compound (e.g., in a solution or suspension) for catalytic de-crosslinking selected from the group consisting of 2-amino-5-methylbenzoic acid, 2-amino-5-nitrobenzoic acid, (2-amino-5-methylphenyl)phosphonic acid, 2-amino-5-methylbenzenesulfonic acid, 2,5-diaminobenzenesulfonic acid, 2-amino-3,5-dimethylbenzenesulfonic acid, (2-amino-5-nitrophenyl)phosphonic acid, (4-aminopyridin-3-yl)phosphonic acid, (3-aminopyridin-2-yl)phosphonic acid, (5-aminopyrimidin-4-yl)phosphonic acid, (2-amino-5-{[2-polyethoxy]ethyl}carbamoyl)phenyl)phosphonic acid, 4-aminonicotinic acid, 3-aminoisonicotinic acid, 2-aminonicotinic acid, and (2-aminophenyl)phosphonic acid. In some embodiments, the sample is contacted with Compound 1 (2-amino-5-methylbenzoic acid) in a solution or suspension for catalytic de-crosslinking. In some embodiments, the sample is contacted with Compound 8 ((4-aminopyridin-3-yl)phosphonic acid) in a solution or suspension for catalytic de-crosslinking. In some embodiments, the sample is contacted with Compound 15 ((2-aminophenyl)phosphonic acid) in a solution or suspension for catalytic de-crosslinking.

In some embodiments, the catalyst of formula (I) is selected from the group consisting of:

| Compound No. | Compound Structure |
|---|---|
| 1 | 2-amino-5-methylbenzoic acid |
| 2 | 2-amino-5-nitrobenzoic acid |
| 3 | (2-amino-5-methylphenyl)phosphonic acid |
| 4 | 2-amino-5-methylbenzenesulfonic acid |
| 5 | 2,5-diaminobenzenesulfonic acid |
| 6 | 2-amino-3,5-dimethylbenzenesulfonic acid |
| 7 | (2-amino-5-nitrophenyl)phosphonic acid |
| 8 | (4-aminopyridin-3-yl)phosphonic acid |
| 9 | (3-aminopyridin-2-yl)phosphonic acid |
| 10 | (5-aminopyrimidin-4-yl)phosphonic acid |
| 11 | (2-amino-5-{[2-polyethoxy]ethyl}carbamoyl)phenyl)phosphonic acid, n = 12–16 |
| 12 | 4-aminonicotinic acid |
| 13 | 3-aminoisonicotinic acid |
| 14 | 2-aminonicotinic acid |

| Compound No. | Compound Structure |
|---|---|
| 15 | 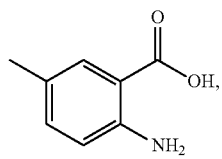 |
| 16 | 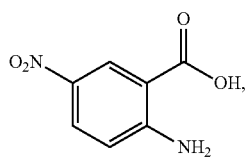 |
| 17 |  | or a salt, zwitterion, or solvate thereof.

In some embodiments, the catalyst comprises

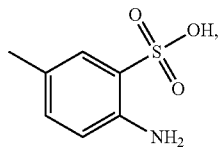

or a salt, zwitterion, or solvate thereof. In some embodiments, the catalyst comprises

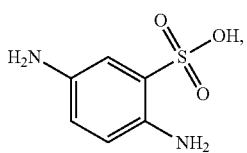

or a salt, zwitterion or solvate thereof. In some embodiments, the catalyst comprises

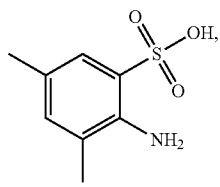

or a salt, zwitterion, or solvate thereof. In some embodiments, the catalyst comprises

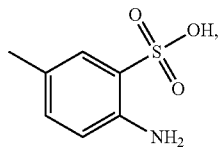

or a salt, zwitterion, or solvate thereof. In some embodiments, the catalyst comprises

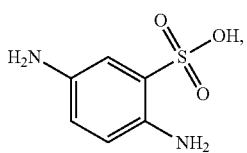

or a salt, zwitterion, or solvate thereof. In some embodiments, the catalyst comprises

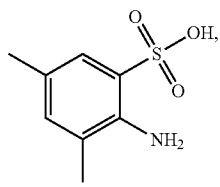

or a salt, zwitterion, or solvate thereof. In some embodiments, the catalyst comprises

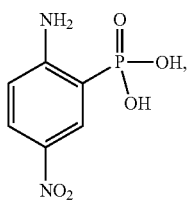

or a salt, zwitterion, or solvate thereof. In some embodiments, the catalyst comprise

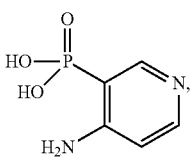

or a salt, zwitterion, or solvate thereof. In some embodiments, the catalyst comprises

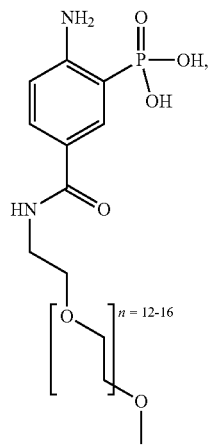

or a salt, zwitterion, or solvate thereof. In some embodiments, the catalyst comprises

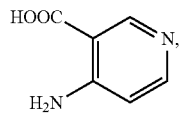

or a salt, zwitterion, or solvate thereof. In some embodiments, the catalyst comprises

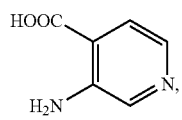

or a salt, zwitterion, or solvate thereof. In some embodiments, the catalyst comprises

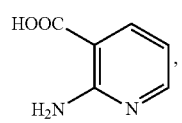

or a salt, zwitterion, or solvate thereof. In some embodiments, the catalyst comprise

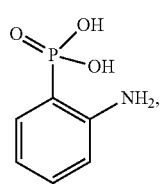

or a salt, zwitterion, or solvate, thereof. In some embodiments, the catalyst comprises

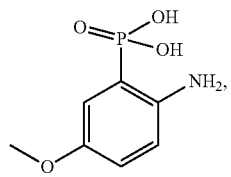

or a salt, zwitterion, or solvate thereof. In some embodiments, the catalyst comprises

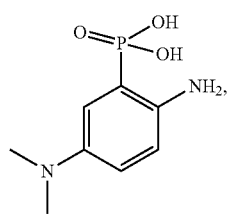

or a salt, zwitterion, or solvate thereof.

In some embodiments, a compound disclosed herein catalytically breaks down the aminal and hemi-aminal adducts that form in RNA treated with formaldehyde, and is compatible with many RNA extraction and detection conditions. Exemplary compounds include those described in Karmakar et al., "Organocatalytic removal of formaldehyde adducts from RNA and DNA bases," Nature Chemistry, 7: 752-758 (2015); US 2017/0283860; and US 2019/0135774, each of which is incorporated by reference herein in its entirety.

In some embodiments, the catalyst is a compound of formula (II):

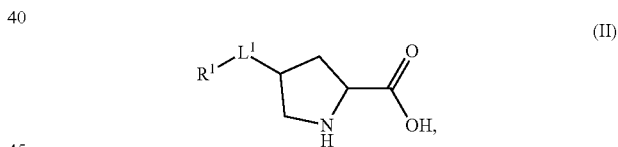

or a salt, zwitterion, or solvate thereof, wherein:
$L^1$ is selected from the group consisting of —O—, —N(H)—, —N($C_{1-3}$ alkyl), —N($CH_2CH_2O$)$_{1-10}$—$CH_3$—, —S(O)$_{0-2}$—, —$CH_2$—, and a bond;
$R^1$ is selected from the group consisting of: H; $C_{1-6}$ alkyl; $C_{1-6}$ haloalkyl; $C_{6-10}$ aryl optionally substituted with 1-4 $R^b$; and 5- to 10-membered heteroaryl, wherein 1-4 ring atoms are heteroatoms each independently selected from the group consisting of: N, N(H), N($C_{1-3}$ alkyl), O, and S, wherein the heteroaryl is optionally substituted with 1-4 independently selected $R^b$; and
each $R^b$ is independently selected from the group consisting of: halo, cyano, —OH, —$NH_2$, —NH($C_{1-3}$ alkyl), —N($C_{1-3}$ alkyl)$_2$, $C_{1-6}$ alkyl, $C_{1-6}$ haloalkyl, $C_{1-4}$ alkoxy, and $C_{1-4}$ haloalkoxy.

In some embodiments of formula (II), -$L^1$-$R^1$ and the —COOH group are cis to one another. In some embodiments of formula (II), -$L^1$-$R^1$ and the —COOH group are trans to one another.

In some embodiments of formula (II), the catalyst is a compound of formula (II-a):

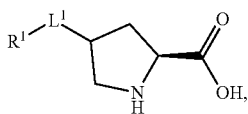
(II-a)

or a salt, zwitterion, or solvate thereof.

In some embodiments of formula (II), the catalyst is a compound of formula (II-a1):

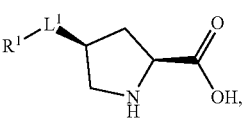
(II-a1)

or a salt, zwitterion, or solvate thereof.

In some embodiments of formula (II), the catalyst is a compound of formula (II-a2):

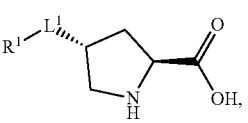
(II-a2)

or a salt, zwitterion, or solvate thereof.

In some embodiments of formula (II), the catalyst is a compound of formula (II-b):

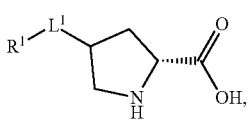
(II-b)

or a salt, zwitterion, or solvate thereof.

In some embodiments of formula (II), the catalyst is a compound of formula (II-b1):

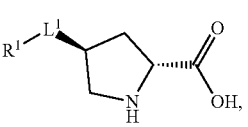
(II-b1)

or a salt, zwitterion, or solvate thereof.

In some embodiments of formula (II), the catalyst is a compound of formula (II-b2):

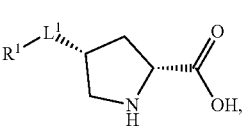
(II-b2)

or a salt, zwitterion, or solvate thereof.

In some embodiments of formula (II), (II-a), (II-a1), (II-a2), (II-b), (II-b1), or (II-b2), $L^1$ is —O—. In some embodiments of formula (II), (II-a), (II-a1), (II-a2), (II-b), (II-b1), or (II-b2), $L^1$ is —N(H)— or —N($C_{1-3}$ alkyl)-. In certain of these embodiments, $L^1$ is —N(H)—.

In some embodiments of formula (II), (II-a), (II-a1), (II-a2), (II-b), (II-b1), or (II-b2), $R^1$ is H.

In some embodiments of formula (II), (II-a), (II-a1), (II-a2), (II-b), (II-b1), or (II-b2), $R^1$ is a heteroaryl containing 5-10 ring atoms, wherein 1-4 ring atoms are heteroatoms each independently selected from the group consisting of: N, N(H), N($C_{1-3}$ alkyl), O, and S; and wherein the heteroaryl is optionally substituted with 1-4 independently selected $R^b$.

In certain of these embodiments, $R^1$ is a heteroaryl containing 5-6 ring atoms, wherein 1-4 ring atoms are heteroatoms each independently selected from the group consisting of: N, N(H), N($C_{1-3}$ alkyl), O, and S; and wherein the heteroaryl is optionally substituted with 1-2 independently selected $R^b$.

In certain of the foregoing embodiments, $R^1$ is a heteroaryl containing 6 ring atoms, wherein 1-2 ring atoms are ring nitrogen atoms, and wherein the heteroaryl is optionally substituted with 1-2 independently selected $R^b$.

As a non-limiting example of the foregoing embodiments, R' can be pyridyl, which is optionally substituted with 1-2 independently selected $R^b$. For example, R' can be 3-pyridyl, which is optionally substituted with 1-2 independently selected $R^b$ (e.g., unsubstituted 3-pyridyl, 3-pyridyl substituted with one $R^b$, or 3-pyridyl substituted with two $R^b$). As another non-limiting example, R' can be 4-pyridyl which is optionally substituted with 1-2 $R^b$ (e.g., unsubstituted 4-pyridyl, 4-pyridyl substituted with one $R^b$, or 4-pyridyl substituted with two $R^b$).

In some embodiments of formula (II), the catalyst is a compound of formula (II-a1); $L^1$ is —O—; and $R^1$ is heteroaryl containing 6 ring atoms, wherein 1-2 ring atoms are ring nitrogen atoms, and wherein the heteroaryl is optionally substituted with 1-2 independently selected $R^b$. In certain of these embodiments, $R^1$ is pyridyl which is optionally substituted with 1-2 independently selected $R^b$. For example, R' can be 3-pyridyl which is optionally substituted with 1-2 independently selected $R^b$ (e.g., unsubstituted 3-pyridyl). As another non-limiting example, R' can be 4-pyridyl which is optionally substituted with 1-2 $R^b$ (e.g., unsubstituted 4-pyridyl).

In some embodiments of formula (II), the catalyst is a compound of formula (II-a1); $L^1$ is —O—, —N(H)—, or —N($C_{1-3}$ alkyl)-; and $R^1$ is H.

In some embodiments, the catalyst is selected from the group consisting of (2S,4R)-4-hydroxyproline, (2R,4S)-4-hydroxyproline, (2S,4S)-4-hydroxyproline, (2R,4R)-4-hydroxyproline, (2S,4R)-4-aminoproline, (2R,4S)-4-aminoproline, (2S,4S)-4-aminoproline, and (2R,4R)-4-aminoproline.

In some embodiments, the catalyst of formula (II) is selected from the group consisting of:

| Compound No. | Compound Structure |
| --- | --- |
| 18 | 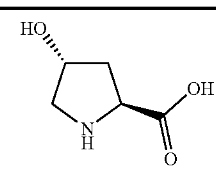 |

-continued

| Compound No. | Compound Structure |
|---|---|
| 19 | ![structure] |
| 20 | ![structure] |
| 21 | ![structure] |
| 22 | ![structure] |
| 23 | ![structure] |
| 24 | ![structure] |
| 25 | ![structure] |
| 26 | ![structure] |
| 27 | ![structure] | or a salt, zwitterion, or solvate thereof.

In some embodiments, the catalyst comprises

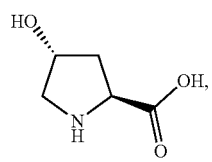

or a salt, zwitterion, or solvate thereof. In some embodiments, the catalyst comprises

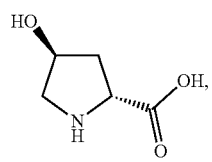

or a salt, zwitterion, or solvate thereof. In some embodiments, the catalyst comprises

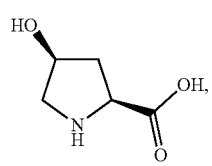

or a salt, zwitterion, or solvate thereof. In some embodiments, the catalyst comprises

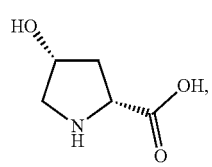

or a salt, zwitterion, or solvate thereof. In some embodiments, the catalyst comprises

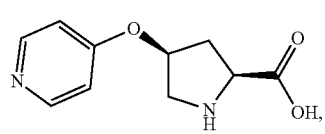

or a salt, zwitterion, or solvate thereof. In some embodiments, the catalyst comprises

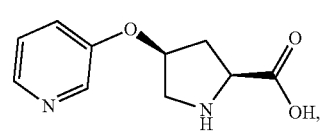

or a salt, zwitterion, or solvate thereof.

In some embodiments, the catalyst is selected from the group consisting of:

| Compound No. | Compound Structure |
|---|---|
| 1 | 5-methyl-2-aminobenzoic acid |
| 2 | 5-nitro-2-aminobenzoic acid |
| 3 | (2-amino-5-methylphenyl)phosphonic acid |
| 4 | 2-amino-5-methylbenzenesulfonic acid |
| 5 | 2,5-diaminobenzenesulfonic acid |
| 6 | 2-amino-3,5-dimethylbenzenesulfonic acid |
| 7 | (2-amino-5-nitrophenyl)phosphonic acid |
| 8 | (4-aminopyridin-3-yl)phosphonic acid |
| 9 | (3-aminopyridin-2-yl)phosphonic acid |
| 10 | (5-aminopyrimidin-4-yl)phosphonic acid |
| 11 | 4-amino-3-phosphono-N-(PEG)benzamide, n = 12–16 |
| 12 | 4-aminonicotinic acid |
| 13 | 3-aminoisonicotinic acid |
| 14 | 2-aminonicotinic acid |
| 15 | (2-aminophenyl)phosphonic acid |
| 16 | (2-amino-5-methoxyphenyl)phosphonic acid |
| 17 | (2-amino-5-(dimethylamino)phenyl)phosphonic acid |

| Compound No. | Compound Structure |
|---|---|
| 18 | 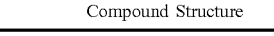 |
| 19 | 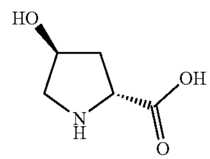 |
| 20 | 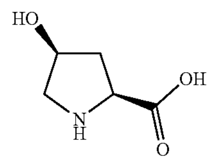 |
| 21 | 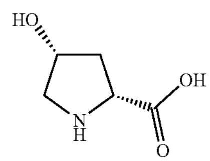 |
| 22 | 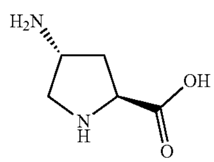 |
| 23 | 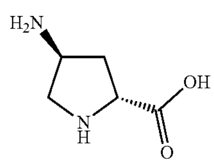 |
| 24 | 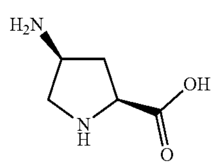 |
| 25 | 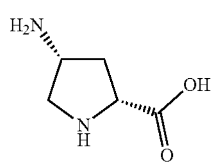 |
| 26 | 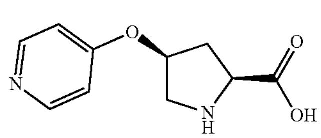 [SMILES: O=C(O)[C@@H]1C[C@H](Oc2ccncc2)CN1] |
| 27 | | or a salt, zwitterion, or solvate thereof.

A catalyst can be contacted with (e.g., applied to) a biological sample at any appropriate concentration. An appropriate concentration may depend on factors such as tissue type, fixation reagent used, and degree of crosslinking in the biological sample. In some embodiments, a catalyst can be contacted with (e.g., applied to) a biological sample in a solution or suspension with a concentration of about 5 mM to about 500 mM (e.g., about 10 mM to about 100 mM, about 10 mM to about 200 mM, about 10 mM to about 300 mM, about 10 mM to about 400 mM, about 100 mM to about 200 mM, about 100 mM to about 300 mM, about 100 mM to about 400 mM, about 100 mM to about 500 mM, about 200 mM to about 300 mM, about 200 mM to about 400 mM, about 200 mM to about 500 mM, about 300 mM to about 400 mM, about 300 mM to about 500 mM, or about 400 mM to about 500 mM). In some embodiments, a catalyst can be contacted with (e.g., applied to) a biological sample in a solution or suspension with a concentration of about 10 mM to about 100 mM (e.g., about 10 mM to about 20 mM, about 10 mM to about 30 mM, about 10 mM to about 40 mM, about 10 mM to about 50 mM, about 10 mM to about 60 mM, about 10 mM to about 70 mM, about 10 mM to about 80 mM, about 10 mM to about 90 mM, about 20 mM to about 30 mM, about 20 mM to about 40 mM, about 20 mM to about 50 mM, about 20 mM to about 60 mM, about 20 mM to about 70 mM, about 20 mM to about 80 mM, about 20 mM to about 90 mM, about 20 mM to about 100 mM, about 30 mM to about 40 mM, about 30 mM to about 50 mM, about 30 mM to about 60 mM, about 30 mM to about 70 mM, about 30 mM to about 80 mM, about 30 mM to about 90 mM, about 30 mM to about 100 mM, about 40 mM to about 50 mM, about 40 mM to about 60 mM, about 40 mM to about 70 mM, about 40 mM to about 80 mM, about 40 mM to about 90 mM, about 40 mM to about 100 mM, about 50 mM to about 60 mM, about 50 mM to about 70 mM, about 50 mM to about 80 mM, about 50 mM to about 90 mM, about 50 mM to about 100 mM, about 60 mM to about 70 mM, about 60 mM to about 80 mM, about 60 mM to about 90 mM, about 60 mM to about 100 mM, about 70 mM to about 80 mM, about 70 mM to about 90 mM, about 70 mM to about 100 mM, about 80 mM to about 90 mM, about 80 mM to about 100 mM, or about 90 mM to about 100 mM) of the catalyst. In some embodiments, a catalyst can be contacted with (e.g., applied to) a biological sample in a solution or suspension with a concentration of about 30 mM to about 70 mM of the catalyst. In some embodiments, a catalyst can be contacted with (e.g., applied to) a biological sample in a solution or suspension with a concentration of about 40 mM to about 60 mM of the catalyst. In some embodiments, a catalyst can be contacted with (e.g., applied to) a biological sample in a solution or suspension with a concentration of about 50 mM of the catalyst.

In some embodiments, the catalyst is contacted with the biological sample at a concentration between about 5 mM and about 500 mM. In some embodiments, the catalyst is contacted with the biological sample at a concentration between about 10 mM and about 400 mM. In some embodiments, the catalyst is contacted with the biological sample at a concentration between about 50 mM and about 300 mM. In some embodiments, the catalyst is contacted with the biological sample at a concentration between about 75 mM and about 250 mM. In some embodiments, the catalyst is contacted with the biological sample at a concentration between about 100 mM and about 200 mM, such as about 100 mM, about 110 mM, about 120 mM, about 130 mM, about 140 mM, about 150 mM, about 160 mM, about 170 mM, about 180 mM, about 190 mM, or about 200 mM.

The catalyst can be contacted to the biological sample for a time sufficient to de-crosslink some or all of the cross-linked nucleic acids and/or proteins in the biological sample (e.g., a cell or tissue sample such as a tissue section). In some embodiments, the catalyst can be contacted to the biological sample for between 1 minute and 1 day (e.g., between 1 minute and 1 hour, 1 minute and 2 hours, 1 minute and 4 hours, 1 minute and 6 hours, 1 minute and 12 hours, 1 minute and 18 hours, 1 hour and 2 hours, 1 hour and 4 hours, 1 hour and 6 hours, 1 hour and 12 hours, 1 hour and 18 hours, 1 hour and 1 day, 2 hours and 4 hours, 2 hours and 6 hours, 2 hours and 12 hours, 2 hours and 18 hours, 2 hours and 1 day, 4 hours and 6 hours, 4 hours and 12 hours, 4 hours and 18 hours, 4 hours and 1 day, 6 hours and 12 hours, 6 hours and 18 hours, 6 hours and 1 day, 12 hours and 18 hours, 12 hours and 1 day, or 18 hours and 1 day). In some embodiments, the catalyst is contacted with the biological sample for about 1 minute to about 150 minutes. In some embodiments, the catalyst is contacted with the biological sample for about 5 minute to about 100 minutes. In some embodiments, the catalyst is contacted with the biological sample for about 10 minute to about 50 minutes. In some embodiments, the catalyst is contacted with the biological sample for about 15 minute to about 30 minutes.

The catalyst can be contacted to the biological sample at a temperature sufficient to de-crosslink some or all of the crosslinked nucleic acids and/or proteins in the biological sample (e.g., a cell or tissue sample such as a tissue section). In some embodiments, the catalyst is contacted with the biological sample at a temperature between about 5° C. and about 100° C. In some embodiments, the catalyst is contacted with the biological sample at a temperature between about 50° C. and about 95° C. In some embodiments, the catalyst is contacted with the biological sample at a temperature between about 60° C. and about 90° C., such as about 60° C., about 65° C., about 70° C., about 75° C., about 80° C., about 85° C., or about 90° C.

A biological sample (e.g., a cell or tissue sample such as a tissue section) can be incubated while the catalyst is contacted with (e.g., applied to) the biological sample. In some embodiments, the biological sample can be incubated between about 25° C. and about 100° C. In some embodiments, the biological sample can be incubated between about 25° C. and about 40° C., about 37° C. and about 60° C., about 45° C. and about 95° C., about 50° C. and about 90° C., about 55° C. and about 85° C., about 60° C. and about 85° C., about 75° C. and about 85° C. In some embodiments, the biological sample can be incubated at about 80° C.

In some embodiments, an incubation temperature and a contact time can be related. Without being bound by any particular theory, it is believed that if a higher temperature is used, a shorter contact time may be sufficient (e.g., 70° C. to 80° C. for 30 minutes), while if a lower temperature is used, a longer contact time may be beneficial (e.g., 37° C. for 1 day). However, in some cases, both a low temperature and a shorter contact time may be sufficient (e.g., 20° C. to 28° C. for 90 minutes). In some embodiments, the catalyst can be contacted to the biological sample for between 1 hour and 120 minutes (e.g., between 1 minute and 110 minutes, 1 minute and 100 minutes, 1 minute and 90 minutes, 1 minute and 80 minutes, 1 minute and 70 minutes, 10 minutes and 120 minutes, 20 minutes and 120 minutes, 30 minutes and 120 minutes, 40 minutes and 120 minutes, 50 minutes and 120 minutes. In some embodiments, the catalyst agent can be applied to the biological sample for about 10 minutes, about 20, 30, 40, 50, 60, 70, 80, 90, 110, or about 120 minutes, and at a temperature between about 70° C. and about 95° C., such as about 70° C., about 75° C., about 80° C., about 85° C., about 90° C., or 95° C. In some embodiments, the catalyst can be contacted to the biological sample for approximately 30 minutes at a temperature between about 75° C. and about 85° C., such as about 80° C.

A catalyst can be delivered to a biological sample using any appropriate method. In some embodiments, a catalyst can be delivered as a solution or a suspension. In some embodiments, a catalyst can be delivered as a solution or a suspension in a buffer. In some embodiments, the buffer is citrate, tris(hydroxymethyl)aminomethane (Tris), Tris-EDTA, phosphate-buffered saline (PBS), 2-[4-(2-hydroxyethyl)piperazin-1-yl]ethanesulfonic acid (HEPES), 2-(N-morpholino)ethanesulfonic acid (MES), or a combination thereof. In some embodiments, the buffer is Tris. In some embodiments, the buffer comprises Tris and a chelating agent, optionally wherein the chelating agent is ethylenediaminetetraacetic acid (EDTA) and the buffer is Tris-EDTA (TE). In some embodiments, the buffer comprises citrate. In some embodiments, the buffer comprises citrate and dimethyl sulfoxide (DMSO). In some embodiments, the buffer comprises 1%-5% (v/v) DMSO. In some embodiments, the buffer comprises 2% (v/v) DMSO. In some embodiments, the buffer comprises citrate but no DMSO. A buffer can have any appropriate concentration. For example, in some embodiments, a buffer can have a concentration of about 5 mM to about 60 mM (e.g., about 10 mM to about 50 mM, about 20 mM to about 40 mM, or about 30 mM). In some embodiments, the catalyst is formulated with DMSO and combined with the buffer (e.g., a citrate buffer, a PBS buffer, or a TE buffer) or before contacting the biological sample.

In some embodiments, the buffer is present in the solution or suspension at a concentration between about 5 mM and about 300 mM. In some embodiments, the buffer is present in the solution or suspension at a concentration between about 10 mM and about 250 mM, such as between about 100 mM and about 200 mM, such as about 100 mM, about 110 mM, about 120 mM, about 130 mM, about 140 mM, about 150 mM, about 160 mM, about 170 mM, about 180 mM, about 190 mM, or about 200 mM.

In some embodiments, the solution or suspension has a pH between about 4 and about 10. In some embodiments, the solution or suspension has a pH between about 6 and about 9. In some embodiments, the solution or suspension has a pH between about 6.5 and about 8, such as between about 6.8 and about 7.4. In some embodiments, the buffer is present at a concentration between about 100 mM and about 200 mM in the solution or suspension having a pH between about 6.5 and about 8, such as pH 6.6, pH 6.7, pH 6.8, pH 6.9, pH 7.0, pH 7.1, pH 7.2, or pH 7.3, pH 7.4, pH 7.5, pH 7.6, pH 7.7, pH 7.8, or pH 7.9.

In some embodiments, the compound in the solution or suspension can exist in various forms, e.g., depending on the pH of the solution or suspension, and one or more of the forms can function as a catalyst to de-crosslink molecular crosslinks in the sample. Examples of pH-dependent acid catalysis are shown in FIGS. 3A-3C. For instance, in FIG. 3B, Compound 1 can exist in two forms—compound A and compound B—in a solution at pH 6.8, but only compound B with —COOH may catalyze a de-crosslinking reaction for reversal of aminal crosslinks. At pH 9, Compound 1 exists mostly as compound A, which is a deprotonated form that does not catalyze the de-crosslinking reaction. FIG. 3C shows phosphonic acid catalysts may perform well at pH 6.8 since —OH of the phosphonic acid exists in solution to catalyze a de-crosslinking reaction exemplified in FIG. 2C.

Exemplary reagents for inclusion in the solution or suspension described herein may include, but are not limited to, water, various non-ionic detergents, saline-sodium citrate (SSC), sodium phosphate, phosphate buffered saline (PBS), sodium dodecyl sulfate (SDS), urea, proteinase (e.g., proteinase K), bovine serum albumin (BSA), ethylenediaminetetracetic acid (EDTA), a sarkosyl compound (e.g., sodium lauroyl sarcosinate; sarkosyl, ammonium salt; or sarkosyl, potassium salt), tris(hydroxymethyl)aminomethane (tris), tris-HCl (tris hydrochloride), 3-morpholinopropane-1-sulfonic acid (MOPS), TAE buffer (tris EDTA), TBS buffer (tris buffered saline), bis-tris methane, 4-(2-hydroxyethyl)-1-piperazineethanesulfonic acid (HEPES buffer), dimethyl sulfoxide (DMSO), quaternary ammonium salts (e.g., tetramethylammonium chloride (TMAC)), trimethylbenzylammonium chloride (TMBAC), tetraethylphosphonium chloride (TEPC), triethylbenzylammonium chloride (TEBAC), tetra-n-propylammonium chloride (TPAC), tri-n-butylbenzylammonium chloride (TBBAC), tetra-n-butylphosphonium chloride (TBPC), (3-((3-cholamidopropyl) dimethylammonio)-1-propanesulfonate) (3-((3-cholamidopropyl) dimethylammonio)-1-propanesulfonate) (CHAPS detergent), and choline dihydrogen phosphate (choline DHP). The solution or suspension may include a zwitterionic catalyst and/or a zwitterionic detergent.

In some embodiments, the solution or suspension comprises sodium dodecyl sulfate (SDS), urea, and/or a proteinase, optionally wherein the proteinase is proteinase K. In some embodiments, the solution or suspension comprises SDS and proteinase K. In some embodiments, the solution or suspension comprises urea and proteinase K. In some embodiments, the urea concentration is between about 0.01 M and about 1 M, such as 0.01 M, 0.02 M, 0.05 M, 0.1 M, 0.2 M, 0.5 M, 0.75 M, or 1 M, or any concentration in between the aforementioned values. In some embodiments, the proteinase K concentration is between about 0.1 μg/mL and about 2 μg/mL, such as 0.1 μg/mL, 0.2 μg/mL, 0.5 μg/mL, 0.75 μg/mL, 1 μg/mL, 1.25 μg/mL, 1.5 μg/mL, 1.75 μg/mL, or 2 μg/mL, or any concentration in between the aforementioned values. In some embodiments, the SDS concentration (w/v) is between about 0.01% and about 1%, such as 0.05%, 0.1%, 0.2%, 0.5%, 0.75%, or 1%, or any concentration in between the aforementioned values. In some embodiments, the solution or suspension comprises 0.05% SDS, 0.2% SDS, 0.5% SDS, 0.05 M urea, 0.5 M urea, 0.2 μg/ml proteinase K, 0.5 μg/ml proteinase K, 1 μg/ml proteinase K, or any combination thereof. In some embodiments, using SDS, urea, and/or proteinase K in de-crosslinking conditions increases puncta brightness, object counts (e.g., puncta number per unit area), and/or signal-to-noise ratio.

In some embodiments, disclosed herein is a catalyst (e.g., a compound of formula (I) or (II) disclosed herein) in a solution or suspension comprising phosphate buffered saline (PBS), e.g., a PBS buffer solution having a pH between about 6.5 and about 8, such as pH 6.6, pH 6.7, pH 6.8, pH 6.9, pH 7.0, pH 7.1, pH 7.2, or pH 7.3, pH 7.4, pH 7.5, pH 7.6, pH 7.7, pH 7.8, or pH 7.9. In some embodiments, disclosed herein is a catalyst (e.g., a compound of formula (I) or (II) disclosed herein) in a PBS buffer solution having a pH of about 7.4. In some embodiments, disclosed herein is a compound of formula (I), such as 2-amino-5-methylbenzoic acid, (2-aminophenyl)phosphonic acid, and/or (4-aminopyridin-3-yl)phosphonic acid, as well as a PBS buffer solution having a pH of about 7.4 comprising the compound of formula (I).

In some embodiments, disclosed herein is a catalyst (e.g., a compound of formula (I) or (II) disclosed herein) in a solution or suspension comprising citrate, e.g., a citrate solution having a pH between about 5 and about 8, such as about pH 5.5, about pH 6.0, about pH 6.5, about pH 7.0, or about pH 7.5. In some embodiments, disclosed herein is a catalyst (e.g., a compound of formula (I) or (II) disclosed herein) in a citrate buffer solution having a pH of about 6.0. In some embodiments, disclosed herein is a compound of formula (I), such as 2-amino-5-methylbenzoic acid, (2-aminophenyl)phosphonic acid, and/or (4-aminopyridin-3-yl)phosphonic acid, as well as a citrate buffer solution having a pH of about 6.0 comprising the compound of formula (I).

In some embodiments, disclosed herein is a catalyst (e.g., a compound of formula (I) or (II) disclosed herein) in a solution or suspension comprising Tris, e.g., a Tris-EDTA solution having a pH between about 8 and about 10, such as about pH 8.5, about pH 9.0, about pH 9.5, or about pH 10.0. In some embodiments, disclosed herein is a catalyst (e.g., a compound of formula (I) or (II) disclosed herein) in a Tris-EDTA buffer solution having a pH of about 9.0. In some embodiments, disclosed herein is a compound of formula (I), such as 2-amino-5-methylbenzoic acid, (2-aminophenyl)phosphonic acid, and/or (4-aminopyridin-3-yl)phosphonic acid, as well as a Tris-EDTA buffer solution having a pH of about 9.0 comprising the compound of formula (I).

A catalyst can be contacted with (e.g., applied to) the biological sample (e.g., a cell or tissue sample such as a tissue section) in any number of ways. In some embodiments, a catalyst is in solution or a suspension. In some embodiments, the biological sample is soaked in a solution or suspension comprising the catalyst. In some embodiments, the catalyst is sprayed onto the biological sample, e.g., as a solution or suspension. In some embodiments, the catalyst is supplied to the biological sample via a microfluidic system (e.g., as a solution or suspension). In some embodiments, a catalyst is pipetted or otherwise aliquoted onto the biological sample. In some embodiments, the biological sample is dipped into a solution or suspension of a catalyst, wherein excess solution or suspension is removed from the biological sample. In some embodiments, a catalyst can be delivered to the biological sample via a hydrogel, wherein the hydrogel is contacted with the biological sample. Application of a catalyst can occur in other suitable ways.

In some embodiments, a composition comprising a catalyst or compound disclosed herein can be used in combination with one or more other de-crosslinking and/or antigen retrieving agents including enzymes such as proteases. Exemplary proteases include a proteinase (e.g., collagenase), which can be present in any appropriate concentration (e.g., about 0.005 to about 0.5 U/μL (e.g., about 0.01 to about 0.5 U/μL, about 0.05 to about 0.5 U/μL, about 0.1 to about 0.5 U/μL, about 0.1 to about 0.3 U/μL, or about 0.2 U/μL). In some embodiments, a proteinase can be pepsin, Proteinase K, or an ArcticZymes Proteinase (an unspecific endopeptidase that can be inactivated after use). The proteinase can optionally be applied with a buffer, such as Hank's Balanced Salt Solution (HBSS) buffer.

In some embodiments, a composition comprising a catalyst or compound disclosed herein can be used in combination with one or more crowding agents, e.g., to mitigate potential RNA loss during de-crosslinking. Crowding agents are typically high-molecular weight, high valency polymers that may be charged. For example, crowding agents may be polymers such as dextran sulfate, polyacrylic acid, polyvinylsulfonic acid, and alginate. Optionally, crowding agents may be polymers similar to dextran sulfate. In some embodiments, compounds that can function as crowding agents, but have some property of molecular programmability may be used. For example, some polymers that can function as crowding agents can be used and subsequently the charged group can be cleaved off or neutralized. This can convert the compound into a neutral polymer like PEG, which actually enhances the efficiency of enzymatic reactions. In some embodiments, polymers can function as a crowding agent, and then be specifically degraded into small monomers and can be easily washed from the sample. Examples of programmable polyions or polyelectrolytes for enzyme-compatible enhancement of nucleic acid hybridization kinetics (e.g., for hybridization of nucleic acid probes to molecules in the sample after de-crosslinking) include polycondensation reactions of Cys(Lys)$_n$Cys, polymers such as PEG (PEG20k MW), PVA, or PAA, which may be subsequently modified via a cleavable linker to include chemical groups conferring ionic charge, or polymers formed from monomers including cleavable linkages, such that the polymer may be degraded subsequent to functioning as a crowding agent.

D. Preparing De-Crosslinked Samples for In Situ Analysis

In some embodiments, after catalytic de-crosslinking, a biological sample (e.g., tissue section) is permeabilized (e.g., undergoes permeabilization). In some embodiments, the sample is permeabilized after delivery to or application of a de-crosslinking agent. In some embodiments, the permeabilization comprises harsher conditions than the optional pretreatment step. In some embodiments, the permeabilization comprises applying one or more permeabilization reagents to the biological sample. In some embodiments, a permeabilization reagent can comprise a protease. In some embodiments, the protease comprises pepsin. In some embodiments, the protease comprises proteinase K. In some embodiments, the protease comprises ArcticZyme Proteinase. In some embodiments, the protease is provided in a solution of hydrochloric acid. In some embodiments, after catalytic de-crosslinking, a biological sample (e.g., tissue section) is contacted with a protease, e.g., washed using a solution containing a protease, prior to contacting the biological sample with a labelling agent (e.g., a probe or probe set) that directly or indirectly binds to an analyte at a location in the biological sample. In some examples, provided is a method comprising contacting an intact biological sample with a labelling agent that directly or indirectly binds to an analyte at a location in the biological sample.

The permeabilization reagent(s) can be applied to biological sample (e.g., tissue section) in any number of ways. In some embodiments, the permeabilization reagents can be in solution or suspension. In some embodiments, the sample is soaked in a solution or suspension of the permeabilization reagent(s). In some embodiments, the permeabilization reagents are sprayed onto the sample (e.g., as a solution or suspension). In some embodiments, the permeabilization reagents are supplied to the sample via a microfluidic system (e.g., as a solution or suspension). In some embodiments, the sample can be dipped into a solution or suspension comprising the permeabilization reagent(s), wherein excess permeabilization reagent is removed from the sample. In some embodiments, the permeabilization reagent(s) are delivered to the sample via a hydrogel, wherein the hydrogel is contacted with the sample.

The permeabilization reagent(s) can be contacted to the biological sample (e.g., tissue section) for a time sufficient to permeabilize the sample. In some embodiments, the permeabilization reagent(s) can be contacted to the sample for between 1 minute and 120 minutes. In some embodiments, the permeabilization reagent(s) can be applied to the sample between about 1 minute and 90 minutes, 1 minute and 80 minutes, 1 minute and 70 minutes, 1 minute and 60 minutes, 1 minute and about 55 minutes, about 1 minute and about 50 minutes, about 1 minute and about 45 minutes, about 1 minute and about 40 minutes, about 1 minute and about 35 minutes, about 1 minute and about 30 minutes, about 1 minute about 5 minutes and about 60 minutes, about 10 minutes and about 60 minutes, about 10 minutes and about 55 minutes, about 10 minutes and about 50 minutes, about 10 minutes and about 45 minutes, about 10 minutes and about 40 minutes, about 15 minutes and about 45 minutes, about 20 minutes and about 40 minutes, about 25 minutes and about 35 minutes. In some embodiments, the permeabilization reagent(s) can be contacted to the sample for approximately 30 minutes.

The biological sample (e.g., tissue section) can be incubated with the permeabilization reagent(s). In some embodiments, the sample can be incubated between about 16° C. and about 56° C. (e.g., between about 30° C. and 45° C., or between about 35° C. and about 40° C.). In some embodiments, the biological sample can be at about 16° C., 18° C., 20° C., 22° C., 24° C., 26° C., 28° C., 30° C., 31° C., 32° C., 33° C., 34° C., 35° C., 36° C., 37° C., 38° C., 39° C., 40° C., 41° C., 42° C., 43° C., 44° C., 45° C., 46° C., 48° C., 50° C., 52° C., 54° C., or 56° C. In some embodiments, the sample can be incubated at about 37° C.

In some embodiments, the method comprises a step of permeabilizing the biological sample before, during, and/or after contacting the biological sample with the catalyst for catalytic de-crosslinking. In some embodiments, the method comprises incubating and/or washing a fixed biological sample in a buffer comprising one or more detergents, such as a Tween detergent (e.g., Tween™ 20), before and/or during catalytic de-crosslinking. In some embodiments, the method comprises incubating and/or washing a catalytically de-crosslinked biological sample in a buffer comprising one or more detergents, such as a Tween detergent (e.g., Tween™ 20).

In some embodiments, the method does not comprise migrating molecules (e.g., analytes, labelling agents, nucleic acid probes, etc., or products generated in situ in the sample) outside of the permeabilized biological sample. In some embodiments, the method does not comprise migrating molecules (e.g., analytes, labelling agents, nucleic acid probes, etc., or products generated in situ in the sample) towards the substrate, optionally wherein the migration is passive migration or active migration. In some embodiments, the method does not comprise capturing molecules (e.g., analytes, labelling agents, nucleic acid probes, etc., or products generated in situ in the sample) by a capture agent immobilized on the substrate.

In some embodiments, after catalytic de-crosslinking, a biological sample (e.g., tissue section) can be incubated and/or washed with a solution containing a detergent in any appropriate concentration (e.g., about 0.05% to about 2% (v/v), about 0.1% to about 1% (v/v), about 0.1% (v/v), or about 0.5% (v/v)). In some embodiments, the detergent is a non-ionic detergent. In some embodiments, the detergent comprises Triton™ X-100, Triton™ X-200, Tween™ 20, Tween™ 80, N-lauroyl sarcosine, sodium dodecyl sulfate (SDS), dodecyldimethylphosphine oxide, sorbitan monopalmitate, decylhexaglycol, 4-nonylphenylpolyethylene glycol, CAHPS, IGEPAL CA-630, Sulfobetain-10, Sulfobetain-16, urea, or a combination thereof. In some embodiments, urea solubilizes and denatures proteins by disrupting noncovalent bonds. In some embodiments, the buffer comprises, for example, tris(hydroxymethyl)aminomethane-Ethylenediaminetetraacetic acid (TE), phosphate-buffered saline (PBS), 2-[4-(2-hydroxyethyl)piperazin-1-yl]ethanesulfonic acid (HEPES), and/or 2-(N-morpholino)ethanesulfonic acid (MES), with a pH of about 7.0 to about 9.0 (e.g., about 7.5 to about 8.5, or about 8.0). In some embodiments, the detergent is in a buffer such as PBS. In some embodiments, the buffer is PBS with a Tween detergent (PBST). In some embodiments, the method comprises, after contacting the biological sample with the catalyst, a step of washing the biological sample, optionally wherein the biological sample is washed in PBST, e.g., for three times for 1 minute each.

In some embodiments, the method comprises, after contacting the biological sample with the catalyst, a step of staining the biological sample and imaging the stained biological sample prior to containing the sample with a labelling agent that directly or indirectly binds to an analyte at a location in the biological sample, e.g., for analyte detection using nucleic acid probes for in situ hybridization (e.g., sequential hybridization in sequential rounds of probe hybridization and detection) and/or using labelled antibodies for protein detection (e.g., described in Section III-B and Section III-C).

III. Analytes and Labelling Agents

In some embodiments, provided herein are methods and compositions for sample analysis comprising contacting a fixed biological sample that has been catalytically de-cross-linked with a labelling agent that binds to an analyte at a location in the de-crosslinked fixed biological sample, and detecting an optical signal associated with the labelling agent or a product thereof, thereby detecting the analyte at the location in the biological sample. A biological sample may comprise one or a plurality of analytes of interest. Methods for performing multiplexed assays to analyze two or more different analytes in a single biological sample are provided.

The methods, probes, and kits disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule, macromolecule, or chemical compound, including a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a padlock or other circularizable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules (e.g., cellular nucleic acids), such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which comprises a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

A. Endogenous Analytes

In some embodiments, an analyte herein is endogenous to a biological sample and can include cellular nucleic acid analytes and non-nucleic acid analytes. Methods, probes, and kits disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

Methods, probes, and kits disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte can comprise or be associated with a target sequence. In some embodiments, the target nucleic acid and the target sequence therein may be endogenous to the sample, generated in the sample, added to the sample, or associated with an analyte in the sample. In some embodiments, the target sequence is a single-stranded target sequence (e.g., a sequence in a rolling circle amplification product). In some embodiments, the target sequence is a single-stranded target sequence (e.g., in a probe bound directly or indirectly to the analyte). In some embodiments, the target sequence is a single-stranded target sequence in a primary probe that binds to an analyte of interest in the biological sample. In some embodiments, the target sequence is a single-stranded target sequence in an intermediate probe which directly or indirectly binds to a primary probe or product thereof, where the primary probe binds to an analyte of interest in the biological sample. In some embodiments, the target sequence is a single-stranded target sequence in a secondary probe that binds to the primary probe or product thereof. In some embodiments, the analytes comprises one or more single-stranded target sequences.

B. Analyte Detection

In some embodiments, provided herein are methods, probes, and kits for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some embodiments, a labelling agent that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product such as a rolling circle amplification (RCA) product) of a labelling agent that directly or indirectly binds to an analyte in the biological sample is analyzed. In some instances, the provided methods are for gene expression analysis for RNA transcripts and protein analysis in the same intact biological sample (e.g., a tissue section).

Disclosed herein in some aspects are labelling agents (e.g., nucleic acid probes and/or probe sets) that are introduced into a cell or used to otherwise contact a biological sample such as a tissue sample. The labelling agents include probes (e.g., the primary probes disclosed herein and/or any detectable probe disclosed herein) may comprise any of a variety of entities that can hybridize to a nucleic acid, typically by Watson-Crick base pairing, such as DNA, RNA, LNA, PNA, etc. The nucleic acid probe may comprise a hybridization region that is able to directly or indirectly bind to at least a portion of a target sequence in a target nucleic acid. The nucleic acid probe may be able to bind to a specific target nucleic acid (e.g., an mRNA, or other nucleic acids disclosed herein). In some embodiments, the nucleic acid probes may be detected using a detectable label, and/or by using secondary nucleic acid probes able to bind to the nucleic acid probes. In some embodiments, the nucleic acid probes (e.g., primary probes and/or secondary probes) are compatible with one or more biological and/or chemical reactions. For instance, a nucleic acid probe disclosed herein can serve as a template or primer for a polymerase, a template or substrate for a ligase, a substrate for a click chemistry reaction, and/or a substrate for a nuclease (e.g., endonuclease or exonuclease for cleavage or digestion).

In some embodiments, more than one type of primary nucleic acid probes may be contacted with a sample, e.g., simultaneously or sequentially in any suitable order, such as in sequential probe hybridization/unhybridization cycles. In some embodiments, more than one type of secondary nucleic acid probes may be contacted with a sample, e.g., simultaneously or sequentially in any suitable order, such as in sequential probe hybridization/unhybridization cycles. In some embodiments, the secondary probes may comprise probes that bind to a product of a primary probe targeting an analyte. In some embodiments, more than one type of higher order nucleic acid probes may be contacted with a sample, e.g., simultaneously or sequentially in any suitable order, such as in sequential probe hybridization/unhybridization cycles. In some embodiments, more than one type of detectably labeled nucleic acid probes may be contacted with a sample, e.g., simultaneously or sequentially in any suitable order, such as in sequential probe hybridization/unhybridization cycles. In some embodiments, the detectably labeled nucleic acid probes can be used to bind to one or more primary probes, one or more secondary probes, one or more higher order probes, one or more intermediate probes between a primary/secondary/higher order probes, and/or one or more detectably or non-detectably labeled probes (e.g., as in the case of a hybridization chain reaction (HCR), a branched DNA reaction (bDNA), or the like). In some embodiments, the plurality of probes or probe sets comprises at least 2, at least 5, at least 10, at least 25, at least 50, at least 75, at least 100, at least 300, at least 1,000, at least 3,000, at least 10,000, at least 30,000, at least 50,000, at least 100,000, at least 250,000, at least 500,000, or at least 1,000,000 distinguishable nucleic acid probes (e.g., primary, secondary, higher order probes, and/or detectably labeled probes) that can be contacted with a sample, e.g., simultaneously or sequentially in any suitable order. Between any of the probe contacting steps disclosed herein, the method may comprise one or more intervening reactions and/or processing steps, such as modifications of a target nucleic acid, modifications of a probe or product thereof (e.g., via hybridization, ligation, extension, amplification, cleavage, digestion, branch migration, primer exchange reaction, click chemistry reaction, crosslinking, attachment of a detectable label, activating photo-reactive moieties, etc.), removal of a probe or product thereof (e.g., cleaving off a portion of a probe and/or unhybridizing the entire probe), signal modifications (e.g., quenching, masking, photo-bleaching, signal enhancement (e.g., via FRET), signal amplification, etc.), signal removal (e.g., cleaving off or permanently inactivating a detectable label), crosslinking, de-crosslinking, and/or signal detection.

The hybridization region of the probe or probe set is a target-binding sequence (sometimes also referred to as the targeting region/sequence or the recognition region/sequence) that be positioned anywhere within the probe. For instance, the target-binding sequence of a primary probe that binds to a target nucleic acid can be 5' or 3' to any barcode sequence in the primary probe. Likewise, the target-binding sequence of a secondary probe (which binds to a primary probe or complement or product thereof) can be 5' or 3' to any barcode sequence in the secondary probe. In some embodiments, the target-binding sequence may comprise a sequence that is substantially complementary to a portion of a target nucleic acid. In some embodiments, the portions may be at least 50%, at least 60%, at least 70%, at least 75%, at least 80%, at least 85%, at least 90%, at least 92%, at least 94%, at least 95%, at least 96%, at least 97%, at least 98%, at least 99%, or 100% complementary.

The hybridization region of the probe or probe set can be used to identify a particular analyte comprising or associated with a target (e.g., comprising a target sequence). In some cases, multiple probes can be used, sequentially and/or simultaneously, that can bind to (e.g., hybridize to) different regions of the same target nucleic acid. In other examples, a probe may comprise target-binding sequences (e.g., hybridization regions) that can bind to different target nucleic acid sequences, e.g., various intron and/or exon sequences of the same gene (for detecting splice variants, for example), or sequences of different genes, e.g., for detecting a product that comprises the different target nucleic acid sequences, such as a genome rearrangement (e.g., inversion, transposition, translocation, insertion, deletion, duplication, and/or amplification).

In some embodiments, provided herein are methods, probes, and kits for analyzing endogenous analytes (e.g., RNA, ssDNA, and cell surface or intracellular proteins and/or metabolites) in a sample using one or more labelling agents.

In some embodiments, the labelling agent is an immunohistochemistry (IHC) probe that is excited at various different wavelengths. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode comprises to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety comprises one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes comprises a single species of analyte (e.g., a single species of polypeptide). In some embodiments in which the plurality of analytes comprises a single species of analyte, the analyte binding moieties of the plurality of analyte labelling agents are the same. In some embodiments in which the plurality of analytes comprises a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes comprises multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labelling agent through a labile bond (e.g., chemically labile, photolabile, thermally labile, etc.) as generally described for releasing molecules from supports elsewhere herein.

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (e.g., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

a. Hybridization

In some embodiments, the labelling agents (e.g., probes or probes sets) described herein can be used to detect an endogenous analyte, a product of an endogenous analyte and/or a labelling agent is a hybridization product comprising the pairing of substantially complementary or complementary nucleic acid sequences within two different molecules, one of which is the endogenous analyte or the labelling agent (e.g., reporter oligonucleotide attached thereto). The other molecule can be another endogenous molecule or an exogenous molecule such as a probe. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

Various probes and probe sets can be hybridized to an endogenous analyte and/or a labelling agent and each probe may comprise one or more barcode sequences. In some instances, various probes and probe sets can be used to generate a product comprising a target sequence that can be hybridized by one or more detectable probes. In some instances, a probe or probe set disclosed herein is a circularizable probe or probe set comprising a barcode region comprising one or more barcode sequences. Exemplary barcoded probes or probe sets may be based on a padlock probe, a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, and RNA-templated ligation probes. The specific probe or probe set design can vary.

b. Ligation

In some embodiments, a product of an endogenous analyte and/or a labelling agent is a ligation product that may comprise a target sequence that can be hybridized by one or more probes described herein. In some embodiments, the ligation product is formed between two or more endogenous analytes. In some embodiments, the ligation product is formed between an endogenous analyte and a labelling agent. In some embodiments, the ligation product is formed between two or more labelling agent. In some embodiments, the ligation product is an intramolecular ligation of an endogenous analyte. In some embodiments, the ligation product is an intramolecular ligation of a labelling agent or probe, for example, the circularization of a circularizable probe or probe set upon hybridization to a target sequence. The target sequence can be comprised in an endogenous analyte (e.g., nucleic acid such as genomic DNA or mRNA) or a product thereof (e.g., cDNA from a cellular mRNA transcript), or in a labelling agent (e.g., the reporter oligonucleotide) or a product thereof.

In some embodiments, provided herein is a labelling agent comprising a probe or probe set capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., U.S. Pat. Pub. 2020/0224244 which is hereby incorporated by reference in its entirety. In some embodiments, the probe set is a SNAIL probe set. See, e.g., U.S. Pat. Pub. 20190055594, which is hereby incorporated by reference in its entirety.

In some embodiments, provided herein is a multiplexed proximity ligation assay. See, e.g., U.S. Pat. Pub. 20140194311 which is hereby incorporated by reference in its entirety. In some embodiments, provided herein is a probe or probe set capable of proximity ligation, for instance a proximity ligation assay for RNA (e.g., PLAYR) probe set. See, e.g., U.S. Pat. Pub. 20160108458, which is hereby incorporated by reference in its entirety. In some embodiments, a circular probe can be indirectly hybridized to the target nucleic acid. In some embodiments, the circular construct is formed from a probe set capable of proximity ligation, for instance a proximity ligation in situ hybridization (PLISH) probe set. See, e.g., U.S. Pat. Pub. 2020/0224243 which is hereby incorporated by reference in its entirety.

In some embodiments, a circular or circularizable probe or probe set may be used to analyze a reporter oligonucleotide, which may generated using proximity ligation or be subjected to proximity ligation. In some examples, the reporter oligonucleotide of a labelling agent that specifically recognizes a protein can be analyzed using in situ hybridization (e.g., sequential hybridization) and/or in situ sequencing (e.g., using circular or circularizable probes and rolling circle amplification of circular or circularized probes). Further, the reporter oligonucleotide of the labelling agent and/or a complement thereof and/or a product (e.g., a hybridization product, a ligation product, an extension product (e.g., by a DNA or RNA polymerase), a replication product, a transcription/reverse transcription product, and/or an amplification product) thereof can be recognized by another labelling agent and analyzed.

In some embodiments, an analyte (a nucleic acid analyte or non-nucleic acid analyte) can be specifically bound by two labelling agents (e.g., antibodies) each of which is attached to a reporter oligonucleotide (e.g., DNA) that can participate in ligation, replication, and sequence decoding reactions, e.g., using a probe or probe set (e.g., a padlock probe, a SNAIL probe set, a circular probe, a gapped padlock probe, or a gapped padlock probe and a connector). In some embodiments, the probe set may comprise two or more probe oligonucleotides, each comprising a region that is complementary to each other. For example, a proximity ligation reaction can include reporter oligonucleotides attached to pairs of antibodies that can be joined by ligation if the antibodies have been brought in proximity to each other, e.g., by binding the same target protein (complex), and the DNA ligation products that form are then used to template PCR amplification, as described for example in Soderberg et al., Methods. (2008), 45(3): 227-32, the entire contents of which are incorporated herein by reference. In some embodiments, a proximity ligation reaction can include reporter oligonucleotides attached to antibodies that each bind to one member of a binding pair or complex, for example, for analyzing a binding between members of the binding pair or complex. For detection of analytes using oligonucleotides in proximity, see, e.g., U.S. Patent Application Publication No. 2002/0051986, the entire contents of which are incorporated herein by reference. In some embodiments, two analytes in proximity can be specifically bound by two labelling agents (e.g., antibodies) each of which is attached to a reporter oligonucleotide (e.g., DNA) that can participate, when in proximity when bound to their respective targets, in ligation, replication, and/or sequence decoding reactions.

In some embodiments, one or more reporter oligonucleotides (and optionally one or more other nucleic acid molecules such as a connector) aid in the ligation of the probe. Upon ligation, the probe may form a circularized probe. In some embodiments, one or more suitable probes can be used and ligated, wherein the one or more probes comprise a sequence that is complementary to the one or more reporter oligonucleotides (or portion thereof). The probe may comprise one or more barcode sequences. In some embodiments, the one or more reporter oligonucleotide may serve as a primer for rolling circle amplification (RCA) of the circularized probe. In some embodiments, a nucleic acid other than the one or more reporter oligonucleotide is used as a primer for rolling circle amplification (RCA) of the circularized probe. For example, a nucleic acid capable of hybridizing to the circularized probe at a sequence other than sequence(s) hybridizing to the one or more reporter oligonucleotide can be used as the primer for RCA. In other examples, the primer in a SNAIL probe set is used as the primer for RCA.

In some embodiments, one or more analytes can be specifically bound by two primary antibodies, each of which is in turn recognized by a secondary antibody each attached to a reporter oligonucleotide (e.g., DNA). Each nucleic acid molecule can aid in the ligation of the probe to form a circularized probe. In some instances, the probe can comprise one or more barcode sequences. Further, the reporter oligonucleotide may serve as a primer for rolling circle amplification of the circularized probe. The nucleic acid molecules, circularized probes, and RCA products can be analyzed using any suitable method disclosed herein for in situ analysis.

In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as E. coli DNA ligase, Tth DNA ligase, Thermococcus sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, e.g., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, padlock probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

c. Primer Extension

In some embodiments, a primer extension product of an analyte, a labelling agent, a probe or probe set bound to the analyte (e.g., bound to genomic DNA, mRNA, or cDNA), or a probe or probe set bound to the labelling agent (e.g., bound to one or more reporter oligonucleotides from the same or different labelling agents). Any of such products of extension may comprise a target sequence that can be hybridized by the plurality of probes or probe sets described herein.

In some embodiments, the plurality of probes or probe sets comprises a primer. A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence. A primer extension reaction generally refers to any method where two nucleic acid sequences become linked (e.g., hybridized) by an overlap of their respective terminal complementary nucleic acid sequences (e.g., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some embodiments, a product of an endogenous analyte and/or a labelling agent is an amplification product of one or more polynucleotides, for instance, a circular probe or circularizable probe or probe set. In some embodiments, the amplifying is achieved by performing rolling circle amplification (RCA). In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (e.g., amplicon) containing multiple copies of the cDNA. Techniques for rolling circle amplification (RCA) include linear RCA, a branched RCA, a dendritic RCA, or any combination thereof. See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97(18):10113-9, 2000; Faruqi et al, BMC Genomics 2:4, 2000; Nallur et al, Nucl. Acids Res. 29:e118, 2001; Dean et al. Genome Res. 11:1095-1099, 2001; Schweitzer et al, Nature Biotech. 20:359-365, 2002; U.S. Pat. Nos. 6,054,274, 6,291,187, 6,323,009, 6,344,329 and 6,368,801, all of which are incorporated by reference. Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a $N^6$-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, US 2016/0024555, US 2018/0251833, US 2017/0219465, U.S. Pat. Nos. 10,138,509, 10,494,662, 11,078,520, 11,299,767, 10,266,888, 11,118,220, US 2021/0363579, US 2021/0324450, and US 2021/0215581, all of which are herein incorporated by reference in their entireties. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

In some embodiments, the RCA template may comprise the target analyte, or a part thereof, where the target analyte is a nucleic acid, or it may be provided or generated as a proxy, or a marker, for the analyte. As noted above, the detection of numerous different analytes may use a RCA-based detection system, e.g., where the signal is provided by generating a target sequence from a circular RCA template which is provided or generated in the assay, and the target sequence is detected to detect the corresponding analyte. The target sequence may thus be regarded as a reporter which is detected to detect the target analyte. However, the RCA template may also be regarded as a reporter for the target analyte; the target sequence is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (e.g. a reagent in a detection assay), which is used as a reporter for the assay, or a part of a reporter, or signal-generation system. The RCA template used to generate the target sequence may thus be a circular (e.g. circularized) reporter nucleic acid molecule, namely from any RCA-based detection assay which uses or generates a circular nucleic acid molecule as a reporter for the assay. Since the RCA template generates the target sequence reporter, it may be viewed as part of the reporter system for the assay.

In some embodiments, a product herein comprises a molecule or a complex generated in a series of reactions, e.g., hybridization, ligation, extension, replication, transcription/reverse transcription, and/or amplification (e.g., rolling circle amplification), in any suitable combination. For example, a product comprising a target sequence for a target-binding region in a probe may be a hybridization complex formed of a cellular nucleic acid in a sample and an exogenously added nucleic acid probe or a product generated therefrom. The exogenously added nucleic acid probe (e.g., plurality of probes or probe sets) may comprise an overhang that does not hybridize to the cellular nucleic acid but hybridizes to another probe (e.g., an intermediate probe).

In some embodiments, the labelling agents may bind or hybridize to a target. In some instances, a target comprises a target sequence for a probe or probe set. In some instances, the plurality of probes or probe sets may be used to generate a product comprising signal amplification components. In some instances, the amplification comprises one or more probe hybridizations and generation of amplified signals associated with the labelling agents (e.g., probes). Exemplary signal amplification methods include targeted assembly of branched structures (e.g., bDNA). In some instances, detection of nucleic acids sequences in situ includes combination of the sequential decoding methods described herein with an assembly for branched signal amplification using the nucleic acid probes provided herein. In some instances, the assembly complex comprises an amplifier hybridized directly or indirectly (via one or more oligonucleotides) to a sequence of a cellular nucleic acid.

After contacting the biological sample with a plurality of labelling agents (e.g., probes or probe sets), the probes may be directly detected by determining detectable labels (if present), and/or detected by using one or more other probes that bind directly or indirectly to the plurality of probes or probe sets or products thereof. The one or more other probes may comprise a detectable label. For instance, a primary nucleic acid probe can bind to a target nucleic acid in the sample, and a secondary nucleic acid probe can be introduced to bind to the primary nucleic acid probe, where the secondary nucleic acid probe or a product thereof can then be detected using detectable probes (e.g., detectably labeled probes). Higher order probes that directly or indirectly bind to the secondary nucleic acid probe or product thereof may also be used, and the higher order probes or products thereof can then be detected using detectably labeled probes.

In some instances, a secondary nucleic acid probe binds to a primary nucleic acid probe directly hybridized to the target nucleic acid. A secondary nucleic acid probe (e.g., a first detectable probe or a second detectable probe disclosed herein) may contain a recognition sequence able to bind to or hybridize with a primary nucleic acid probe (e.g., probes or probe sets disclosed herein) or a product thereof (e.g., an RCA product), e.g., at a barcode sequence or portion(s) thereof of the probes or probe sets or products thereof. In some embodiments, a secondary nucleic acid probe may bind to a combination of barcode sequences (which may be continuous or spaced from one another) in the probes or probe sets, a product thereof. In some embodiments, the binding is specific, or the binding may be such that a recognition sequence preferentially binds to or hybridizes with only one of the barcode sequences or complements thereof that are present. The secondary nucleic acid probe may also contain one or more detectable labels. If more than one secondary nucleic acid probe is used, the detectable labels may be the same or different.

The recognition sequences may be of any length, and multiple recognition sequences in the same or different secondary nucleic acid probes may be of the same or different lengths. If more than one recognition sequence is used, the recognition sequences may independently have the same or different lengths. For instance, the recognition sequence may be at least 4, at least 5, least 6, least 7, least 8, least 9, at least 10, least 11, least 12, least 13, least 14, at least 15, least 16, least 17, least 18, least 19, at least 20, at least 25, at least 30, at least 35, at least 40, or at least 50 nucleotides in length. In some embodiments, the recognition sequence may be no more than 48, no more than 40, no more than 32, no more than 24, no more than 16, no more than 12, no more than 10, no more than 8, or no more than 6 nucleotides in length. Combinations of any of these are also possible, e.g., the recognition sequence may have a length of between 5 and 8, between 6 and 12, or between 7 and 15 nucleotides, etc. In some embodiments, the recognition sequence is of the same length as a barcode sequence or complement thereof of a primary nucleic acid probe or a product thereof. In some embodiments, the recognition sequence may be at least 50%, at least 60%, at least 70%, at least 75%, at least 80%, at least 85%, at least 90%, at least 92%, at least 94%, at least 95%, at least 96%, at least 97%, at least 98%, at least 99%, or at least 100% complementary to the barcode sequence or complement thereof.

In some embodiments, the probes or probe sets, or an intermediate probe, may also comprise 1, 2, 3, 4, 5, 6, 7, 8, 9, 10, 11, 12, 13, 14, 15 or more, 20 or more, 32 or more, 40 or more, or 50 or more barcode sequences. As an illustrative example, a first probe may contain a first target-binding sequence, a first barcode sequence, and a second barcode sequence, while a second, different probe may contain a second target-binding sequence (that is different from the first target-binding sequence in the first probe), the same first barcode sequence as in the first probe, but a third barcode sequence instead of the second barcode sequence. Such probes may thereby be distinguished by determining the various barcode sequence combinations present or associated with a given probe at a given location in a sample.

In some embodiments, the nucleic acid probes disclosed herein may be made using only 2 or only 3 of the 4 bases, such as leaving out all the "G"s and/or leaving out all of the "C"s within the probe. Sequences lacking either "G"s or "C"s may form very little secondary structure, and can contribute to more uniform, faster hybridization in certain embodiments.

In some embodiments, a nucleic acid probe disclosed herein may contain a detectable label such as a fluorophore. In some embodiments, one or more probes of a plurality of nucleic acid probes used in an assay may lack a detectable label, while one or more other probes in the plurality each comprises a detectable label selected from a limited pool of distinct detectable labels (e.g., red, green, yellow, and blue fluorophores), and the absence of detectable label may be used as a separate "color." As such, detectable labels are not required in all cases. In some embodiments, a primary nucleic acid probe disclosed herein lacks a detectable label. While a detectable label may be incorporated into an amplification product of a probe, such as via incorporation of a modified nucleotide into an RCA product of a circularized probe, the amplification product itself in some embodiments is not detectably labeled. In some embodiments, a probe that binds to the primary nucleic acid probe or a product thereof (e.g., a secondary nucleic acid probe that binds to a barcode sequence or complement thereof in the primary nucleic acid probe or product thereof) comprises a detectable label and may be used to detect the primary nucleic acid probe or product thereof. In some embodiments, a secondary nucleic acid probe disclosed herein lacks a detectable label, and a detectably labeled probe that binds to the secondary nucleic acid probe or a product thereof (e.g., at a barcode sequence or complement thereof in the secondary nucleic acid probe or product thereof) can be used to detect the second nucleic acid probe or product thereof. In some embodiments, signals associated with the detectably labeled probes (e.g., the first detectable probe which is detectably labelled, the second detectable probe which is detectably labelled, a detectably labeled probe that binds to the first detectable probe which itself is not detectably labelled, or a detectably labeled probe that binds to the second detectable probe which itself is not detectably labelled) can be used to detect one or more barcode sequences in the secondary probe and/or one or more barcode sequences in the primary probe, e.g., by using sequential hybridization of detectably labeled probes, sequencing-by-ligation, and/or sequencing-by-hybridization. In some embodiments, the barcode sequences (e.g., in the secondary probe and/or in the primary probe) are used to combinatorially encode a plurality of analytes of interest. As such, signals associated with the detectably labeled probes at particular locations in a biological sample can be used to generate distinct signal signatures that each corresponds to an analyte in the sample, thereby identifying the analytes at the particular locations, e.g., for in situ spatial analysis of the sample.

In some embodiments, probes or probe sets described herein comprises one or more other components, such as one or more primer binding sequences (e.g., to allow for enzymatic amplification of probes), enzyme recognition sequences (e.g., for endonuclease cleavage), or the like. The components of the nucleic acid probe may be arranged in any suitable order3

In some aspects, targets (e.g., analytes) are targeted by labelling agents (e.g., probes or probe sets) described herein, which are barcoded through the incorporation of one or more barcode sequences (e.g., sequences that can be detected or otherwise "read") and binds the targeted analyte. In some aspects, the probes or probe sets described herein are in turn targeted by secondary probes e.g., intermediate probes, which are also barcoded through the incorporation of one or more barcode sequences that are separate from a recognition sequence in a secondary probe that directly or indirectly binds the probes or probe sets described herein or a product thereof. In some embodiments, a secondary probe may bind to a barcode sequence in the primary probe. In some aspects, tertiary probes and optionally even higher order probes may be used to target the secondary probes, e.g., at a barcode sequence or complement thereof in a secondary probe or product thereof. In some embodiments, the tertiary probes and/or even higher order probes may comprise one or more barcode sequences and/or one or more detectable labels. In some embodiments, a tertiary probe is a detectably labeled probe that hybridizes to a barcode sequence (or complement thereof) of a secondary probe (or product thereof). In some embodiments, through the detection of signals associated with detectably labeled probes in a sample, the location of one or more analytes in the sample and the identity of the analyte(s) can be determined. In some embodiments, the presence/absence, absolute or relative abundance, an amount, a level, a concentration, an activity, and/or a relation with another analyte of a particular analyte can be analyzed in situ in the sample.

In some embodiments, provided herein are labelling agents (e.g., probes or probe sets), and assay methods to couple target nucleic acid detection, signal amplification (e.g., through nucleic acid amplification such as RCA, and/or hybridization of a plurality of detectably labeled probes, such as in hybridization chain reactions and the like, e.g., described in Section III-C), and decoding of the barcodes.

In some aspects, probes or probe sets described herein, or intermediate probes (e.g., a secondary probe, and/or a higher order probe) can be selected from the group consisting of a circular probe, a circularizable probe, and a linear probe. In some embodiments, a circular probe can be one that is pre-circularized prior to hybridization to a target nucleic acid and/or one or more other probes. In some embodiments, a circularizable probe can be one that can be circularized upon hybridization to a target nucleic acid and/or one or more other probes such as a splint. In some embodiments, a linear probe can be one that comprises a target recognition sequence and a sequence that does not hybridize to a target nucleic acid, such as a 5' overhang, a 3' overhang, and/or a linker or spacer (which may comprise a nucleic acid sequence or a non-nucleic acid moiety). In some embodiments, the sequence (e.g., the 5' overhang, 3' overhang, and/or linker or spacer) is non-hybridizing to the target nucleic acid but may hybridize to one another and/or one or more other probes, such as detectably labeled probes.

Specific probe designs can vary depending on the application. For instance, probes or probe sets described herein (e.g., a primary probe,) or a secondary probe, and/or a higher order probe disclosed herein can comprise a circularizable probe that does not require gap filling to circularize upon hybridization to a template (e.g., a target nucleic acid and/or a probe such as a splint), a gapped circularizable probe (e.g., one that requires gap filling to circularize upon hybridization to a template), an L-shaped probe (e.g., one that comprises a target recognition sequence and a 5' or 3' overhang upon hybridization to a target nucleic acid or a probe), a U-shaped probe (e.g., one that comprises a target recognition sequence, a 5' overhang, and a 3' overhang upon hybridization to a target nucleic acid or a probe), a V-shaped probe (e.g., one that comprises at least two target recognition sequences and a linker or spacer between the target recognition sequences upon hybridization to a target nucleic acid or a probe), a probe or probe set for proximity ligation (such as those described in U.S. Pat. Nos. 7,914,987 and 8,580,504 incorporated herein by reference in their entireties, and probes for Proximity Ligation Assay (PLA) for the simultaneous detection and quantification of nucleic acid molecules and protein-protein interactions), or any suitable combination thereof. In some embodiments, a primary probe, a secondary probe, and/or a higher order probe disclosed herein can comprise a probe that is ligated to itself or another probe using DNA-templated and/or RNA-templated ligation. In some embodiments, a primary probe, a secondary probe, and/or a higher order probe disclosed herein can be a DNA molecule and can comprise one or more other types of nucleotides, modified nucleotides, and/or nucleotide analogues, such as one or more ribonucleotides. In some embodiments, the ligation can be a DNA ligation on a DNA template. In some embodiments, the ligation can be a DNA ligation on an RNA template, and the probes can comprise RNA-templated ligation probes. In some embodiments, a primary probe, a secondary probe, and/or a higher order probe disclosed herein can comprise a padlock-like probe or probe set, such as one described in US 2019/0055594, US 2021/0164039, US 2016/0108458, or US 2020/0224243, each of which is incorporated herein by reference in its entirety. Any suitable combination of the probe designs described herein can be used.

In some embodiments, probes or probe sets described herein (e.g., a primary probe,) or a secondary probe, and/or a higher order probe disclosed herein can comprise two or more parts. In some cases, a probe can comprise one or more features of and/or be modified based on: a split FISH probe or probe set described in WO 2021/167526A1 or Goh et al., "Highly specific multiplexed RNA imaging in tissues with split-FISH," Nat Methods 17(7):689-693 (2020), which are incorporated herein by reference in their entireties; a Z-probe or probe set, such as one described in U.S. Pat. No. 7,709,198 B2, U.S. Pat. No. 8,604,182 B2, U.S. Pat. No. 8,951,726 B2, U.S. Pat. No. 8,658,361 B2, or Tripathi et al., "Z Probe, An Efficient Tool for Characterizing Long Non-Coding RNA in FFPE Tissues," Noncoding RNA 4(3):20 (2018), which are incorporated herein by reference in their entireties; an HCR initiator or amplifier, such as one described in U.S. Pat. No. 7,632,641 B2, US 2017/0009278 A1, U.S. Pat. No. 10,450,599 B2, Dirks and Pierce, "Triggered amplification by hybridization chain reaction," PNAS 101(43):15275-15278 (2004), Chemeris et al., "Real-time hybridization chain reaction," Dokl. Biochem 419:53-55 (2008), Niu et al., "Fluorescence detection for DNA using hybridization chain reaction with enzyme-amplification," Chem Commun (Camb) 46(18):3089-91 (2010), Choi et al., "Programmable in situ amplification for multiplexed imaging of mRNA expression," Nat Biotechnol 28(11):1208-12 (2010), Song et al., "Hybridization chain reaction-based aptameric system for the highly selective and sensitive detection of protein," Analyst 137(6):1396-401 (2012), Choi et al., "Third-generation in situ hybridization chain reaction: multiplexed, quantitative, sensitive, versatile, robust," Development 145(12): dev165753 (2018), or Tsuneoka and Funato, "Modified in situ Hybridization Chain Reaction Using Short Hairpin DNAs," Front Mol Neurosci 13:75 (2020), which are incorporated herein by reference in their entireties; a PLAYR probe or probe set, such as one described in US 2016/0108458 A1 or Frei et al., "Highly multiplexed simultaneous detection of RNAs and proteins in single cells," Nat Methods 13(3):269-75 (2016), which are incorporated herein by reference in their entireties; a PLISH probe or probe set, such as one described in US 2020/0224243 A1 or Nagendran et al., "Automated cell-type classification in intact tissues by single-cell molecular profiling," eLife 7:e30510 (2018), which are incorporated herein by reference in their entireties; a RollFISH probe or probe set such as one described in Wu et al., "RollFISH achieves robust quantification of single-molecule RNA biomarkers in paraffin-embedded tumor tissue samples," Commun Biol 1, 209 (2018), which is hereby incorporated by reference in its entirety; a MERFISH probe or probe set, such as one described in US 2022/0064697 A1 or Chen et al., "Spatially resolved, highly multiplexed RNA profiling in single cells," Science 348(6233):aaa6090 (2015), which are incorporated herein by reference in their entireties; or a primer exchange reaction (PER) probe or probe set, such as one described in US 2019/0106733 A1, which is hereby incorporated by reference in its entirety.

In some embodiments, probes or probe sets described herein comprise one or more features and/or is modified to allow for generation and detection of a first signal that does not comprise a nucleic acid amplification step (e.g., the first signal can be an smFISH signal). In some instances, the probes or probe sets described herein for each target comprises probes directly hybridize to multiple regions (e.g., sequences) of the same transcript. In some embodiments, the probes or probe sets described herein comprise a circular probe or circularizable probe or probe set comprises one or more features and/or is modified to allow for generation and detection of a second signal that comprises an amplification step (e.g., extension and/or amplification catalyzed by a polymerase).

Any suitable circularizable probe or probe set may be used to generate the RCA template which is used to generate the RCA product. By "circularizable" is meant that the probe or reporter (the RCA template) is in the form of a linear molecule having ligatable ends which may circularized by ligating the ends together directly or indirectly, e.g. to each other, or to the respective ends of an intervening ("gap") oligonucleotide or to an extended 3' end of the circularizable RCA template. A circularizable template may also be provided in two or more parts, namely two or more molecules (e.g. oligonucleotides) which may be ligated together to form a circle. When said RCA template is circularizable it is circularized by ligation prior to RCA. Ligation may be templated using a ligation template. The circularizable RCA template (or template part or portion) may comprise at its respective 3' and 5' ends regions of complementarity to corresponding cognate complementary regions (or binding sites) in the ligation template, which may be adjacent where the ends are directly ligated to each other, or non-adjacent, with an intervening "gap" sequence, where indirect ligation is to take place.

In some embodiments, probes or probe sets disclosed herein can be pre-assembled from multiple components, e.g., prior to contacting the probe with a target nucleic acid or a sample. In some embodiments, a nucleic acid probe disclosed herein can be assembled during and/or after contacting a target nucleic acid or a sample with multiple components. In some embodiments, a nucleic acid probe disclosed herein is assembled in situ in a sample. In some embodiments, the multiple components can be contacted with a target nucleic acid or a sample in any suitable order and any suitable combination. For instance, a first component and a second component can be contacted with a target nucleic acid, to allow binding between the components and/or binding between the first and/or second components with the target nucleic acid. Optionally a reaction involving either or both components and/or the target nucleic acid, between the components, and/or between either one or both components and the target nucleic acid can be performed, such as hybridization, ligation, primer extension and/or amplification, chemical or enzymatic cleavage, click chemistry, or any combination thereof. In some embodiments, a third component can be added prior to, during, or after the reaction. In some embodiments, a third component can be added prior to, during, or after contacting the sample with the first and/or second components. In some embodiments, the first, second, and third components can be contacted with the sample in any suitable combination, sequentially or simultaneously. In some embodiments, the nucleic acid probe can be assembled in situ in a stepwise manner, each step with the addition of one or more components, or in a dynamic process where all components are assembled together. One or more removing steps, e.g., by washing the sample such as under stringent conditions, may be performed at any point during the assembling process to remove or destabilize undesired intermediates and/or components at that point and increase the chance of accurate probe assembly and specific target binding of the assembled probe.

In some aspects, the methods provided herein comprise performing rolling circle amplification of a circular probe or a circularized probe generated from a circularizable probe or probe set.

In some embodiments, a probe disclosed herein can comprise a 5' flap which may be recognized by a structure-specific cleavage enzyme, e.g. an enzyme capable of recognizing the junction between a single-stranded 5' overhang and a DNA duplex, and cleaving the single-stranded overhang. It will be understood that the branched three-strand structure which is the substrate for the structure-specific cleavage enzyme may be formed by 5' end of one probe part and the 3' end of another probe part when both have hybridized to a target, as well as by the 5' and 3' ends of a one-part probe. Enzymes suitable for such cleavage include Flap endonucleases (FENS), which are a class of enzymes having endonucleolytic activity and being capable of catalyzing the hydrolytic cleavage of the phosphodiester bond at the junction of single- and double-stranded DNA. Thus, in some embodiment, cleavage of the additional sequence 5' to the first target-specific binding site is performed by a structure-specific cleavage enzyme, e.g. a Flap endonuclease. Suitable Flap endonucleases are described in Ma et al. 2000. *JBC* 275, 24693-24700 and in US 2020/0224244 and may include *P. furiosus* (Pfu), *A. fulgidus* (Afu), *M. jannaschii* (Mja) or *M. thermoautotrophicum* (Mth). In other embodiments an enzyme capable of recognizing and degrading a single-stranded oligonucleotide having a free 5' end may be used to cleave an additional sequence (5' flap) from a structure as described above. Thus, an enzyme having 5' nuclease activity may be used to cleave a 5' additional sequence. Such 5' nuclease activity may be 5' exonuclease and/or 5' endonuclease activity. A 5' nuclease enzyme is capable of recognizing a free 5' end of a single-stranded oligonucleotide and degrading said single-stranded oligonucleotide. A 5' exonuclease degrades a single-stranded oligonucleotide having a free 5' end by degrading the oligonucleotide into constituent mononucleotides from its 5' end. A 5' endonuclease activity may cleave the 5' flap sequence internally at one or more nucleotides. Further, a 5' nuclease activity may take place by the enzyme traversing the single-stranded oligonucleotide to a region of duplex once it has recognized the free 5' end, and cleaving the single-stranded region into larger constituent nucleotides (e.g. dinucleotides or trinucleotides), or cleaving the entire 5' single-stranded region, e.g. as described in Lyamichev et al. 1999. *PNAS* 96, 6143-6148 for Taq DNA polymerase and the 5' nuclease thereof. Preferred enzymes having 5' nuclease activity include Exonuclease VIII, or a native or recombinant DNA polymerase enzyme from *Thermus aquaticus* (Taq), *Thermus thermophilus* or *Thermus flavus*, or the nuclease domain therefrom.

A target sequence for a probe disclosed herein may be comprised in any analyte (e.g., target) disclose herein, including an endogenous analyte (e.g., a viral or cellular nucleic acid), a labelling agent, or a product of an endogenous analyte and/or a labelling agent. In some embodiments, a target sequence for a probe disclosed herein comprises one or more ribonucleotides.

In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some instances, a barcode may be a barcode region. In some embodiments, a barcode comprises two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In some embodiments, barcodes or complements thereof (e.g., barcode sequences or complements thereof comprised by the labelling agents (e.g., probes) disclosed herein or products thereof) can be analyzed (e.g., detected or sequenced) using any suitable method or technique, including those described herein, such as sequencing by synthesis (SBS), sequencing by ligation (SBL), or sequencing by hybridization (SBH). In some instances, barcoding schemes and/or barcode detection schemes as described in RNA sequential probing of targets (RNA SPOTs), single-molecule fluorescent in situ hybridization (smFISH), multiplexed error-robust fluorescence in situ hybridization (MERFISH) or sequential fluorescence in situ hybridization (seqFISH+) can be used. In any of the preceding implementations, the methods provided herein can include analyzing the barcodes by sequential hybridization and detection with a plurality of labelled probes (e.g., detection probes (e.g., detection oligos) or barcode probes). In some instances, the barcode detection steps can be performed as described in hybridization-based in situ sequencing (HybISS). In some instances, probes can be detected and analyzed (e.g., detected or sequenced) as performed in fluorescent in situ sequencing (FISSEQ), or as performed in the detection steps of the spatially-resolved transcript amplicon readout mapping (STARmap) method. In some instances, signals associated with an analyte can be detected as performed in sequential fluorescent in situ hybridization (seqFISH).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5=1024$), whereas 8 nucleotide barcodes can be used to identify up to 65,536 molecular species, a number greater than the total number of distinct genes in the human genome. In some embodiments, the barcode sequences contained in the probes or RCA products are detected, rather than endogenous sequences, which can be an efficient readout in terms of information per cycle of sequencing. Because the barcode sequences are pre-determined, they can also be designed to feature error detection and correction mechanisms, see, e.g., U.S. Pat. Pub. 20190055594 and U.S. Pat. Pub. 20210164039, which are hereby incorporated by reference in their entirety.

d. Detection

Provided herein are a plurality of detectable probes contacted with the biological sample for detecting a plurality of signals associated with a plurality of targets in the biological sample. In some embodiments, the detectable probes are detectably labeled or comprise a detectable label. The terms "label" and "detectable label" comprise a directly or indirectly detectable moiety that is associated with (e.g., conjugated to) a molecule to be detected, e.g., a nucleic acid molecule that comprises a detectable label. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes (radioactive isotopes), fluorophores, fluorescers, chemiluminescent compounds, bioluminescent compounds, dyes, enzymes, enzyme substrates, enzyme cofactors, enzyme inhibitors, chromophores, dyes, metal ions, metal sols, ligands (e.g., biotin or haptens) and the like.

In some aspects, the detectable label comprises a luminophore. In some embodiments, the luminophore is a fluorophore. The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa dyes (AlexaFluors), fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, *Renilla* luciferase, NADPH, beta-galactosidase, horseradish peroxidase, glucose oxidase, alkaline phosphatase, chloramphenical acetyl transferase, and urease.

In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DiIC18(5)), DIDS, DiI (DiIC18(3)), DiO (DiOC18(3)), DiR (DiIC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen®#2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas RedY-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

In some embodiments, the detectable label comprises an infrared fluorophore. An "infrared fluorophore" emits infrared light. In some embodiments, the infrared fluorophore has a longer excitation wavelength than a traditional fluorophore.

Examples of detectable labels comprise, but are not limited to, various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}$I, $^{35}$S, $^{14}$C, or $^{3}$H. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264. As used herein, the term "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

In some embodiments, one or more detectable labels can be attached to a labelling agent or nucleic acid probe disclosed herein. The one or more detectable labels can be incorporated during nucleic acid polymerization or amplification (e.g., Cy5®-labeled nucleotides, such as Cy5®-dCTP). Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.). Methods for custom synthesis of nucleotides having other fluorophores can include those described in Henegariu et al. (2000) Nature Biotechnol. 18:345, incorporated herein by reference.

In some embodiments, one or more detectable labels can be attached via post-synthetic attachment. Fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62)

Biotin, or a derivative thereof, may also be used as a label on a nucleic acid molecule, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. As used herein, the term antibody refers to an antibody molecule of any class, or any sub-fragment thereof, such as an Fab.

Other suitable labels for use in the methods provided herein may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleic acid molecule (e.g., detectable probe) can be indirectly labeled, especially with a hapten that is then bound by a capture agent, e.g., as disclosed in U.S. Pat. Nos. 5,344,757, 5,702,888, 5,354,657, 5,198,537 and 4,849,336, and 5,073,562, each of which is herein incorporated by reference in its entirety. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

In some embodiments, the detectable label is detected in situ. The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some aspects, the method includes detection of the probe or probe set hybridized to the target (e.g., target sequence) or any products generated therefrom or a derivative thereof. In any of the embodiments herein, the method can further comprise imaging the biological sample to detect a ligation product or a circularized probe or product thereof. In any of the embodiments herein, a sequence of the ligation product, rolling circle amplification product, or other generated product can be analyzed in situ in the biological sample. In any of the embodiments herein, the imaging can comprise detecting a signal associated with a fluorescently labeled probe that directly or indirectly binds to a rolling circle amplification product of the circularized probe. In any of the embodiments herein, the sequence of the sequence of the ligation product, rolling circle amplification product, or other generated product can be analyzed by sequential hybridization, sequencing by hybridization, sequencing by ligation, sequencing by synthesis, sequencing by binding, or a combination thereof.

In any of the embodiments herein, a sequence associated with the target nucleic acid or the probes or probe sets described herein can comprise one or more barcode sequences or complements thereof. In any of the embodiments herein, the sequence of the rolling circle amplification product can comprise one or more barcode sequences or complements thereof. In any of the embodiments herein, a probe can comprise one or more barcode sequences or complements thereof. In any of the embodiments herein, the one or more barcode sequences can comprise a barcode sequence corresponding to the target nucleic acid. In any of the embodiments herein, the one or more barcode sequences can comprise a barcode sequence corresponding to the sequence of interest, such as variant(s) of a single nucleotide of interest.

In any of the embodiments herein, the detecting step can comprise contacting the biological sample with one or more detectable probes that directly or indirectly hybridize to the rolling circle amplification product, and dehybridizing the one or more detectable probes from the rolling circle amplification product. In any of the embodiments herein, the contacting and dehybridizing steps can be repeated with the one or more detectable probes and/or one or more other detectable probes that directly or indirectly hybridize to the rolling circle amplification product.

In any of the embodiments herein, the detecting step can comprise contacting the biological sample with one or more first detectable probes that directly hybridize to the plurality of probes or probe sets. In some instances, the detecting step can comprise contacting the biological sample with one or more first detectable probes that indirectly hybridize to the plurality of probes or probe sets. In any of the embodiments herein, the detecting step can comprise contacting the biological sample with one or more first detectable probes that directly or indirectly hybridize to the plurality of probes or probe sets.

In any of the embodiments herein, the detecting step can comprise contacting the biological sample with one or more intermediate probes that directly or indirectly hybridize to the plurality of probes or probe sets, rolling circle amplification product generated using the plurality of probes or probe sets, wherein the one or more intermediate probes are detectable using one or more detectable probes. In any of the embodiments herein, the detecting step can further comprise dehybridizing the one or more intermediate probes and/or the one or more detectable probes from the rolling circle amplification product or the plurality of probes or probe sets. In any of the embodiments herein, the contacting and dehybridizing steps can be repeated with the one or more intermediate probes, the one or more detectable probes, one or more other intermediate probes, and/or one or more other detectable probes.

In some embodiments, the detection may be spatial, e.g., in two or three dimensions. In some embodiments, the detection may be quantitative, e.g., the amount or concentration of a primary nucleic acid probe (and of a target nucleic acid) may be determined. In some embodiments, the plurality of probes or probe sets (e.g., primary probes), secondary probes, higher order probes, and/or detectable probes may comprise any of a variety of entities able to hybridize a nucleic acid, e.g., DNA, RNA, LNA, and/or PNA, etc., depending on the application.

In some embodiments, a method disclosed herein may also comprise one or more signal amplification components.

In some embodiments, the present disclosure relates to the detection of nucleic acids sequences in situ using probe hybridization and generation of amplified signals associated with the probes, wherein background signal is reduced and sensitivity is increased. In some embodiments, the RCA product generated using a method disclosed herein can be detected in with a method that comprises signal amplification. In some embodiments, signal amplification may comprise use of the plurality of probes or probe sets.

Exemplary signal amplification methods include targeted deposition of detectable reactive molecules around the site of probe hybridization, targeted assembly of branched structures (e.g., bDNA or branched assay using locked nucleic acid (LNA)), programmed in situ growth of concatemers by enzymatic rolling circle amplification (RCA) (e.g., as described in US 2019/0055594 incorporated herein by reference), hybridization chain reaction, assembly of topologically catenated DNA structures using serial rounds of chemical ligation (clampFISH), signal amplification via hairpin-mediated concatemerization (e.g., as described in US 2020/0362398 incorporated herein by reference), e.g., primer exchange reactions such as signal amplification by exchange reaction (SABER) or SABER with DNA-Exchange (Exchange-SABER). In some embodiments, a non-enzymatic signal amplification method may be used.

The detectable reactive molecules may comprise tyramide, such as used in tyramide signal amplification (TSA) or multiplexed catalyzed reporter deposition (CARD)-FISH. In some embodiments, the detectable reactive molecule may be releasable and/or cleavable from a detectable label such as a fluorophore. In some embodiments, a method disclosed herein comprises multiplexed analysis of a biological sample comprising consecutive cycles of probe hybridization, fluorescence imaging, and signal removal, where the signal removal comprises removing the fluorophore from a fluorophore-labeled reactive molecule (e.g., tyramide). Exemplary detectable reactive reagents and methods are described in U.S. Pat. No. 6,828,109, US 2019/0376956, US 2019/0376956, US 2022/0026433, US 2022/0128565, and US 2021/0222234, all of which are incorporated herein by reference in their entireties.

In some embodiments, hybridization chain reaction (HCR) can be used for signal amplification. HCR is an enzyme-free nucleic acid amplification based on a triggered chain of hybridization of nucleic acid molecules starting from HCR monomers, which hybridize to one another to form a nicked nucleic acid polymer. This polymer is the product of the HCR reaction which is ultimately detected in order to indicate the presence of the target analyte. HCR is described in detail in Dirks and Pierce, 2004, PNAS, 101 (43), 15275-15278 and in U.S. Pat. Nos. 7,632,641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401). HCR monomers typically comprise a hairpin, or other metastable nucleic acid structure. In the simplest form of HCR, two different types of stable hairpin monomer, referred to here as first and second HCR monomers, undergo a chain reaction of hybridization events to form a long nicked double-stranded DNA molecule when an "initiator" nucleic acid molecule is introduced. The HCR monomers have a hairpin structure comprising a double stranded stem region, a loop region connecting the two strands of the stem region, and a single stranded region at one end of the double stranded stem region. The single stranded region which is exposed (and which is thus available for hybridization to another molecule, e.g. initiator or other HCR monomer) when the monomers are in the hairpin structure may be known as the "toehold region" (or "input domain"). The first HCR monomers each further comprise a sequence which is complementary to a sequence in the exposed toehold region of the second HCR monomers. This sequence of complementarity in the first HCR monomers may be known as the "interacting region" (or "output domain"). Similarly, the second HCR monomers each comprise an interacting region (output domain), e.g. a sequence which is complementary to the exposed toehold region (input domain) of the first HCR monomers. In the absence of the HCR initiator, these interacting regions are protected by the secondary structure (e.g. they are not exposed), and thus the hairpin monomers are stable or kinetically trapped (also referred to as "metastable"), and remain as monomers (e.g. preventing the system from rapidly equilibrating), because the first and second sets of HCR monomers cannot hybridize to each other. However, once the initiator is introduced, it is able to hybridize to the exposed toehold region of a first HCR monomer, and invade it, causing it to open up. This exposes the interacting region of the first HCR monomer (e.g. the sequence of complementarity to the toehold region of the second HCR monomers), allowing it to hybridize to and invade a second HCR monomer at the toehold region. This hybridization and invasion in turn opens up the second HCR monomer, exposing its interacting region (which is complementary to the toehold region of the first HCR monomers), and allowing it to hybridize to and invade another first HCR monomer. The reaction continues in this manner until all of the HCR monomers are exhausted (e.g. all of the HCR monomers are incorporated into a polymeric chain). Ultimately, this chain reaction leads to the formation of a nicked chain of alternating units of the first and second monomer species. The presence of the HCR initiator is thus required in order to trigger the HCR reaction by hybridization to and invasion of a first HCR monomer. The first and second HCR monomers are designed to hybridize to one another are thus may be defined as cognate to one another. They are also cognate to a given HCR initiator sequence. HCR monomers which interact with one another (hybridize) may be described as a set of HCR monomers or an HCR monomer, or hairpin, system.

An HCR reaction could be carried out with more than two species or types of HCR monomers. For example, a system involving three HCR monomers could be used. In such a system, each first HCR monomer may comprise an interacting region which binds to the toehold region of a second HCR monomer; each second HCR may comprise an interacting region which binds to the toehold region of a third HCR monomer; and each third HCR monomer may comprise an interacting region which binds to the toehold region of a first HCR monomer. The HCR polymerization reaction would then proceed as described above, except that the resulting product would be a polymer having a repeating unit of first, second and third monomers consecutively. Corresponding systems with larger numbers of sets of HCR monomers could readily be conceived.

In some embodiments, similar to HCR reactions that use hairpin monomers, linear oligo hybridization chain reaction (LO-HCR) can also be used for signal amplification. In some embodiments, provided herein is a method of detecting an analyte in a sample comprising: (i) performing a linear oligo hybridization chain reaction (LO-HCR), wherein an initiator is contacted with a plurality of LO-HCR monomers of at least a first and a second species to generate a polymeric LO-HCR product hybridized to a target nucleic acid molecule, wherein the first species comprises a first hybridization region complementary to the initiator and a second hybridization region complementary to the second species, wherein the first species and the second species are linear, single-stranded nucleic acid molecules; wherein the initiator is provided in one or more parts, and hybridizes directly or indirectly to or is comprised in the target nucleic acid molecule; and (ii) detecting the polymeric product, thereby detecting the analyte. In some embodiments, the first species and/or the second species may not comprise a hairpin structure. In some embodiments, the plurality of LO-HCR monomers may not comprise a metastable secondary structure. In some embodiments, the LO-HCR polymer may not comprise a branched structure. In some embodiments, performing the linear oligo hybridization chain reaction comprises contacting the target nucleic acid molecule with the initiator to provide the initiator hybridized to the target nucleic acid molecule. In any of the embodiments herein, the target nucleic acid molecule and/or the analyte can be an RCA product. Exemplary methods and compositions for LO-HCR are described in US 2021/0198723, incorporated herein by reference in its entirety.

In some embodiments, detection of nucleic acids sequences in situ may comprise an assembly for branched signal amplification. In some embodiments, the assembly complex comprises an amplifier hybridized directly or indirectly (via one or more oligonucleotides) to a probe or probe set. In some embodiments, the assembly includes one or more amplifiers each including an amplifier repeating sequence. In some aspects, the one or more amplifiers is labeled. Described herein is a method of using the aforementioned assembly, including for example, using the assembly in multiplexed error-robust fluorescent in situ hybridization (MERFISH) applications, with branched DNA amplification for signal readout. In some embodiments, the amplifier repeating sequence is about 5-30 nucleotides, and is repeated N times in the amplifier. In some embodiments, the amplifier repeating sequence is about 20 nucleotides, and is repeated at least two times in the amplifier. In some aspects, the one or more amplifier repeating sequence is labeled. For exemplary branched signal amplification, see e.g., U.S. Pat. Pub. No. US20200399689A1 and Xia et al., Multiplexed Detection of RNA using MERFISH and branched DNA amplification. Scientific Reports (2019), each of which is fully incorporated by reference herein.

In some embodiments, the plurality of probes or probe sets can be detected in with a method that comprises signal amplification by performing a primer exchange reaction (PER). In various embodiments, a primer with domain on its 3' end binds to a catalytic hairpin, and is extended with a new domain by a strand displacing polymerase. For example, a primer with domain 1 on its 3' ends binds to a catalytic hairpin, and is extended with a new domain 1 by a strand displacing polymerase, with repeated cycles generating a concatemer of repeated domain 1 sequences. In various embodiments, the strand displacing polymerase is Bst. In various embodiments, the catalytic hairpin includes a stopper which releases the strand displacing polymerase. In various embodiments, branch migration displaces the extended primer, which can then dissociate. In various embodiments, the primer undergoes repeated cycles to form a concatemer primer. In various embodiments, a plurality of concatemer primers is contacted with a sample comprising the plurality of probes or probe sets described herein. In various embodiments, the plurality of probes or probe sets may be contacted with a plurality of concatemer primers and a plurality of labeled probes. see e.g., U.S. Pat. Pub. No.

US20190106733, which is incorporated herein by reference, for exemplary molecules and PER reaction components.

In some embodiments, the methods comprise sequencing all or a portion of the amplification product, such as one or more barcode sequences present in the amplification product, e.g., via DNA sequencing.

In some embodiments, the analysis and/or sequence determination comprises sequencing all or a portion of the amplification product or the probe(s) and/or in situ hybridization to the amplification product or the probe(s). In some embodiments, the sequencing step involves sequencing by hybridization, sequencing by ligation, and/or fluorescent in situ sequencing, hybridization-based in situ sequencing and/or wherein the in situ hybridization comprises sequential fluorescent in situ hybridization. In some embodiments, the analysis and/or sequence determination comprises detecting a polymer generated by a hybridization chain reaction (HCR) reaction, see e.g., US 2017/0009278, which is incorporated herein by reference, for exemplary probes and HCR reaction components. In some embodiments, the detection or determination comprises hybridizing to the amplification product a detection oligonucleotide labeled with a fluorophore, an isotope, a mass tag, or a combination thereof. In some embodiments, the detection or determination comprises imaging the amplification product. In some embodiments, the target nucleic acid is an mRNA in a tissue sample, and the detection or determination is performed when the target nucleic acid and/or the amplification product is in situ in the tissue sample.

In some aspects, the provided methods comprise imaging the amplification product (e.g., amplicon) and/or one or more portions of the plurality of probes or probe sets, for example, via binding of the detection probe and detecting the detectable label. In some embodiments, the detection probe comprises a detectable label that can be measured and quantitated. The terms "label" and "detectable label" comprise a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

In some embodiments, a detectable probe containing a detectable label can be used to detect the plurality of probes or probe sets and/or amplification products (e.g., amplicon) described herein. In some embodiments, the methods involve incubating the detectable probe containing the detectable label with the sample, washing unbound detectable probe, and detecting the label, e.g., by imaging.

In some aspects, the detecting comprises performing microscopy, scanning mass spectrometry or other imaging techniques described herein. In such aspects, the detecting comprises determining a signal, e.g., a fluorescent signal. In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequencing can be performed in situ. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (e.g., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) Anal. Biochem. 320, 55-65, and Lee et al., (2014) Science, 343(6177), 1360-1363. In addition, examples of methods and systems for performing in situ sequencing are described in US 2016/0024555, US 2019/0194709, and in U.S. Pat. Nos. 10,138,509, 10,494,662 and 10,179,932. Exemplary techniques for in situ sequencing comprise, but are not limited to, STARmap (described for example in Wang et al., (2018) Science, 361(6499) 5691), MERFISH (described for example in Moffitt, (2016) Methods in Enzymology, 572, 1-49), hybridization-based in situ sequencing (HybISS) (described for example in Gyllborg et al., Nucleic Acids Res (2020) 48(19):e112, and FISSEQ (described for example in US 2019/0032121). In some cases, sequencing can be performed after the analytes are released from the biological sample.

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/005986, US 2005/0100900, U.S. Pat. No. 9,217,178, US 2009/0118128, US 2012/0270305, US 2013/0260372, and US 2013/0079232.

In some embodiments, sequence analysis of nucleic acids (e.g., nucleic acids such as RCA products comprising barcode sequences) can be performed by sequential hybridization (e.g., sequencing by hybridization and/or sequential in situ fluorescence hybridization). Sequential fluorescence hybridization can involve sequential hybridization of detection probes comprising an oligonucleotide and a detectable label. In some embodiments, a method disclosed herein comprises sequential hybridization of the detectable probes disclosed herein, including detectably labeled probes (e.g., fluorophore conjugated oligonucleotides) and/or probes that are not detectably labeled per se but are capable of binding (e.g., via nucleic acid hybridization) and being detected by detectably labeled probes. Exemplary methods comprising sequential fluorescence hybridization of detectable probes are described in US 2019/0161796, US 2020/0224244, US 2022/0010358, US 2021/0340618, and WO 2021/138676, all of which are incorporated herein by reference.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597.

In some embodiments, the barcodes of the probes (e.g., plurality of probes or probe sets) or complements or products thereof are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed (e.g., detected or sequenced) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides or detectable probes). Exemplary decoding schemes are described in Eng et al., "Transcriptome-scale Super-Resolved Imaging in Tissues by RNA SeqFISH+," *Nature* 568(7751):235-239 (2019); Chen et al., *Science*; 348(6233):aaa6090 (2015); Gyllborg et al., Nucleic Acids Res (2020) 48(19):e112; U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

In some aspects, the provided embodiments can be applied to an in situ method of analyzing target nucleic acid sequences (e.g., RNAs) and/or other targets (e.g., proteins) in intact tissues or samples in which the spatial information has been preserved. In some aspects, the embodiments can be applied in an imaging or detection method for multiplexed analysis of nucleic acids and/or other targets (e.g., proteins). In some aspects, the provided embodiments can be used to identify or detect regions and/or sequences of interest in target nucleic acids.

In some cases, analysis is performed on one or more images captured, and may comprise processing the image(s) and/or quantifying signals observed. In some embodiments, a method disclosed herein comprises multiplexed analysis of a biological sample comprising consecutive cycles of probe hybridization, fluorescence imaging, and probe removal. In some embodiments, images of signals from different fluorescent and/or non-fluorescent channels and/or detectable probe hybridization cycles can be compared and analyzed. In some embodiments, images of signals (or absence thereof) at a particular location in a sample from different fluorescent channels and/or sequential detectable probe hybridization cycles can be aligned to analyze an analyte at the location. For instance, a particular location in a sample can be tracked and signal spots from sequential hybridization cycles can be analyzed to detect a target polynucleotide sequence (e.g., an associated barcode sequence or subsequence thereof) at the location. The analysis may comprise processing information of one or more cell types, one or more types of analytes, a number or level of analyte, and/or a number or level of cells detected in a particular region of the sample. In some embodiments, the analysis comprises detecting a sequence e.g., a barcode sequence present in an amplification product at a location in the sample. In some embodiments, the analysis includes quantification of puncta (e.g., if amplification products are detected). In some cases, the analysis includes determining whether particular cells and/or signals are present that correlate with one or more analytes from a particular panel. In some instances, the analysis includes using single cell segmentation and resolution to determine cell type frequencies in a region of interest of a sample. In some embodiments, the obtained information may be compared to a positive and negative control, to another selected region of interest, or to a threshold of a feature to determine if the region of interest exhibits a certain feature or phenotype. In some cases, the information may comprise signals from a cell, a region, and/or comprise readouts from multiple detectable labels. In some case, the analysis further includes displaying the information from the analysis or detection step. In some embodiments, software may be used to automate the processing, analysis, and/or display of data.

IV. Samples and Sample Processing

A sample disclosed herein can be or derived from any biological sample. Methods, probes, and kits disclosed herein may be used for analyzing a biological sample, which may be obtained from a subject using any of a variety of techniques including, but not limited to, biopsy, surgery, and laser capture microscopy (LCM), and generally comprises cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

In some embodiments, the sample is a cell pellet or cell block. In some embodiments, the biological sample comprises a tissue sample. In some instances, the tissue sample is a tissue biopsy. In some instances, the biological sample is a tumor biopsy. In some instances, the biological sample is a surgical resection. In some instances, the biological sample comprises a tumor or a portion of a tumor.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or circularizable probe (e.g., a padlock probe). In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a circularizable probe or probe set.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., Science 347(6221):543-548, 2015, the entire contents of which are incorporated herein by reference.

(v) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multi-plexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al.,

*J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other hydrogel-formation method. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel comprises a hybrid material, e.g., the hydrogel material comprises elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate comprises a hydrogel and one or more second materials. In some embodiments, the hydrogel is placed on top of one or more second materials. For example, the hydrogel can be preformed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/ or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of molecular cross-links in the reversibly cross-linked biological sample are de-crosslinked.

(viii) Tissue Permeabilization and Treatment

In some embodiments, a biological sample can be permeabilized to facilitate transfer of species (such as probes) into the sample. If a sample is not permeabilized sufficiently, probes that enter the sample and bind to analytes therein may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods that can be used herein include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to open up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

In some aspects, when two or more analytes are analyzed, a first and second probe that is specific for (e.g., specifically hybridizes to) each RNA or cDNA analyte are used. For example, in some embodiments of the methods provided herein, templated ligation is used to detect gene expression in a biological sample. An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics*, 15 401, (2014), the entire contents of which are incorporated herein by reference). Furthermore, hydroxyapatite chromatography can remove abundant species (e.g., rRNA) (see, e.g., Vandernoot, V.A., cDNA normalization by hydroxyapatite chromatography to enrich transcriptome diversity in RNA-seq applications, *Biotechniques*, 53(6) 373-80, (2012), the entire contents of which are incorporated herein by reference).

V. Compositions and Kits

In some embodiments, provided herein are kits, for example comprising a compound disclosed herein (e.g., in Section II-C) for catalytic de-crosslinking of a fixed biological sample. In some embodiments, the compound is provided in a composition (e.g., a composition comprising DMSO) and the kit can further comprise one or more other compositions, e.g., a buffer for the compound. In some examples, a solution or a suspension comprising the catalyst and a buffer is provided. In some instances, the buffer comprises citrate, tris(hydroxymethyl)aminomethane (Tris), phosphate-buffered saline (PBS), 2-[4-(2-hydroxyethyl)piperazin-1-yl]ethanesulfonic acid (HEPES), 2-(N-morpholino)ethanesulfonic acid (MES), or a combination thereof. In some instances, the solution or suspension comprises sodium dodecyl sulfate (SDS), urea, and/or a proteinase (e.g., proteinase K). The kits can comprise one or more reagents required for one or more steps comprising hybridization, ligation, extension, detection, and/or sample preparation as described herein. In some embodiments, the kit comprises one or more labelling agents, e.g., disclosed in Section III-B and Section III-C. In some embodiments, the kit comprises one or more oligonucleotides, e.g., nucleic acid probes disclosed in Section III-B and Section III-C, for detecting one or more nucleic acid analytes and/or one or more non-nucleic acid analytes. In some embodiments, the kit comprises one or more antibodies (e.g., for detecting protein analytes) which can be optionally labelled with a detectable label such as a fluorophore and/or a reporter oligonucleotide.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing (e.g., crosslinking), embedding, and/or permeabilizing the biological sample. In some embodiments, the kits contain reagents, such as enzymes and buffers. In some aspects, the kit can also comprise any of the reagents described herein, e.g., wash buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, and reagents for additional assays.

VI. Applications

In some aspects, the provided embodiments can be applied in an in situ method of analyzing nucleic acid sequences, such as fluorescent in situ hybridization (FISH)-based methods, in situ transcriptomic analysis or in situ sequencing, for example from intact tissues or samples in which the spatial information has been preserved. In some aspects, the embodiments can be applied in an imaging or detection method for multiplexed nucleic acid analysis. In some aspects, the provided embodiments can be used to detect a signal associated with a detectable label of a nucleic acid probe that is hybridized to a target sequence of a target nucleic acid in a biological sample.

In some embodiments, the target nucleic acid comprises a single-nucleotide polymorphism (SNP). In some embodiments, the target nucleic acid comprises is a single-nucleotide variant (SNV). In some embodiments, the target nucleic acid comprises a single-nucleotide substitution. In some embodiments, the target nucleic acid comprises a point mutation. In some embodiments, the target nucleic acid comprises a single-nucleotide insertion.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

In some aspects, the embodiments can be applied to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, or in personalized medicine or ancestry.

VII. Terminology

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms "polynucleotide," "polynucleotide," and "nucleic acid molecule", used interchangeably herein, refer to polymeric forms of nucleotides of any length, either ribonucleotides or deoxyribonucleotides. Thus, this term comprises, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, e.g., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., Biochemistry, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Sequencing," "sequence determination" and the like means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput digital sequencing" or "next generation sequencing" means sequence determination using methods that determine many (typically thousands to billions) of nucleic acid sequences in an intrinsically parallel manner, e.g. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeq™ technology by Illumina, Inc., San Diego, Calif.; HeliScope™ by Helicos Biosciences Corporation, Cambridge, Ma.; and PacBio RS by Pacific Biosciences of California, Inc., Menlo Park, Calif.), sequencing by ion detection technologies (such as Ion Torrent™ technology, Life Technologies, Carlsbad, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

"Multiplexing" or "multiplex assay" herein may refer to an assay or other analytical method in which the presence and/or amount of multiple targets, e.g., multiple nucleic acid target sequences, can be assayed simultaneously by using more than one probe, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

The term "about" as used herein refers to the usual error range for the respective value readily known to the skilled person in this technical field. Reference to "about" a value or parameter herein comprises (and describes) embodiments that are directed to that value or parameter per se.

As used herein, the singular forms "a," "an," and "the" comprise plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be comprised in the smaller ranges, and are also encompassed within the claimed subject matter, subject to any specifically excluded limit in the stated range. Where the stated range comprises one or both of the limits, ranges excluding either or both of those comprised limits are also comprised in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

VIII. Examples

The following examples are included for illustrative purposes only and are not intended to limit the scope of the present disclosure.

Example 1: FFPE Sample Preparation, De-Paraffinization, and De-Crosslinking

A formalin-fixed, paraffin-embedded (FFPE) tissue sample was cut into thin tissue sections using a pre-warmed microtome. The sections were placed on slides and dried at a temperature higher than room temperature, followed by overnight drying at room temperature in a desiccator. Images of the sections were taken for record, e.g., in order to monitor tissue morphology and/or detachment during sample processing. In some instances, images of the sections taken after de-crosslinking were compared to those before de-crosslinking.

The slides were baked uncovered in an oven, and then calibrated to room temperature. The sections were de-paraffinized and dehydrated using xylene and absolute ethanol. The sections were then re-hydrated using an ethanol series (e.g., 96% ethanol followed by 70% ethanol), and then re-hydrated in nuclease free water (e.g., DEPC water). The slides were gently dried to allow application of a cassette to seal around the tissue sections, without letting the tissue section to dry completely.

The sections were then de-crosslinked using a catalyst disclosed herein in a buffer solution. In some instances, the a de-crosslinking buffer can function as an antigen retriever buffer. Then the sections were washed three times with RNase-free phosphate-buffered saline (PBS) or PBST (phosphate-buffered saline solution with a low-concentration detergent solution, e.g., 0.05% to 0.1% Tween™ 20) prior to application of labelling agents (e.g., detectable nucleic acid probes for nucleic acids and/or labelled antibodies for proteins) to the tissue samples.

Example 2: Analyte Detection in De-Crosslinked FFPE Human Breast Cancer Samples FFPE human breast cancer tissues were sectioned to 5 μm thickness, transferred to Superfrost® Plus slides, and processed essentially as described in Example 1. Specifically, 2-amino-5-methylbenzoic acid (Compound 1) was used as the de-crosslinking agent and applied to de-paraffinized and re-hydrated samples in a buffer solution, such as a solution of citrate buffer at pH 6 or a solution of Tris-EDTA (TE) buffer at pH 9. The samples were incubated under various de-crosslinking temperatures (e.g., 80° C. or 95° C.) for various time periods (e.g., 15 minutes or 30 minutes). Different concentrations of the de-crosslinking agent in the buffer solutions were tested, including 0 mM, 50 mM, 100 mM, 200 mM, and 400 mM of Compound 1.

The de-crosslinked and washed tissue samples can be immediately used for analyte detection. In some instances, circularizable probes (e.g., padlock probes) targeting MALAT-1/ACTB (nuclear/cytoplasmic) or GAPDH/RPLP0 (cytoplasmic) RNA transcripts were added in hybridization buffers (e.g., including SSC and formamide) and incubated with the samples to allow hybridization of the circularizable probes to their target nucleic acids. In addition to a target hybridization region, each circularizable probe also contained a common anchor region and a barcode region. Then, the probe hybridization mixture was removed and the samples were washed. For ligation of the circularizable probes hybridized to their target nucleic acids, a ligation reaction mix (e.g., containing a SplintR® ligase buffer, RNase inhibitor and SplintR® ligase) and a rolling circle amplification (RCA) primer were added to the samples and incubated for probe circularization and RCA primer hybridization to the probes. The samples were washed and an RCA reaction mixture (containing Phi29 reaction buffer, dNTPs, Phi29 polymerase) was added and incubated for RCA of the circularized probes.

The samples were washed (e.g., in PBST) and detectable probes in a hybridization buffer (e.g., containing SSC and formamide) were hybridized to RCA products (RCPs) in the sample. The detectable probes included probes that hybridize to sequences (e.g., barcode sequences or anchor sequences) in the RCPs and comprise overhangs for hybridization of fluorescently labelled detection oligonucleotides. The samples were imaged in fluorescent microscope with 40× objective and the signals associated with the RCPs were quantified using a software. In some instances, the samples were also stained with DAPI and/or labelled antibodies, e.g., fluorescently labelled anti-Vimentin antibody or anti-panCK antibody. In some instances, once the samples were imaged to detect signals associated with the detectable probes or labelled antibodies, the samples were stripped (e.g., using a denaturing agent) and contacted with additional detectable probes or labelled antibodies for the next imaging round.

Figure 4:
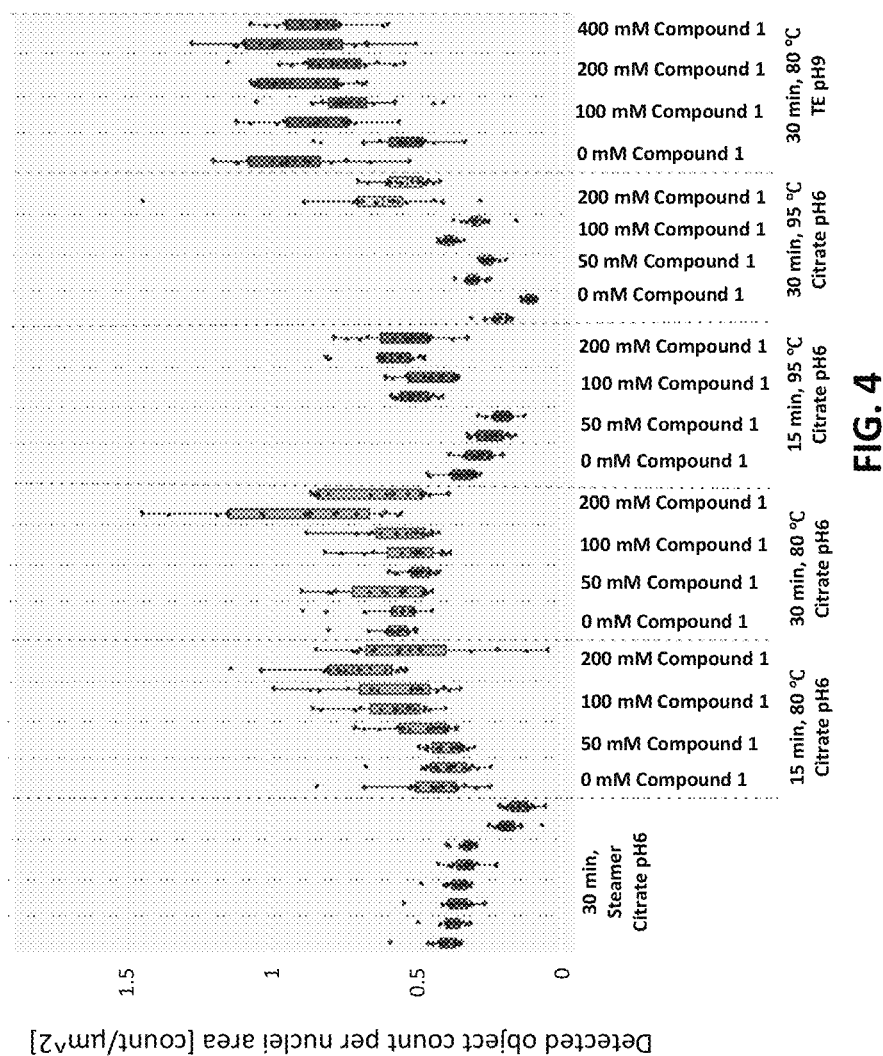
FIG. 4 shows detected rolling circle amplification product (RCP) signal density (count/$\mu m^2$ nuclei area) in catalytically de-crosslinked human breast cancer samples compared to control samples de-crosslinked using a steamer.

FIG. 4 shows the detected object count per nucleic area (RCP count/$\mu m^2$ nuclei area) in cells of the human breast cancer samples treated with Compound 1 for de-crosslinking under various combinations of the de-crosslinking temperature (80° C. or 95° C.), time (15 minutes or 30 minutes), buffer (Citrate or TE), and catalyst concentration (0 mM, 50 mM, 100 mM, 200 mM, or 400 mM). The RCPs were detected using detectable probes targeting the common anchor region in the RCPs. For instance, de-crosslinking for 30 minutes under 80° C., at 100 mM Compound 1 in either the citrate buffer (pH 6) or the TE buffer (pH 9) appeared to significantly improve the detection of RCPs, as reflected by the increased detected object counts per nucleic area as compared to control (de-crosslinked in a steamer for 30 minutes using citrate buffer (pH 6)). In some instances, catalytic de-crosslinking appeared to boost sensitivity and RCP brightness using citrate buffer and between about 100 and about 200 mM of Compound 1. RCP detection using detectable probes targeting MALAT-1/ACTB and RCP detection using detectable probes targeting GAPDH/RPLP0 showed similar results (data not shown).

FIGS. 5A-5B show representative images of anti-panCK antibody staining in a control sample (de-crosslinked in a steamer) and in samples de-crosslinked using the indicated de-crosslinking temperature, time, and catalyst concentration in either the citrate buffer (FIG. 5A) or the TE buffer (FIG. 5B). These results indicate that antibody staining (e.g., antibody positive signal intensity) may be improved by catalytic de-crosslinking with various concentrations of Compound 1 in citrate or TE buffer.

FIG. 6 shows representative DPAI images of the tissue samples de-crosslinked in a thermal cycler (using citrate buffer, pH 6) at various combinations of temperature and time, either in the absence of the catalyst (0 mM) or using 200 mM of the catalyst. These results demonstrate that at certain concentrations the de-crosslinking agent can improve tissue integrity and/or adhesion (e.g., reduce waviness and/or tissue detachment from the substrate).

Together these results demonstrate that catalytic de-crosslinking (e.g., at relatively lower temperatures such as 80° C.) can improve signal detection of nucleic acids and proteins in FFPE human breast cancer tissues in situ without compromising tissue integrity and/or adhesion.

Example 3: Analyte Detection in De-Crosslinked FFPE Samples from Various Tissues FFPE human breast cancer, melanoma, lymph node, lung cancer, and normal lung tissues were processed essentially as described in Example 1. Specifically, 2-amino-5-methylbenzoic acid (Compound 1) or (4-aminopyridin-3-yl)phosphonic acid (Compound 8) was used as the de-crosslinking agent and applied to de-paraffinized and re-hydrated samples in a buffer solution, such as a solution of citrate buffer at pH 6 or a solution of TE buffer at pH 9. The samples were incubated under various de-crosslinking temperatures (e.g., 80° C. or 95° C.) for 30 minutes, using 0 mM or 200 mM of Compound 1 or Compound 8. Analytes in the de-crosslinked tissue samples were detected essentially as described in Example 2.

Figure 7A:
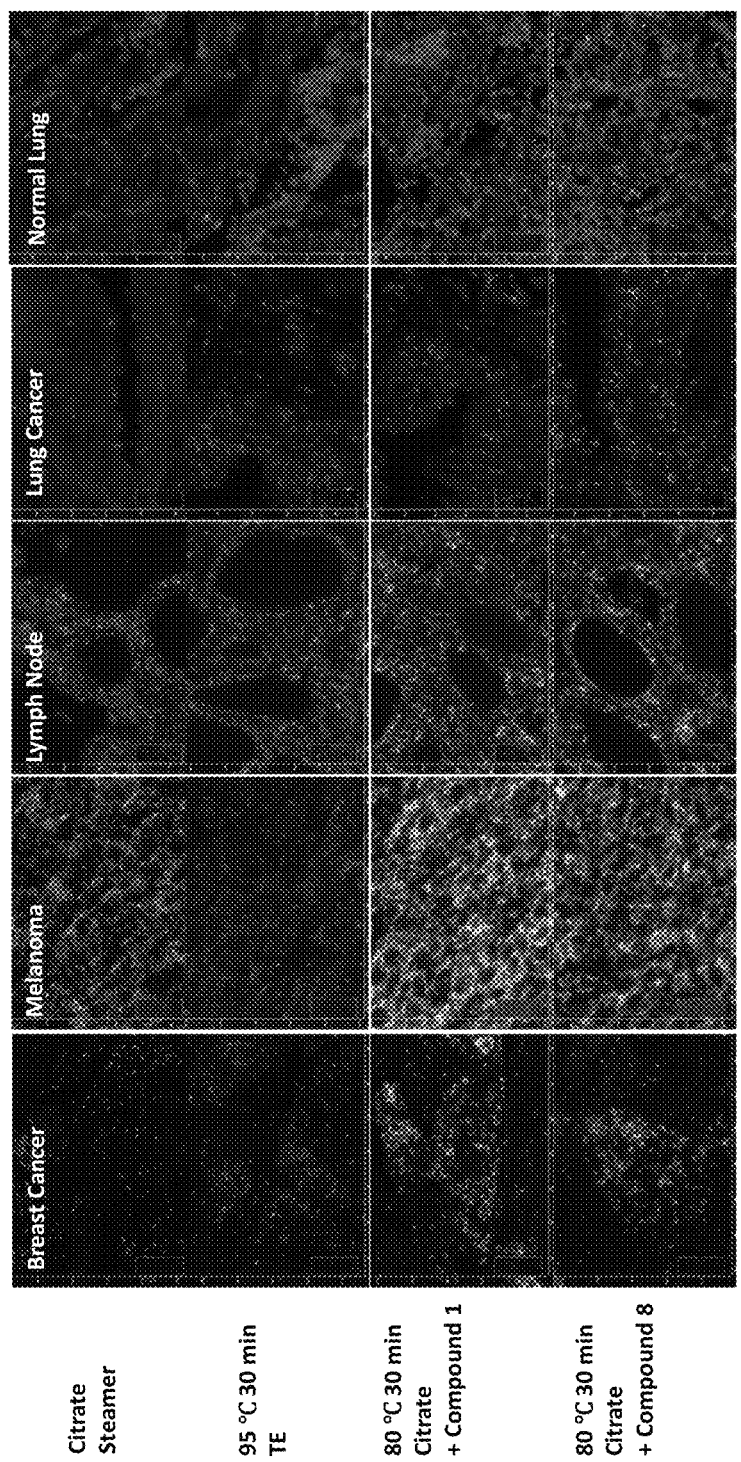
FIG. 7A shows representative images of catalytically de-crosslinked FFPE human breast cancer, melanoma, lymph node, lung cancer, and normal lung tissue samples analyzed using detectable probes targeting RCPs associated with GAPDH/RPLP0 in the samples.

FIG. 7A shows representative images of the tissue samples analyzed using detectable probes targeting the common anchor region to detect the RCPs, demonstrating that catalytic de-crosslinking using either Compound 1 or Compound 8 enhanced visualization of transcripts GAPDH/RPLP0 or MALAT-1/ACTB (data not shown) across the tissue types, as compared to de-crosslinking in a steamer.

Figure 7B:
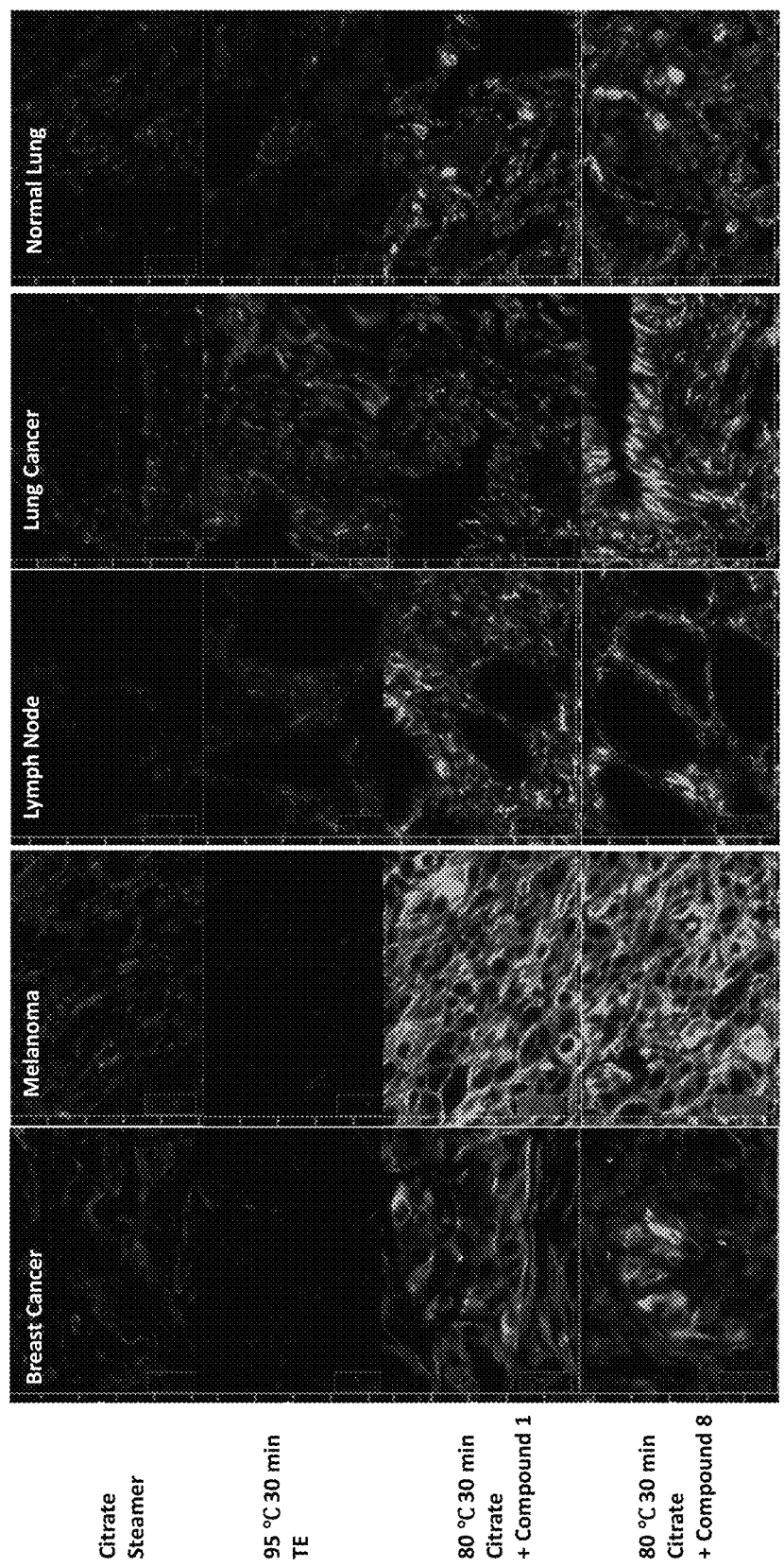
FIG. 7B shows representative images of catalytically de-crosslinked FFPE human breast cancer, melanoma, lymph node, lung cancer, and normal lung tissue samples stained with an anti-Vimentin antibody.

FIG. 7B shows representative images of the tissue samples stained with an anti-Vimentin antibody. Catalytic de-crosslinking using either Compound 1 or Compound 8 enhanced anti-Vimentin antibody staining across the tissue types, as compared to de-crosslinking in a steamer and de-crosslinking with heating at 95° C. in TE buffer.

Figure 7C:
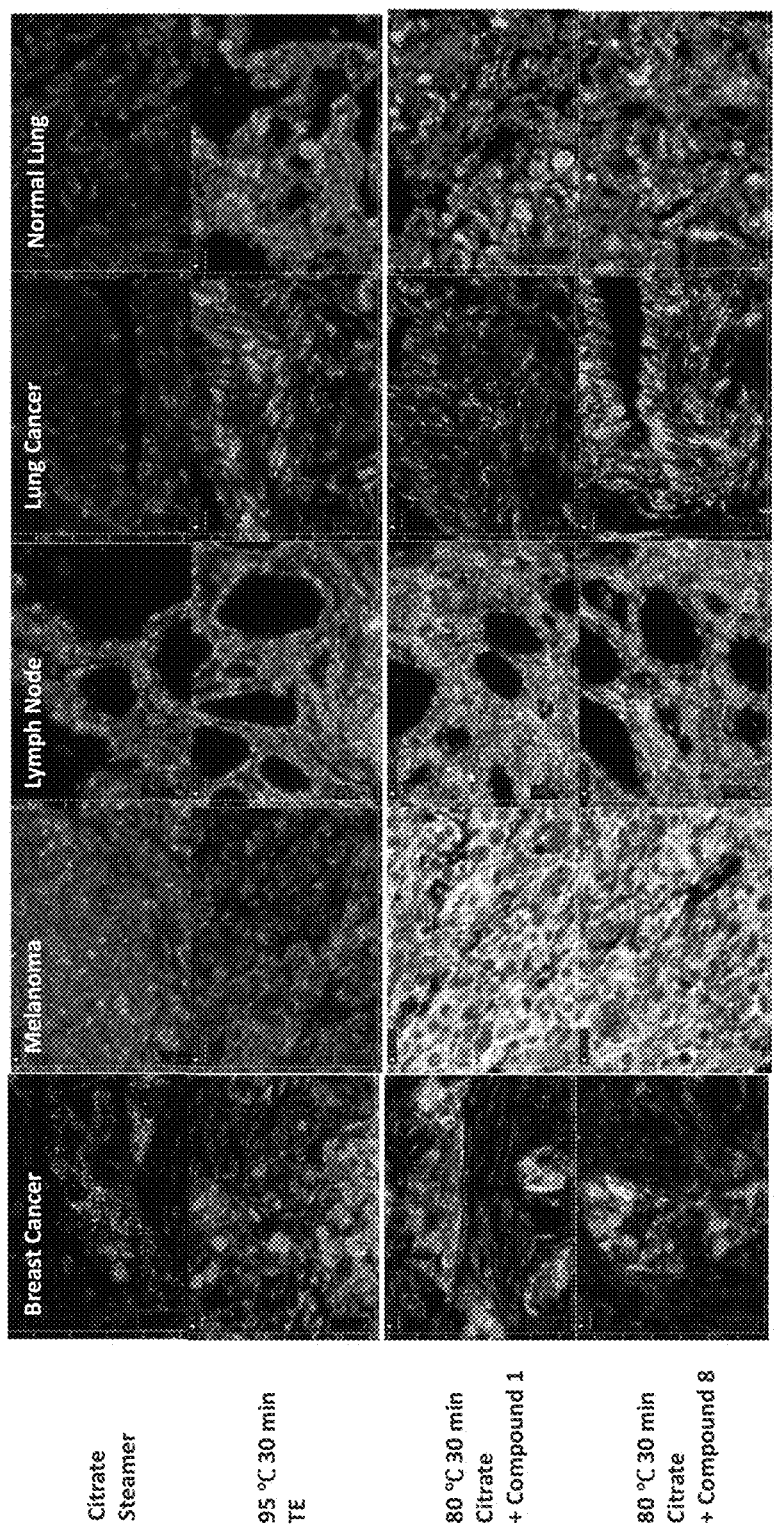
FIG. 7C shows overlaid images of nucleic acid detection and protein detection across the tissue types.

FIG. 7C shows overlaid images of RNA detection and protein detection, demonstrating that catalytic de-crosslinking using either Compound 1 or Compound 8 enhanced RNA/protein visualization across the tissue types.

Figure 8:
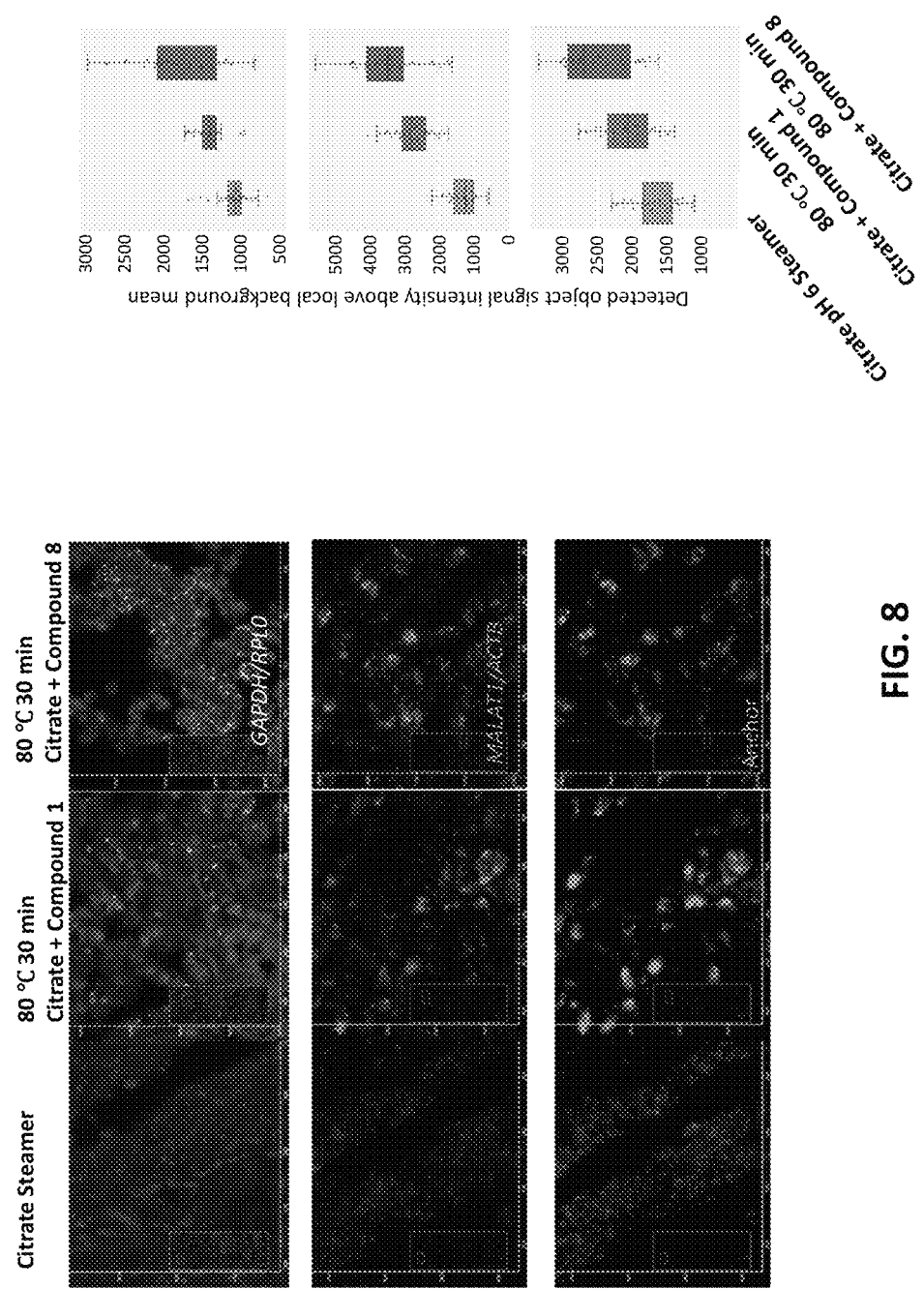
FIG. 8 shows representative images with detected RCP signals (left panel) and detected RCP signal intensity above local background (mean) (right panel) in catalytically de-crosslinked FFPE normal lung tissue samples.

FIG. 8 shows the detected object count per nucleic area (RCP count/$\mu m^2$ nuclei area) in normal lung tissue samples. The RCPs were detected using detectable probes targeting barcode sequences for MALAT-1/ACTB or GAPDH/RPLP0 or targeting the common anchor region in the RCPs (representative images in FIG. 8, left panel). Higher RCP densities (detected object count per nucleic area (RCP count/$\mu m^2$ nuclei area)) were observed in samples catalytically de-crosslinked using either Compound 1 or Compound 8, as compared to control samples de-crosslinked in a steamer (data not shown). Catalytic de-crosslinking also improved detected objected signal intensity above local background, as measured by detected object signal intensity above local background (mean) in FIG. 8, right panel.

Together these results demonstrate that catalytic de-crosslinking can improve signal detection (e.g., signal counts as well as signal-to-noise ratios) of nucleic acids and proteins in situ across different tissue types including FFPE human breast cancer, melanoma, lymph node, lung cancer, and normal lung tissues.

Example 4: Analyte Detection in De-Crosslinked FFPE Mouse Brain Tissues

FFPE mouse brain tissues were processed essentially as described in Example 1, and gene expression analysis for RNA transcripts and protein analysis (e.g., anti-GFAP antibody staining) in the dentate gyrus (DG) region were performed essentially as described in Examples 2 and 3. Four de-crosslinking agent and buffer combinations were tested: Compound 1 in citrate buffer (pH 6.8), Compound 15 in citrate buffer (pH 6.8), Compound 18 (trans-4-hydroxy-L-proline) in citrate buffer (pH 6.8), and Compound 1 in PBS (pH 7.4).

Figure 9:
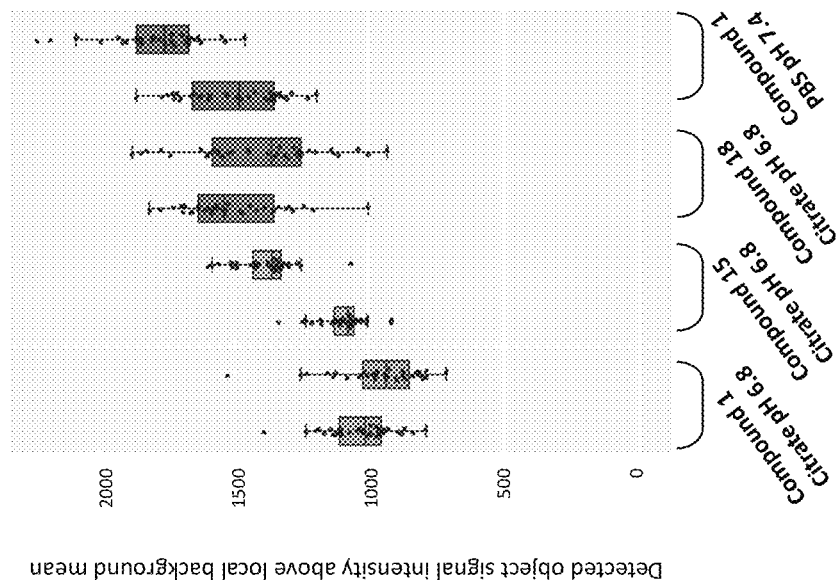
FIG. 9 shows representative images with detected RCP signals and detected RCP signal intensity above local background (mean) in catalytically de-crosslinked FFPE mouse brain tissue sections.
Figure 9:
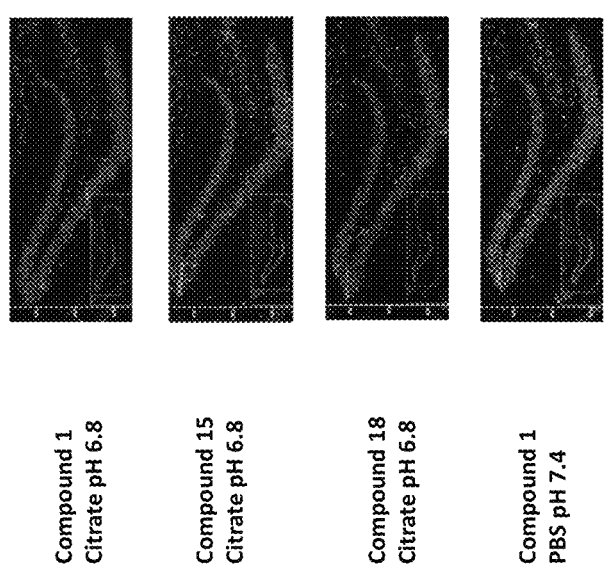

FIG. 9 shows the detected object signal intensity above local background (mean) in the mouse brain tissues, detected using detectable probes targeting the common anchor region in the RCPs. De-crosslinking with Compound 15 in citrate buffer (pH 6.8), Compound 18 in citrate buffer (pH 6.8), and Compound 1 in PBS (pH 7.4) all showed improved signal density compared to de-crosslinking with Compound 1 in citrate buffer (pH 6.8). Antibody staining was comparable among the de-crosslinking agent and buffer combinations (data not shown).

Example 5: Analyte Detection in De-Crosslinked FFPE Samples with Additives

FFPE human breast cancer samples sectioned to 5 μm thickness were processed essentially as described in Example 2. Specifically, 2-amino-5-methylbenzoic acid (Compound 1) was used as the de-crosslinking agent and applied to de-paraffinized and re-hydrated samples in a buffer solution with various additives, such as 0.05% SDS, 0.2% SDS, 0.5% SDS, 0.05 M urea, 0.5 M urea, 0.2 μg/ml proteinase K, 0.5 μg/ml proteinase K, 1 μg/ml proteinase K, and combinations thereof. The samples were incubated at 80° C. for 30 minutes, using 150 mM of Compound 1. Analytes in the de-crosslinked tissue samples were detected essentially as described in Example 2 using circularizable probes (e.g., padlock probes) targeting ACTB, GAPDH, MALAT-1, RPLP0, Eef2, Ppib, POLR2A RNA transcripts. Detectable probes were hybridized to sequences (e.g., barcode sequences or anchor sequences) in the RCPs and comprised overhangs for hybridization of fluorescently labelled detection oligonucleotides. The samples were imaged in fluorescent microscope with 40× objective and the signals associated with the RCPs were quantified using a software.

Figure 10B:
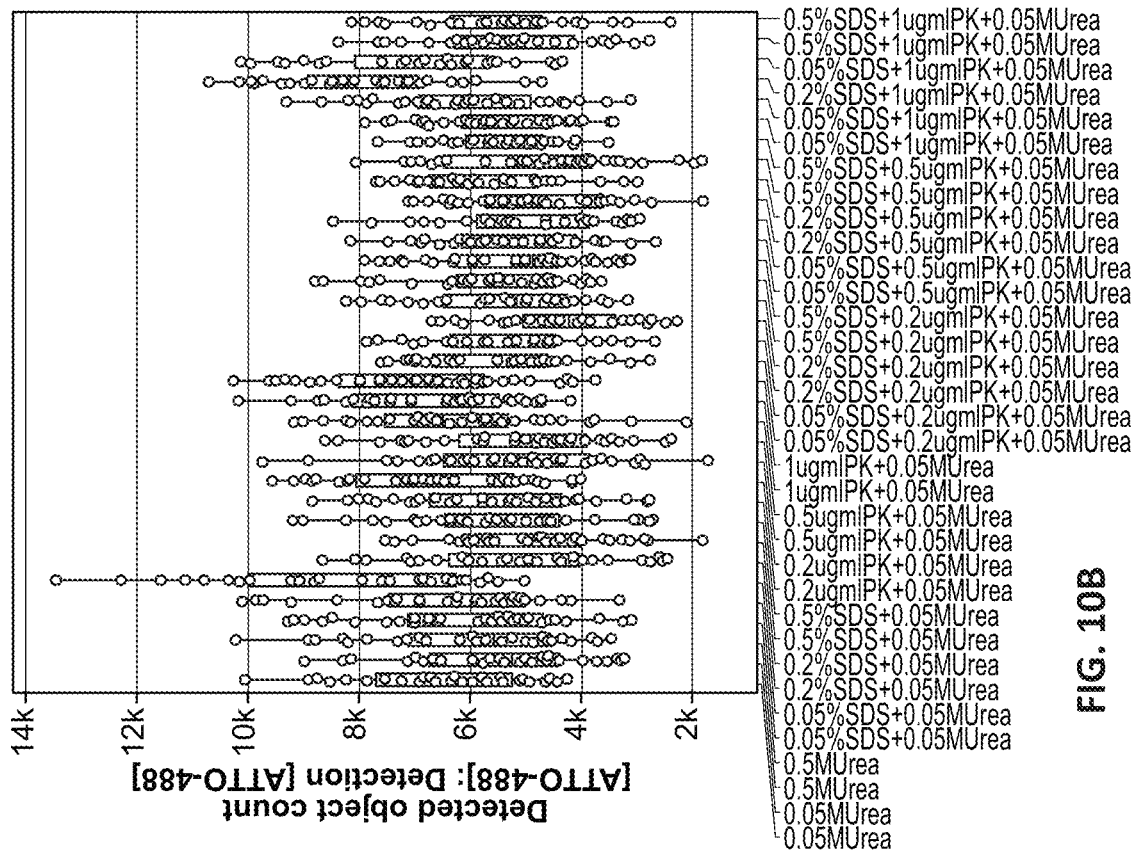
FIG. 10A-10C shows detected rolling circle amplification product (RCP) signal density (count/$\mu m^2$ nuclei area) in catalytically de-crosslinked human breast cancer samples with Compound 1 and various additives (e.g., SDS, proteinase K, and/or urea) compared to control samples de-crosslinked using Compound 1 only.
Figure 10A:
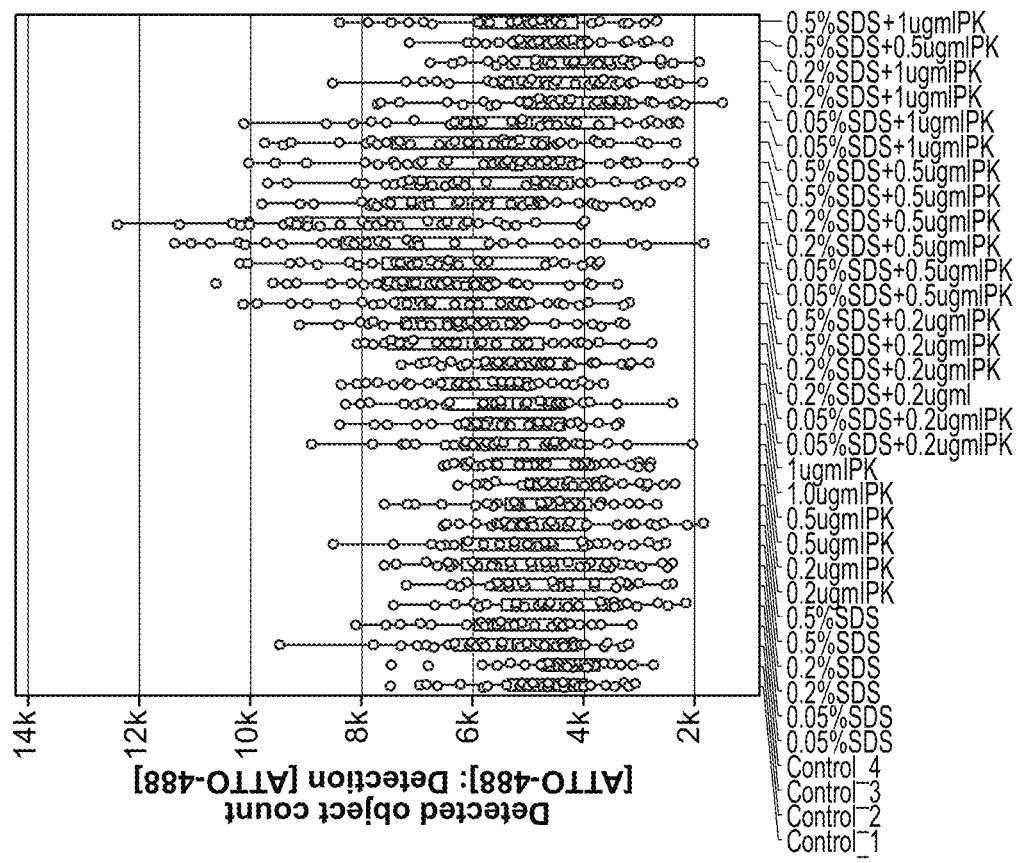
Figure 10C:
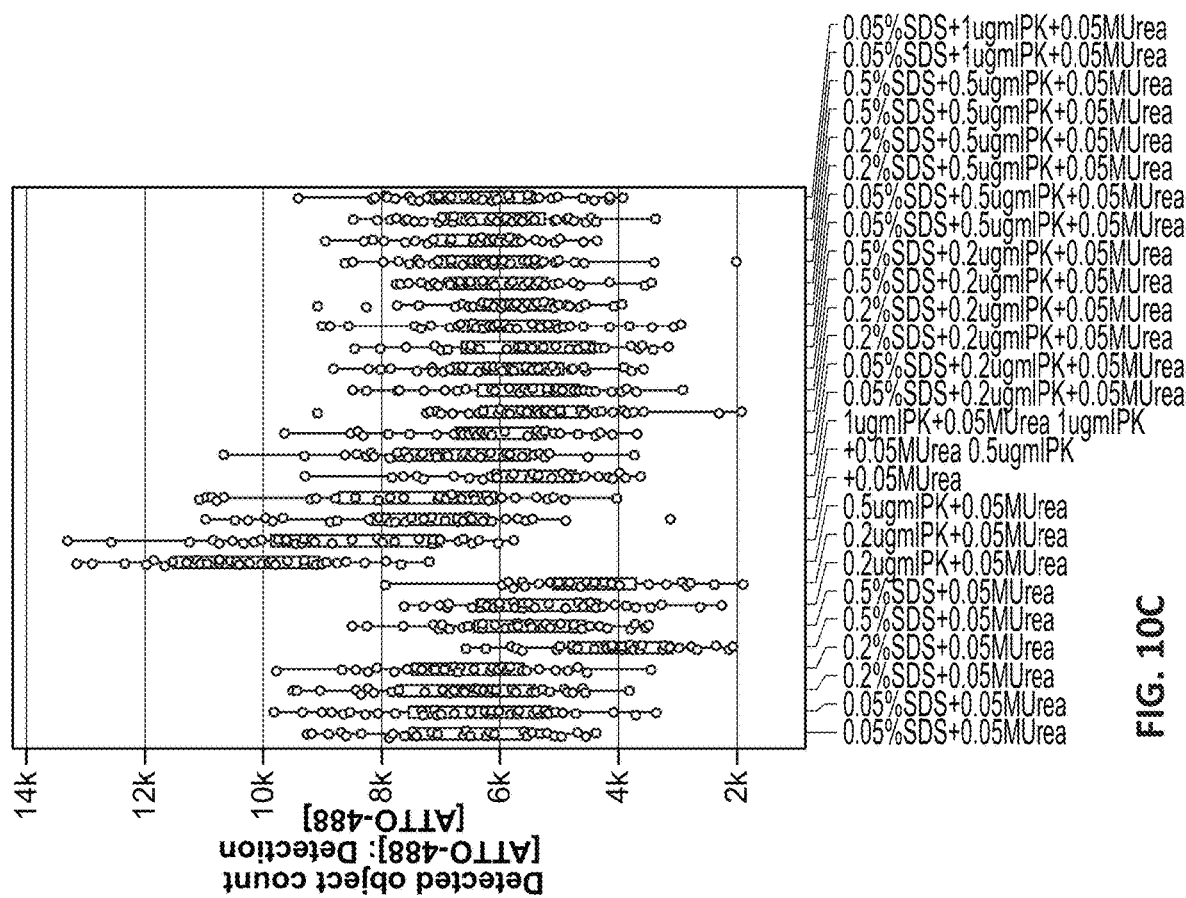

FIG. 10A-10C show the detected object count per nucleic area (RCP count/μm2 nuclei area) in cells of the human breast cancer samples treated with Compound 1 for de-crosslinking in the presence or absence of additives SDS, urea, and/or proteinase K as indicated. De-crosslinking with Compound 1 in the presence of SDS and proteinase K, or Compound 1 in the presence of urea and proteinase K appeared to improve the detection of RCPs (e.g., decreased autofluorescence, increased puncta brightness and/or increased puncta numbers), as reflected by the increased detected object counts per nucleic area as compared to control samples treated with Compound 1 with no additional additives or with single additives. In some instances, de-crosslinking using Compound 1 in the presence of both 0.5 M urea and 1 μg/ml proteinase K or Compound 1 in the presence of both 0.5 M urea with 0.5 μg/ml Proteinase K showed increases in puncta brightness and/or numbers detected. In addition, it was observed antibody staining (e.g., antibody positive signal intensity for Pan cytokeratin, Vimentin, and Ki67) was compatible with the catalytic de-crosslinking conditions with Compound 1 in the presence of urea and proteinase K. Tissue morphology was also observed to be preserved post workflow and detection as confirmed by H&E staining that was performed.

The present disclosure is not intended to be limited in scope to the particular disclosed embodiments, which are provided, for example, to illustrate various aspects of the present disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for sample analysis, comprising:
a) providing a biological sample immobilized on a substrate, wherein the biological sample is fixed;
b) contacting the biological sample with a catalyst that catalyzes de-crosslinking of molecular crosslinks in the biological sample, wherein the catalyst is a compound of formula (I),

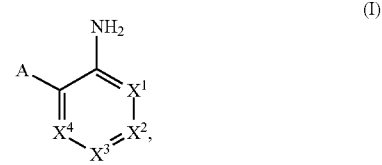

or a salt, zwitterion, or solvate thereof, wherein:
A is selected from the group consisting of —COOH, —P(=O)(OH)$_2$, and S(=O)$_2$OH;
$X^1$, $X^2$, $X^3$, and $X^4$ are each independently selected from the group consisting of: CH, CR$^a$, and N;
each occurrence of Ra is independently selected from the group consisting of $C_{1-6}$ alkyl, $C_{1-6}$ haloalkyl, $C_{1-6}$ alkoxy, —NO$_2$, —NR'R", and —C(=O)NR'R"; and
each occurrence of R' and R" is independently selected from the group consisting of H and $C_{1-6}$ alkyl which is optionally substituted with

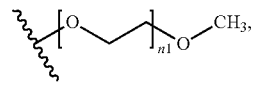

wherein n1 is an integer from 12 to 16;
c) contacting the biological sample with a nucleic acid probe that directly or indirectly binds to an RNA analyte at a location in the biological sample;
d) circularizing the nucleic acid probe to form a circularized nucleic acid probe;
e) using a polymerase to perform rolling circle amplification (RCA) using the circularized nucleic acid probe as template to generate an RCA product, optionally wherein the polymerase is a phi29 polymerase; and
f) detecting an optical signal associated with the RCA product, thereby detecting the RNA analyte at the location in the biological sample.

2. The method of claim 1, wherein the molecular crosslinks are products of one or more crosslinking agents.

3. The method of claim 2, wherein the one or more crosslinking agents comprise an aldehyde, optionally wherein the crosslinking agent comprises formaldehyde.

4. The method of claim 1, wherein the catalyst is a transamination catalyst.

5. The method of claim 1, wherein the catalyst catalyzes de-crosslinking of aminal crosslinks in the biological sample.

6. The method of claim 1, wherein the catalyst catalyzes breakdown of hemi-aminal adducts and/or aminal adducts in the biological sample.

7. The method of claim 1, wherein the catalyst comprises one or more compounds selected from the group consisting of

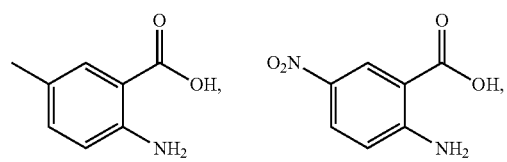

101

-continued

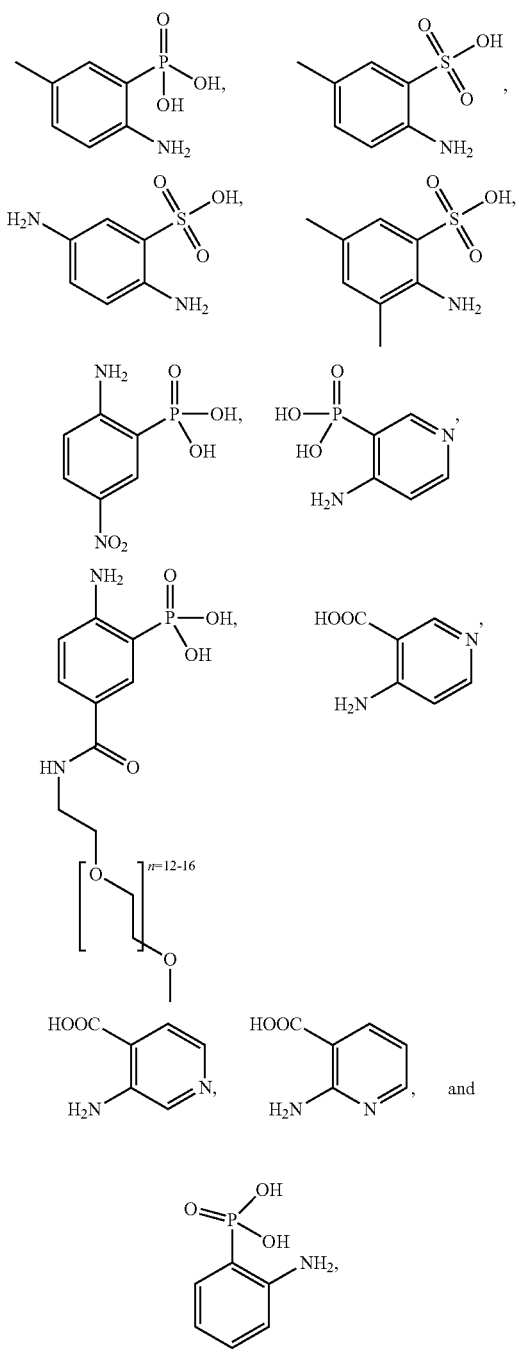

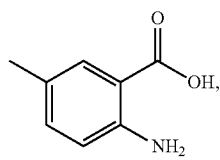

or a salt, zwitterion, or solvate thereof.

8. The method of claim 1, wherein the catalyst comprises

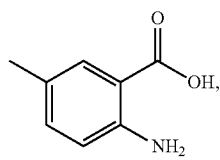

or a salt, zwitterion, or solvate thereof.

102

9. The method of claim 1, wherein the catalyst comprises

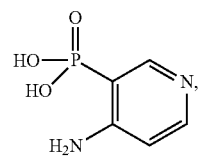

or a salt, zwitterion, or solvate thereof.

10. The method of claim 1, wherein the catalyst comprises

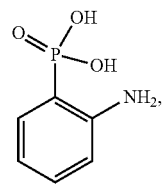

or a salt, zwitterion, or solvate thereof.

11. The method of claim 1, wherein the catalyst comprises

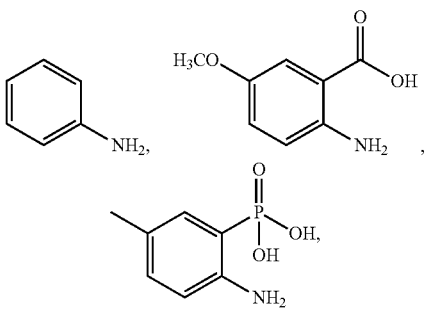

or a combination thereof, or a salt, zwitterion, or solvate thereof.

12. The method of claim 1, wherein the substrate is transparent.

13. The method of claim 1, wherein the biological sample is a tissue section.

14. The method of claim 1, wherein the biological sample is a fresh frozen biological sample that has been crosslinked or is a formaldehyde-fixed paraffin-embedded (FFPE) biological sample.

15. The method of claim 1, wherein the catalyst is contacted with the biological sample at 80° C. for 30 minutes.

16. The method of claim 1, wherein a solution or a suspension comprising the catalyst and a buffer is contacted with the biological sample.

17. The method of claim 16, wherein the buffer comprises citrate, tris(hydroxymethyl)aminomethane (Tris), phosphate-buffered saline (PBS), 2-[4-(2-hydroxyethyl)piperazin-1-yl]ethanesulfonic acid (HEPES), 2-(N-morpholino)ethanesulfonic acid (MES), or a combination thereof.

18. The method of claim 16, wherein the buffer comprises dimethyl sulfoxide (DMSO).

19. The method of claim 16, wherein the solution or suspension comprises sodium dodecyl sulfate (SDS), urea, and/or a proteinase.

20. The method of claim 19, wherein the solution or suspension comprises sodium dodecyl sulfate (SDS) and proteinase K.

21. The method of claim 19, wherein the solution or suspension comprises urea and proteinase K.

22. The method of claim 1, wherein the RNA analyte is an mRNA and the nucleic acid probe hybridizes to the mRNA.

23. The method of claim 1, comprising contacting the biological sample with a detectable probe, wherein the detectable probe hybridizes to a barcode sequence in the RCA product.

24. The method of claim 23, wherein the detectable probe comprises a barcode sequence in a region that does not hybridize to the RCA product.

25. The method of claim 23, wherein the detectable probe comprises a fluorescent label or a region for binding to a fluorescently labelled probe.

26. The method of claim 1, wherein the optical signal is detected in situ in the biological sample.

27. The method of claim 1, wherein the optical signal is detected by imaging the biological sample.

28. The method of claim 27, wherein the imaging comprises fluorescent microscopy.

* * * * *